United States Patent
Moinet et al.

(10) Patent No.: US 8,124,613 B2
(45) Date of Patent: *Feb. 28, 2012

(54) SPIROTROPANE COMPOUNDS

(75) Inventors: Christophe Moinet, Quebec (CA); Charles Blais, Quebec (CA); Monica Bubenik, Quebec (CA); Laval Chan Chun Kong, Quebec (CA); Marc Courchesne, Quebec (CA); Oswy Z. Pereira, Quebec (CA); Réal Denis, Quebec (CA); Louis Vaillancourt, Quebec (CA); Constantin G. Yannopoulos, Quebec (CA)

(73) Assignee: Virochem Pharma Inc., Quebec (CA)

( * ) Notice: Subject to any disclaimer, the term of this patent is extended or adjusted under 35 U.S.C. 154(b) by 250 days.

This patent is subject to a terminal disclaimer.

(21) Appl. No.: 12/304,685

(22) PCT Filed: Jun. 14, 2007

(86) PCT No.: PCT/CA2007/001062
§ 371 (c)(1),
(2), (4) Date: Sep. 8, 2009

(87) PCT Pub. No.: WO2007/143847
PCT Pub. Date: Dec. 21, 2007

(65) Prior Publication Data
US 2011/0105546 A1    May 5, 2011

Related U.S. Application Data

(60) Provisional application No. 60/813,366, filed on Jun. 14, 2006, provisional application No. 60/813,367, filed on Jun. 14, 2006.

(51) Int. Cl.
*A61K 31/44* (2006.01)
*C07D 401/00* (2006.01)

(52) U.S. Cl. .......................... 514/278; 546/18

(58) Field of Classification Search .............. 514/278; 546/18
See application file for complete search history.

(56) References Cited

U.S. PATENT DOCUMENTS

| | | | |
|---|---|---|---|
| 7,560,468 B2 * | 7/2009 | Sundermann et al. ........ | 514/278 |
| 7,960,403 B2 * | 6/2011 | Chan Chun Kong et al. | 514/278 |
| 2005/0075326 A1 | 4/2005 | Chan Chun Kong et al. | |
| 2005/0075360 A1 | 4/2005 | Chan Chun Kong et al. | |

FOREIGN PATENT DOCUMENTS

| | | |
|---|---|---|
| WO | WO 2005/007656 A1 | 1/2005 |
| WO | WO 2005/023810 A1 | 3/2005 |
| WO | WO 2006/060918 A1 | 6/2006 |
| WO | WO 2006/060919 A1 | 6/2006 |

OTHER PUBLICATIONS

Villacampa et al. CAS: 118:212959, 1992.*
Bellanato et al. CAS: 94:207963, 1981.*
CAPLUS: 72402-24-5 (1979)—Abstract.
CAPLUS: 77699-15-1 (1981)—Abstract.
CAPLUS: 64192-77-4 (1977)—Abstract & CAPLUS: 64192-79-6 (1977)—Abstract.

* cited by examiner

*Primary Examiner* — Rei-tsang Shiao
(74) *Attorney, Agent, or Firm* — Millen, White, Zelano & Branigan, P.C.

(57) ABSTRACT

Compounds according to formula (I):

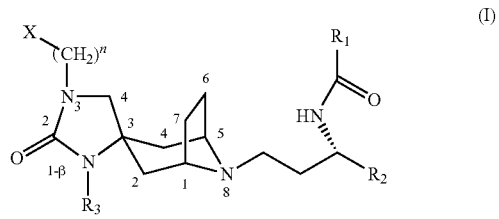

wherein $R_1$, $R_2$, $R_3$, n and X are defined as defined herein, and the pharmaceutically acceptable salts, hydrates and solvates thereof, are useful for the modulation of CCR5 chemokine receptor activity. Additionally, compounds according to Formula III:

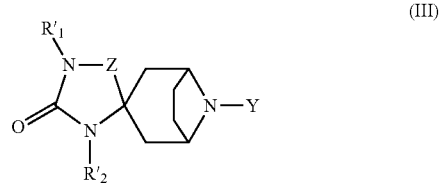

wherein Z, $R'_1$, and $R'_2$ are defined as defined herein, and the pharmaceutically acceptable salts, hydrates and solvates thereof, are useful as intermediates for production of compounds that modulate CCR5 chemokine receptor activity.

38 Claims, No Drawings

SPIROTROPANE COMPOUNDS

This application claims the benefit of the filing date of U.S. Provisional Application Ser. No. 60/813,366 filed Jun. 14, 2006 and U.S. Provisional Application Ser. No. 60/813,367 filed Jun. 14, 2006.

FIELD OF THE INVENTION

The present invention relates to novel spirotropane compounds and a method of modulating chemokine receptor activity using these compounds. The present invention is also directed to novel spirotropane compounds which are useful in the prevention or treatment of HIV infections. The present invention is also directed to novel spirotropane compounds which are useful in the prevention or treatment of diseases associated with the modulation of CCR5 chemokine receptor activity. The present invention is further directed to a method of blocking cellular entry of HIV in a subject and to compositions using these compounds.

Additionally, the present invention relates to novel spirotropane compounds useful as intermediates for the synthesis of other novel spirotropane compounds, the latter being useful in the prevention or treatment of diseases associated with the modulation of CCR5 chemokine receptor activity.

BACKGROUND OF THE INVENTION

Despite 20 years of outstanding scientific accomplishments in the field of HIV research, from the identification of HIV as the causative agent for AIDS to the development of effective antiretroviral drugs, the AIDS epidemic remains a formidable global health challenge. Most anti-HIV medications available to date belong to two classes of inhibitors that target viral enzymes: reverse transcriptase and protease. Although highly active antiretroviral therapy (HAART) has been effective in reducing the mortality and morbidity in recent years, issues such as long term side effects, customized and complicated dosing regimens and, more seriously, the emergence of multidrug-resistant viral variants, still remain. These challenges have prompted the search for new treatment agents beyond viral reverse transcriptase and protease inhibitors and the discovery of new classes of potent and less-toxic anti-HIV-1 drugs with a different mechanism of action is needed.

Chemokines are chemotactic cytokines that are released by a wide variety of cells to attract macrophages, T cells, eosinophils, basophils and neutrophils to sites of inflammation and they also play a role in the maturation of cells of the immune system. Chemokines play an important role in immune and inflammatory responses in various diseases and disorders, including asthma, rhinitis and allergic diseases, as well as autoimmune pathologies such as rheumatoid arthritis and atherosclerosis. Chemokines are small 70 to 80 amino acid proteins with well-characterized three-dimensional structures, usually stabilized by two disulfide bridges. They are divided into four families on the basis of pattern of conserved cysteine residues. Chemokine receptors have been designated such as, CCR1, CCR2, CCR2A, CCR2B, CCR3, CCR4, CCR5, CCR6, CCR7, CCR8, CCR9, CCR10, CXCR1, CXCR2, CXCR3, and CXCR4 and therefore agents which modulate these receptors may be useful in the prevention and treatment of diseases as mentioned above.

For a review of possible applications of chemokines and chemokine receptor blockers see Riberio and Horuk, "The Clinical Potential of Chemokine Receptor Antagonists", Pharmacology and Therapeutics 107 (2005) p 44-58.

One of them, the C—C chemokines family, includes potent chemoattractants of monocytes and lymphocytes such as RANTES (Regulated on Activation, Normal T Expressed and Secreted), eotaxin, MIP-1α and MIP-1β (Macrophage Inflammatory Proteins) and human monocyte chemotactic proteins 1-3 (MCP-1, MCP-2 and MCP-3). More specifically, C—C chemokine receptor 5 (CCR5), a β-chemokine receptor with a seven-transmembrane-protein structure, was found to serve as a coreceptor for non-syncytium-inducing or macrophage-tropic HIV-1 (R5 viruses). It was also established that CCR5 is the principal chemokine receptor required for the entry of HIV into the cell during primary infection. Therefore, interfering with the interaction between the viral receptor CCR5 and HIV can block HIV entry into the cell. It would therefore be useful to provide novel compounds which are modulators of chemokine receptor activity.

PCT applications PCT/CA2005/001877 or PCT/CA2005/001878 disclose certain spirotropane compounds that are useful for the prevention or treatment of HIV infections, as well as diseases associated with the modulation of CCR5 chemokine receptor activity.

Compounds of the present invention are generically disclosed in PCT applications PCT/CA2005/001877 or PCT/CA2005/001878 but none is specifically exemplified therein.

SUMMARY OF THE INVENTION

In one aspect, the present invention provides novel compounds represented by formula (I):

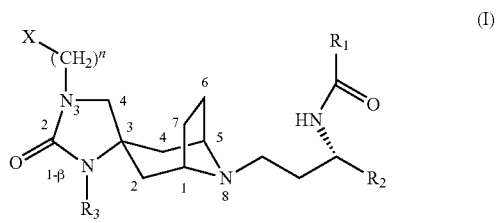

or pharmaceutically acceptable salts, hydrates or solvates thereof,
wherein:
X is an optionally substituted 4 to 7 membered ring comprising 1 or 2 oxygen atoms, provided that when X is a 4 membered ring it comprises only one oxygen atom;
n is 0, 1, or 2;
$R_1$ is optionally substituted $C_{1-10}$ alkyl, optionally substituted $C_{2-10}$ alkenyl, optionally substituted $C_{2-10}$ alkynyl or optionally substituted 4 to 7 member heterocycle;
$R_2$ is optionally substituted $C_{6-12}$ aryl; and
$R_3$ is optionally substituted $C_{1-10}$ alkyl, optionally substituted $C_{2-10}$ alkenyl, optionally substituted $C_{2-10}$ alkynyl;
provided that when —$(CH_2)_n$—X is tetrahydrofuran, tetrahydropyran, oxetanyl($CH_2$)—, tetrahydrofuran($CH_2$)— or tetrahydropyran($CH_2$)—, and $R_3$ is isopropyl, then $R_1$ is not 4,4-difluorocyclohexyl.

In another aspect, there is provided a method of modulating chemokine receptor activity in a subject comprising administering to the subject an effective amount of a compound of formula (I) or composition of the invention.

In still another aspect, there is provided a method for prevention or treatment of certain inflammatory diseases, immunoregulatory diseases, organ transplantation reactions and in the prevention and treatment of infectious diseases such as HIV infections in a subject in need of such treatment comprising administering to the subject a therapeutically effective amount of a compound of formula (I) or composition of the invention.

In still another aspect, there is provided a method for treatment of asthma in a subject in need of such treatment comprising administering to the subject a therapeutically effective amount of a compound of formula (I) or composition of the invention.

In still another aspect, there is provided a method for treatment of rhinitis in a subject in need of such treatment comprising administering to the subject a therapeutically effective amount of a compound of formula (I) or composition of the invention.

In still another aspect, there is provided a method for treatment of rheumatoid arthritis in a subject in need of such treatment comprising administering to the subject a therapeutically effective amount of a compound of formula (I) or composition of the invention.

In still another aspect, there is provided a method for treatment of atherosclerosis in a subject in need of such treatment comprising administering to the subject a therapeutically effective amount of a compound of formula (I) or composition of the invention.

In still another aspect, there is provided a method for the prevention or treatment of diseases associated with the modulation of CCR5 chemokine receptor activity in a subject in need of such treatment comprising administering to the subject a therapeutically effective amount of a compound of formula (I) or composition of the invention.

In still another aspect, there is provided a method for blocking cellular entry of HIV in a subject comprising administering to the subject in need thereof an effective amount of a compound of formula (I) or composition of the invention to block HIV from cellular entry in said subject.

In still another aspect, there is provided a method for the prevention or treatment of diseases associated with the modulation of chemokine receptor activity in a subject in need of such treatment comprising administering to the subject a pharmaceutical combination comprising at least one compound of formula (I) and at least one further therapeutic agent.

In another aspect, there is provided a pharmaceutical formulation comprising the compound of the invention in combination with a pharmaceutically acceptable carrier or excipient.

In another aspect of the invention is the use of a compound according to formula (I), for the manufacture of a medicament for the prevention or treatment of diseases associated with the modulation of chemokine receptor activity.

In another embodiment of the invention, the compounds, combinations, methods or uses of the present invention comprise those wherein the following embodiments of the variable groups of Formula I are present, either independently or in combination.

According to another aspect, the present invention provides compounds represented by formula (III):

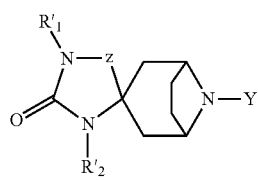

(III)

Wherein;
Z is C(O) or CH$_2$;
R'$_1$ and R'$_2$ are each, independently, H, optionally substituted C$_{1-10}$ alkyl, optionally substituted C$_{2-10}$ alkenyl, optionally substituted C$_{2-10}$ alkynyl, optionally substituted C$_{6-12}$ aryl, optionally substituted 3 to 10 membered heterocycle, optionally substituted C$_{7-12}$ aralkyl or optionally substituted heteroaralkyl (e.g., wherein the heteroaryl portion has 3 to 10 members and the alkyl portion has 1 to 6 carbon atoms), wherein at least one of R'$_1$ and R'$_2$ is other than H;
Y is H or a nitrogen protecting group;
with the provisos that:
1) when Z is CH$_2$ or C(O), and R'$_1$ is methyl or ethyl, then R'$_2$ is other than isopropyl or ethyl;
2) when Z is C(O), and R'$_1$ is

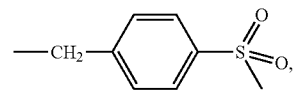

then R'$_2$ is other than H.

The spirotropane compounds of the present invention are useful for the synthesis of spirotropane compounds of Formula I and spirotropane compounds described in PCT applications PCT/CA2005/001877 and/or PCT/CA2005/001878.

In one embodiment, compounds of the present invention comprise those wherein the following embodiments of the variable groups of Formula III are present, either independently or in combination.

DETAILED DESCRIPTION

According to one aspect of the invention, when —(CH$_2$)$_n$—X is tetrahydrofuran, tetrahydropyran, oxetanyl (CH$_2$)—, tetrahydrofuran(CH$_2$)— or tetrahydropyran (CH$_2$)—, and R$_3$ is isopropyl, then R$_1$ is not halogenated cyclohexyl.

According to one aspect of the invention, when —(CH$_2$)$_n$—X is tetrahydrofuran, tetrahydropyran, oxetanyl (CH$_2$)—, tetrahydrofuran(CH$_2$)— or tetrahydropyran (CH$_2$)—, and R$_3$ is unsubstituted C$_{2-4}$ alkyl, then R$_1$ is not halogenated cyclohexyl.

According to one aspect of the invention, when —(CH$_2$)$_n$—X is tetrahydrofuran, tetrahydropyran, oxetanyl (CH$_2$)—, tetrahydrofuran(CH$_2$)— or tetrahydropyran (CH$_2$)—, and R$_3$ is unsubstituted C$_{1-4}$ alkyl, then R$_1$ is not halogenated cyclohexyl.

According to one aspect of the invention, X—(CH$_2$)$_n$— is oxetanyl, tetrahydrofuranyl, tetrahydropyranyl, oxepanyl, dioxolanyl, dioxanyl, oxetanyl-CH$_2$—, tetrahydrofuranyl-CH$_2$—, tetrahydropyranyl-CH$_2$—, oxepanyl-CH$_2$—, dioxolanyl-CH$_2$—, dioxanyl-CH$_2$—, any of which can be unsubstituted or substituted by one or more substituents chosen from halogen, hydroxy, C$_{1-6}$ alkyl, NR$_{63}$R$_{64}$, nitro, CONR$_{63}$R$_{64}$, C$_{1-6}$ alkyloxy, C(O)OR$_{62}$, cyano, and azido;
wherein R$_{62}$, R$_{63}$ and R$_{64}$ are each independently chosen from H, C$_{1-12}$ alkyl, C$_{6-12}$ aryl, 3-10 member heterocycle, 4-16 member heteroaralkyl, and C$_{7-18}$ aralkyl;
or R$_{63}$ and R$_{64}$ are taken together with the nitrogen atom to form a 3 to 10 member heterocycle.

According to another aspect of the invention, X—(CH$_2$)$_n$— is oxetanyl, tetrahydrofuranyl, tetrahydropyranyl, oxepanyl, dioxolanyl, dioxanyl, oxetanyl-CH$_2$—, tetrahydrofuranyl-CH$_2$—, tetrahydropyranyl-CH$_2$—, oxepanyl-CH$_2$—, dioxolanyl-CH$_2$—, dioxanyl-CH$_2$—, any of which can be unsubstituted or substituted by one or more substituents chosen from halogen, $C_{1-6}$ alkyl, $NR_{63}R_{64}$, nitro, $CONR_{63}R_{64}$, $C_{1-6}$ alkyloxy, $C(O)OR_{62}$, cyano, and azido;
  wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl;
  or $R_{63}$ and $R_{64}$ are taken together with the nitrogen atom to form a 3 to 10 member heterocycle.

According to a further aspect of the invention, X—$(CH_2)_n$— is oxetanyl, tetrahydrofuranyl, tetrahydropyranyl, oxepanyl, dioxolanyl, dioxanyl, oxetanyl-$CH_2$—, tetrahydrofuranyl-$CH_2$—, tetrahydropyranyl-$CH_2$—, oxepanyl-$CH_2$, -dioxolanyl-$CH_2$—, dioxanyl-$CH_2$—, any of which can be unsubstituted or substituted by one or more substituents chosen from a halogen, hydroxy, $C_{1-6}$ alkyl, $C_{1-6}$ alkyloxy, $CF_3$, COOH, $COOC_{1-6}$ alkyl, cyano, $NH_2$, nitro, $NH(C_{1-6}$ alkyl), $N(C_{1-6}$ alkyl)$_2$ and 3-8 member heterocycle.

According to a further aspect of the invention, X—$(CH_2)_n$— is oxetanyl, tetrahydrofuranyl, tetrahydropyranyl, oxepanyl, dioxolanyl, dioxanyl, oxetanyl-$CH_2$—, tetrahydrofuranyl-$CH_2$—, tetrahydropyranyl-$CH_2$—, oxepanyl-$CH_2$, -dioxolanyl-$CH_2$—, dioxanyl-$CH_2$—, any of which can be unsubstituted or substituted by one or more substituents chosen from a halogen, $C_{1-6}$ alkyl, $C_{1-6}$ alkyloxy, $CF_3$, COOH, $COOC_{1-6}$ alkyl, cyano, $NH_2$, nitro, $NH(C_{1-6}$ alkyl), $N(C_{1-6}$ alkyl)$_2$ and 3-8 member heterocycle.

According to a further aspect of the invention, X—$(CH_2)_n$— is oxetanyl, tetrahydrofuranyl, tetrahydropyranyl, oxepanyl, dioxolanyl, dioxanyl, oxetanyl-$CH_2$—, tetrahydrofuranyl-$CH_2$—, tetrahydropyranyl-$CH_2$—, oxepanyl-$CH_2$—, dioxolanyl-$CH_2$—, dioxanyl-$CH_2$—, any of which can be unsubstituted or substituted by one or more substituents chosen from halogen, hydroxy, $C_{1-6}$ alkyl, $NH_2$, nitro, $C(O)OC_{1-6}$ alkyl, COOH, $C_{1-6}$ alkyloxy, cyano, and azido.

According to a further aspect of the invention, X—$(CH_2)_n$— is oxetanyl, tetrahydrofuranyl, tetrahydropyranyl, oxepanyl, dioxolanyl, dioxanyl, oxetanyl-$CH_2$—, tetrahydrofuranyl-$CH_2$—, tetrahydropyranyl-$CH_2$—, oxepanyl-$CH_2$—, dioxolanyl-$CH_2$—, dioxanyl-$CH_2$—, any of which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido.

According to a further aspect of the invention, X—$(CH_2)_n$— is tetrahydrofuranyl, tetrahydropyranyl, dioxolanyl, dioxanyl, tetrahydrofuranyl-$CH_2$—, tetrahydropyranyl-$CH_2$, dioxolanyl-$CH_2$—, dioxanyl-$CH_2$—, any of which can be unsubstituted or substituted by one or more substituents chosen from halogen, hydroxy, $C_{1-6}$ alkyl, $NH_2$, nitro, $C(O)OC_{1-6}$ alkyl, COOH, $C_{1-6}$ alkyloxy, cyano, and azido.

According to a further aspect of the invention, X—$(CH_2)_n$— is tetrahydrofuranyl, tetrahydropyranyl, dioxolanyl, dioxanyl, tetrahydrofuranyl-$CH_2$—, tetrahydropyranyl-$CH_2$, dioxolanyl-$CH_2$—, dioxanyl-$CH_2$—, any of which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido.

According to a further aspect of the invention, X—$(CH_2)_n$— is tetrahydrofuranyl-$CH_2$—, tetrahydropyranyl-$CH_2$—, oxepanyl-$CH_2$, -dioxolanyl-$CH_2$—, dioxanyl-$CH_2$—, any of which can be unsubstituted or substituted by one or more substituents chosen from halogen, hydroxy, $C_{1-6}$ alkyl, $NH_2$, nitro, $C(O)OC_{1-6}$ alkyl, COOH, $C_{1-6}$ alkyloxy, cyano, and azido.

According to a further aspect of the invention, X—$(CH_2)_n$— is tetrahydrofuranyl-$CH_2$—, tetrahydropyranyl-$CH_2$—, oxepanyl-$CH_2$, -dioxolanyl-$CH_2$—, dioxanyl-$CH_2$—, any of which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido.

According to a further aspect of the invention, X—$(CH_2)_n$— is tetrahydropyranyl-$CH_2$—.

In a further embodiment n is 0.
In a further embodiment n is 1.

According to a further aspect of the invention, $R_1$ is $C_{1-6}$ alkyl optionally substituted.

According to a further aspect of the invention, $R_1$ is $C_{3-7}$ cycloalkyl optionally substituted.

According to a further aspect of the invention, $R_1$ is cyclohexyl optionally substituted.

According to a further aspect of the invention, $R_1$ is $C_{5-7}$ cycloalkenyl optionally substituted.

According to a further aspect of the invention, $R_1$ is methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl, any of which can be unsubstituted or substituted by one or more substituents chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, oxo, oxime, $NR_{63}R_{64}$, $C(O)OR_{62}$, cyano, azido, amidino, and guanido;
  wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl,
  or $R_{65}$ and $R_{66}$ are taken together with the oxygen atoms to form a 5 to 10 member heterocycle,
  or $R_{63}$ and $R_{64}$ are taken together with the nitrogen atom to form a 3 to 10 member heterocycle.

According to a further aspect of the invention, $R_1$ is cyclohexyl, cyclopentyl, cyclobutyl, or cyclopropyl, which in each case is unsubstituted or substituted by one or more substituents independently chosen from halogen, nitro, nitroso, $SO_3Rf$, $SO_2Rf$, $PO_3R_{65}R_{66}$, CONRgRh, $C_{1-6}$ alkyl, $C_{7-18}$ aralkyl, $C_{6-12}$ aryl, $C_{1-6}$ alkyloxy, $C_{6-12}$ aryloxy, $C(O)C_{1-6}$ alkyl, $C(O)C_{6-12}$ aryl, $C(O)C_{7-12}$ aralkyl, C(O)NHRf, 3-10 member heterocycle, 4-16 member heteroaralkyl, hydroxyl, oxo, oxime, NRgRh, C(O)ORf, cyano, azido, amidino, and guanido;
  wherein Rf, $R_{65}$, $R_{66}$, Rg and Rh in each case are independently H, $C_{1-6}$ alkyl, $C_{2-6}$ alkenyl, $C_{2-6}$ alkynyl, $C_{6-12}$ aryl, 3-10 member heterocycle, 4-16 member heteroaralkyl, or $C_{7-18}$ aralkyl.

According to a further aspect of the invention, $R_1$ is cyclopentenyl which can be unsubstituted or substituted by one or more substituents chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)O_{7-12}$ aralkyl, 3-10 member heterocycle, 4-16 member heteroaralkyl, hydroxyl, oxo, oxime, $NR_{63}R_{64}$, $C(O)OR_{62}$, cyano, azido, amidino, and guanido;
  wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl,
  or $R_{65}$ and $R_{66}$ are taken together with the oxygen atoms to form a 5 to 10 member heterocycle, or $R_{63}$ and $R_{64}$ are taken together with the nitrogen atom to form a 3 to 10 member heterocycle.

According to a further aspect of the invention, $R_1$ is chosen from methyl, ethyl, vinyl, propyl, propenyl, isopropyl, butyl, isobutyl, pentyl, neopentyl, or tert-butyl.

According to a further aspect of the invention, $R_1$ is isopropyl.

According to a further aspect of the invention, $R_1$ is isobutyl.

According to a further aspect of the invention, $R_1$ is cyclohexyl.

In a further embodiment, $R_2$ is a $C_{6-12}$ aryl and 3-10 member heterocycle, which in each case are optionally substituted.

In a further embodiment, $R_2$ is a $C_{6-12}$ aryl or a 3-6 member heterocycle, which in each case are optionally substituted.

In a further embodiment, $R_2$ is $C_{6-12}$ aryl.

In a further embodiment, $R_2$ is an aryl chosen from phenyl, indenyl, naphthyl and biphenyl, which in each case are optionally substituted.

In a further embodiment, $R_2$ is unsubstituted phenyl or phenyl substituted with at least one substituent chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, $NR_{63}R_{64}$, $C(O)OR_{62}$, cyano, azido, amidino, and guanido;
  wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl,
  or $R_{65}$ and $R_{66}$ are taken together with the oxygen atoms to form a 5 to 10 member heterocycle,
  or $R_{63}$ and $R_{64}$ are taken together with the nitrogen atom to form a 3 to 10 member heterocycle.

In a further embodiment, $R_2$ is unsubstituted phenyl or phenyl substituted with at least one substituent chosen from halogen, nitro, $CONR_{63}R_{64}$, $C_{1-6}$ alkyl, $C_{2-6}$ alkenyl, $C_{1-6}$ alkyloxy, $C_{2-6}$ alkenyloxy, $C_{2-6}$ alkynyloxy, $C(O)C_{1-6}$ alkyl, $C_{6-12}$ aryl, 3-10 member heterocycle, 4-16 member heteroaralkyl, hydroxyl, $NR_{63}R_{64}$, $C(O)OR_{62}$, cyano, and azido;
  wherein $R_{62}$, $R_{63}$ and $R_{64}$ are each independently chosen from H, $C_{1-12}$ alkyl, $C_{6-12}$ aryl, 3-12 member heterocycle, 4-16 member heteroaralkyl, and $C_{7-18}$ aralkyl,
  or $R_{63}$ and $R_{64}$ are taken together with the nitrogen atom to form a 3 to 10 member heterocycle.

In a further embodiment, $R_2$ is unsubstituted phenyl or phenyl substituted with at least one substituent chosen from halogen, $C_{1-6}$ alkyl, $NR_{63}R_{64}$, nitro, $CONR_{63}R_{64}$, $C(O)OC_{1-6}$ alkyl, $C_{1-6}$ alkyloxy, $C(O)OR_{62}$, cyano, and azido;
  wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl,
  or $R_{63}$ and $R_{64}$ are taken together with the nitrogen atom to form a 3 to 10 member heterocycle.

In a further embodiment, $R_2$ is unsubstituted phenyl or phenyl substituted with at least one substituent chosen from halogen, $C_{1-6}$ alkyl, $C_{1-6}$ alkyloxy, $CF_3$, COOH, $COOC_{1-6}$ alkyl, cyano, $NH_2$, nitro, $NH(C_{1-6}$ alkyl), $N(C_{1-6}$ alkyl)$_2$ and 3-8 member heterocycle.

In a further embodiment, $R_2$ is optionally substituted $C_{6-12}$ aryl;

$R_2$ is phenyl;
$R_2$ is phenyl substituted with halogen;
$R_2$ is phenyl substituted with Cl;
$R_2$ is phenyl substituted with F; or
$R_2$ is phenyl substituted with at least one halogen.

In a further embodiment, $R_3$ is optionally substituted $C_{1-12}$ alkyl (e.g., methyl, ethyl, isopropyl, isobutyl, cyclopropyl, cyclobutyl, tert-butyl, cyclopentyl, cyclohexyl, or cycloheptyl).

In a further embodiment, $R_3$ is $C_{1-12}$ alkyl optionally substituted.

In a further embodiment, $R_3$ is $C_{1-6}$ alkyl optionally substituted.

In a further embodiment, $R_3$ is $C_{3-12}$ cycloalkyl optionally substituted.

In a further embodiment, $R_3$ is $C_{3-10}$ cycloalkyl optionally substituted.

In a further embodiment, $R_3$ is $C_{5-7}$ cycloalkyl optionally substituted.

In a further embodiment, $R_3$ is optionally substituted $C_{6-7}$ cycloalkyl.

In a further embodiment, $R_3$ is optionally substituted $C_6$ cycloalkyl.

In a further embodiment, $R_3$ is methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl, any of which unsubstituted or substituted by one or more substituents chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloky, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, oxo, oxime, $NR_{63}R_{64}$, $C(O)OR_{62}$, cyano, azido, amidino, and guanido;
  wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl,
  or $R_{65}$ and $R_{66}$ are taken together with the oxygen atoms to form a 5 to 10 member heterocycle,
  or $R_{63}$ and $R_{64}$ are taken together with the nitrogen atom to form a 3 to 10 member.

In a further embodiment, $R_3$ is methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl, any of which unsubstituted or substituted by one or more substituents chosen from halogen, nitro, $CONR_{63}R_{64}$, $C_{1-6}$ alkyl, $C_{2-6}$ alkenyl, $C_{1-6}$ alkyloxy, $C_{2-6}$ alkenyloxy, $C_{2-6}$ alkynyloxy, $C(O)C_{1-6}$ alkyl, $C_{6-12}$ aryl, 3-10 member heterocycle, 4-16 member heteroaralkyl, hydroxyl, $NR_{63}R_{64}$, $C(O)OR_{62}$, cyano, and azido;
  wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl,
  or $R_{63}$ and $R_{64}$ are taken together with the nitrogen atom to form a 3 to 10 member heterocycle.

In a further embodiment, $R_3$ is methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl, any of which unsubstituted or substituted by one or more substituents chosen from halogen, $C_{1-6}$ alkyl, $NR_{63}R_{64}$, nitro, $CONR_{63}R_{64}$, $C_{1-6}$ alkyloxy, $C(O)OR_{62}$, cyano, and azido;
  wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl,
  or $R_{63}$ and $R_{64}$ are taken together with the nitrogen atom to form a 3 to 10 member heterocycle.

In a further embodiment, $R_3$ is methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl, any of which unsubstituted or substituted by one or more substituents chosen from a halogen, $C_{1-6}$ alkyl, $C_{1-6}$ alkyloxy, $CF_3$, COOH, $COOC_{1-6}$ alkyl, cyano, $NH_2$, nitro, $NH(C_{1-6}$ alkyl), $N(C_{1-6}$ alkyl$)_2$ and 3-8 member heterocycle.

In a further embodiment, $R_3$ is chosen from methyl, ethyl, vinyl, propyl, propenyl, isopropyl, butyl, isobutyl, pentyl, neopentyl, or tert-butyl.

In a further embodiment, $R_3$ is unsubstituted methyl or methyl substituted by one or more halogens.

In a further embodiment, $R_3$ is unsubstituted methyl or methyl substituted by one or more fluoro.

In a further embodiment, $R_3$ is methyl, ethyl, vinyl, propyl, propenyl, isopropyl, butyl, isobutyl, pentyl, neopentyl, or tert-butyl.

In a further embodiment, $R_3$ is isopropyl or isobutyl.

According to a further aspect of the invention, $R_3$ is H.

According to a further aspect of the invention, $R_3$ is methyl.

According to a further aspect of the invention, $R_3$ is ethyl.

According to a further aspect of the invention, $R_3$ is isopropyl.

According to a further aspect of the invention, $R_3$ is isobutyl.

According to a further embodiment, the novel spirotropane compounds of formula are selected from the novel compounds represented by formula I':

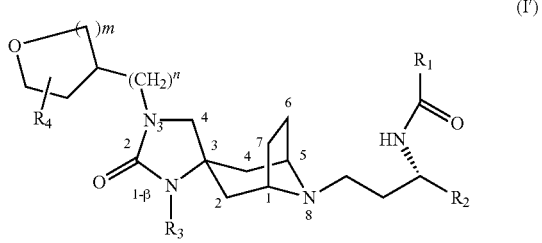

(I')

or pharmaceutically acceptable salts, hydrates or solvates thereof,
Wherein:
m is 1 or 2;
$R_4$ is H, or optionally substituted $C_{1-10}$ alkyl;
$R_1$, $R_2$, $R_3$, and n are as previously defined herein; and
provided that when $R_3$ is isopropyl then $R_1$ is not 4,4-difluorocyclohexyl.

According to another aspect of the invention, in formula I', when $R_3$ is isopropyl, then $R_1$ is not halogenated cyclohexyl.

According to another aspect of the invention, in formula I', when $R_3$ is unsubstituted $C_{2-4}$ alkyl, then $R_1$ is not halogenated cyclohexyl.

According to another aspect of the invention, in formula I', when $R_3$ is unsubstituted $C_{1-4}$ alkyl, then $R_1$ is not halogenated cyclohexyl.

According to a further embodiment, the present invention provides novel compounds represented by formula I' or pharmaceutically acceptable salts, hydrates or solvates thereof, wherein:
n is 0, 1 or 2;
m is 1 or 2;
$R_1$ is optionally substituted $C_{1-10}$ alkyl, optionally substituted $C_{2-10}$ alkenyl, or optionally substituted $C_{2-10}$ alkynyl;
$R_2$ is optionally substituted $C_{6-12}$ aryl;
$R_3$ is H, or optionally substituted $C_{1-10}$ alkyl;
$R_3$ is optionally substituted $C_{1-10}$ alkyl, optionally substituted $C_{2-10}$ alkenyl, or optionally substituted $C_{2-10}$ alkynyl;
$R_4$ is H, or optionally substituted $C_{1-10}$ alkyl; and
provided that when $R_3$ is isopropyl then $R_1$ is not 4,4-difluorocyclohexyl.

According to a further embodiment, the present invention provides novel compounds represented by formula I' or pharmaceutically acceptable salts, hydrates or solvates thereof, wherein:
n is 0, 1 or 2;
m is 1 or 2;
$R_1$ is optionally substituted $C_{1-10}$ alkyl, optionally substituted $C_{2-10}$ alkenyl, or optionally substituted $C_{2-10}$ alkynyl;
$R_2$ is optionally substituted $C_{6-12}$ aryl;
$R_3$ is H, or optionally substituted $C_{1-10}$ alkyl;
$R_3$ is optionally substituted $C_{1-10}$ alkyl, optionally substituted $C_{2-10}$ alkenyl, or optionally substituted $C_{2-10}$ alkynyl;
$R_4$ is H, or optionally substituted alkyl; and
provided that when $R_3$ is isopropyl, then $R_1$ is not halogenated cyclohexyl.

According to a further embodiment, the present invention provides novel compounds represented by formula I' or pharmaceutically acceptable salts, hydrates or solvates thereof, wherein:
n is 0, 1 or 2;
m is 1 or 2;
$R_1$ is optionally substituted $C_{1-10}$ alkyl, optionally substituted $C_{2-10}$ alkenyl, or optionally substituted $C_{2-10}$ alkynyl;
$R_2$ is optionally substituted $C_{6-12}$ aryl;
$R_3$ is H, or optionally substituted $C_{1-10}$ alkyl;
$R_3$ is optionally substituted $C_{1-10}$ alkyl, optionally substituted $C_{2-10}$ alkenyl, or optionally substituted $C_{2-10}$ alkynyl;
$R_4$ is H, or optionally substituted $C_{1-10}$ alkyl; and
provided that when $R_3$ is unsubstituted $C_{2-4}$ alkyl, then $R_1$ is not halogenated cyclohexyl.

According to a further embodiment, the present invention provides novel compounds represented by formula I' or pharmaceutically acceptable salts, hydrates or solvates thereof, wherein:
n is 0, 1 or 2;
m is 1 or 2;
$R_1$ is optionally substituted $C_{1-10}$ alkyl, optionally substituted $C_{2-10}$ alkenyl, or optionally substituted $C_{2-10}$ alkynyl;
$R_2$ is optionally substituted $C_{6-12}$ aryl;
$R_3$ is H, or optionally substituted $C_{1-10}$ alkyl;
$R_3$ is optionally substituted $C_{1-10}$ alkyl, optionally substituted $C_{2-10}$ alkenyl, or optionally substituted $C_{2-10}$ alkynyl;
$R_4$ is H, or optionally substituted $C_{1-10}$ alkyl; and
provided that when $R_3$ is unsubstituted $C_{1-4}$ alkyl, then $R_1$ is not halogenated cyclohexyl.

In a further embodiment, the present invention relates to intermediate compounds of formula (II)

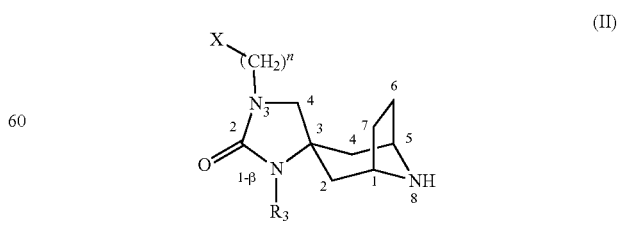

(II)

wherein X, n and $R_3$ are as defined herein, or pharmaceutically acceptable salts, hydrates, or solvates thereof.

According to a further embodiment, the present invention provides novel compounds represented by formula II, or pharmaceutically acceptable salts, hydrates or solvates thereof, wherein $R_3$ is $C_{1-4}$ alkyl (e.g., isopropyl), and n is 0 or 1.

According to a further embodiment, the present invention provides novel compounds represented by formula II, or pharmaceutically acceptable salts, hydrates or solvates thereof, wherein X—$(CH_2)_n$— is oxetanyl, tetrahydrofuranyl, furanyl, tetrahydropyranyl, dioxanyl, oxetanyl-$CH_2$—, tetrahydrofuran-$CH_2$—, furanyl-$CH_2$—, tetrahydropyranyl-$CH_2$—, or dioxanyl-$CH_2$— which in each case X is optionally substituted by $C_{1-4}$ alkyl.

According to a further embodiment, the present invention provides novel compounds represented by formula II, or pharmaceutically acceptable salts, hydrates or solvates thereof, wherein X—$(CH_2)_n$— is oxetanyl, tetrahydrofuranyl, furanyl, tetrahydropyranyl, dioxanyl, oxetanyl-$CH_2$—, tetrahydrofuran-$CH_2$—, furanyl-$CH_2$—, tetrahydropyranyl-$CH_2$—, or dioxanyl-$CH_2$— which in each case X is optionally substituted by $C_{1-4}$ alkyl, $R_3$ is $C_{1-4}$ alkyl (e.g., isopropyl), and n is 0 or 1.

According to a further embodiment, the present invention provides novel compounds represented by formula II, or pharmaceutically acceptable salts, hydrates or solvates thereof, wherein X—$(CH_2)_n$— is tetrahydrofuranyl, furanyl, tetrahydropyranyl, methyl-oxetanyl-$CH_2$—, tetrahydrofuran-$CH_2$—, tetrahydropyranyl-$CH_2$—, or methyl-dioxanyl-$CH_2$—.

According to a further embodiment, the present invention provides novel compounds represented by formula II, or pharmaceutically acceptable salts, hydrates or solvates thereof, wherein X—$(CH_2)_n$— is tetrahydrofuranyl, furanyl, tetrahydropyranyl, methyl-oxetanyl-$CH_2$—, tetrahydrofuran-$CH_2$—, tetrahydropyranyl-$CH_2$—, or methyl-dioxanyl-$CH_2$—, $R_3$ is $C_{1-4}$ alkyl (e.g., isopropyl), and n is 0 or 1.

According to another embodiment, the present invention provides intermediate compounds represented by formula (III), and pharmaceutically acceptable salts, hydrates or solvates thereof:

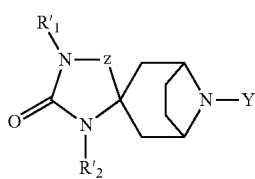

(III)

Wherein;
Z is C(O) or $CH_2$;
$R'_1$, or $R'_2$ are each, independently, H, optionally substituted $C_{1-10}$ alkyl, optionally substituted $C_{2-10}$ alkenyl, optionally substituted $C_{2-10}$ alkynyl, optionally substituted $C_{6-12}$ aryl, optionally substituted 3 to 10 membered heterocycle, optionally substituted $C_{7-12}$ aralkyl or optionally substituted heteroaralkyl (e.g., wherein the heteroaryl portion has 3 to 10 members and the alkyl portion has 1 to 6 carbon atoms), wherein at least one of $R'_1$ and $R'_2$ is other than H,;
Y is H or a nitrogen protecting group;
with the provisos that:
1) when Z is $CH_2$ or C(O), and $R'_1$ is methyl or ethyl, then $R'_2$ is other than isopropyl or ethyl;

2) when Z is C(O), and $R'_1$ is

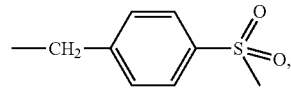

then $R'_2$ is other than H.

According to a further embodiment, in formula III, when $R'_1$ is $C_{1-3}$ alkyl, $R'_2$ is other than $C_{1-4}$ alkyl; and when Z is C(O) and $R'_1$ is benzyl substituted by —$SO_2H$ or —$SO_2$—$C_{1-2}$alkyl, then $R'_2$ is other than H or methyl.

According to a further embodiment, in formula III, when $R'_1$ is $C_{1-4}$ alkyl, $R'_2$ is other than $C_{1-4}$ alkyl; and when Z is C(O) and $R'_1$ is benzyl substituted by —$SO_2H$ or —$SO_2$—$C_{1-2}$alkyl, then $R'_2$ is other than H or $C_{1-2}$alkyl.

According to a further embodiment, in formula III, when $R'_1$ is $C_{1-4}$ alkyl, $R'_2$ is other than $C_{1-4}$ alkyl; and when Z is C(O) and $R'_1$ is benzyl or phenethyl substituted by —$SO_2H$ or —$SO_2$—$C_{1-2}$alkyl, then $R'_2$ is other than H or $C_{1-2}$alkyl.

According to a further embodiment, in formula III, when $R'_1$ is $C_{1-4}$ alkyl, $R'_2$ is other than $C_{1-5}$ alkyl; and when Z is C(O) and $R'_1$ is benzyl or phenethyl substituted by —$SO_2H$ or —$SO_2$—$C_{1-3}$alkyl, then $R'_2$ is other than H or $C_{1-2}$alkyl.

In one embodiment, $R'_1$ and/or $R'_2$ are each independently optionally substituted $C_{6-12}$ aryl, optionally substituted 3 to 10 membered heterocycle, optionally substituted $C_{7-12}$ aralkyl, or optionally substituted 4-16 member heteroaralkyl.

In a further embodiment, $R'_1$ and/or $R'_2$ are each independently optionally substituted $C_{6-12}$ aryl.

In a further embodiment, $R'_1$ and/or $R'_2$ are each independently optionally substituted 3 to 10 membered heterocycle.

In a further embodiment, $R'_1$ and/or $R'_2$ are each independently optionally substituted $C_{7-12}$ aralkyl.

In a further embodiment, $R'_1$ and/or $R'_2$ are each independently optionally substituted 4-16 member heteroaralkyl.

In a further embodiment, $R'_1$ and/or $R'_2$ are each independently $C_{6-12}$ aryl, $C_{7-12}$ aralkyl, 3 to 10 membered heterocycle, or 4-16 member heteroaralkyl, which in each case is unsubstituted or substituted by one or more substituents chosen from halogen, nitro, nitroso, $SO_3R'_{62}$, $PO_3R'_{65}R'_{66}$, $CONR'_{63}R'_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, oxo, oxime, $NR'_{63}R'_{64}$, $C(O)OR'_{62}$, cyano, azido, amidino and guanido;
  Wherein $R'_{62}$, $R'_{63}$, $R'_{64}$, $R'_{65}$ and $R'_{66}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl,
  or $R'_{65}$ and $R'_{66}$ are taken together with the oxygen atoms to form a 5 to 10 member heterocycle,
  or $R'_{63}$ and $R'_{64}$ are taken together with the nitrogen atom to form a 3 to 10 member heterocycle.

In a further embodiment, $R'_1$ and/or $R'_2$ are each independently $C_{6-12}$ aryl, $C_{7-12}$ aralkyl, 3 to 10 membered heterocycle or 4-16 member heteroaralkyl, which in each case is unsubstituted or substituted by one or more substituents chosen from halogen, $C_{1-6}$ alkyl, $NR'_{63}R'_{64}$, nitro, $CONR'_{63}R'_{64}$, $C_{1-6}$ alkyloxy, $C(O)OR'_{62}$, cyano, and azido;
  wherein $R'_{62}$, $R'_{63}$ and $R'_{64}$ are each independently chosen from H, $C_{1-12}$ alkyl, $C_{6-12}$ aryl, 3-10 member heterocycle, 4-16 member heteroaralkyl, and $C_{7-18}$ aralkyl,
  or $R'_{63}$ and $R'_{64}$ are taken together with the nitrogen atom to form a 3 to 10 member heterocycle.

In a further embodiment, $R'_1$ and/or $R'_2$ are each independently $C_{6-12}$ aryl, $C_{7-12}$ aralkyl, 3 to 10 membered heterocycle or 4-16 member heteroaralkyl, which in each case is unsubstituted or substituted by one or more substituents chosen from a halogen, $C_{1-6}$ alkyl, $C_{1-6}$ alkyloxy, $CF_3$, COOH, $COOC_{1-6}$ alkyl, cyano, $NH_2$, nitro, $NH(C_{1-6}$ alkyl), $N(C_{1-6}$ alkyl)$_2$ and 3-8 member heterocycle.

In a further embodiment, $R'_1$ and/or $R'_2$ are each independently phenyl or benzyl, which in each case is unsubstituted or substituted by one or more substituents chosen from halogen, nitro, $CONR'_{63}R'_{64}$, $C_{1-6}$ alkyl, $C_{2-6}$ alkenyl, $C_{1-6}$ alkyloxy, $C_{2-6}$ alkenyloxy, $C_{2-6}$ alkynyloxy, $C(O)C_{1-6}$ alkyl, $C_{6-12}$ aryl, 3-10 member heterocycle, 4-16 member heteroaralkyl, hydroxyl, $NR'_{63}R'_{64}$, $C(O)OR'_{62}$, cyano, and azido;
    wherein $R'_{62}$, $R'_{63}$ and $R'_{64}$ are each independently chosen from H, $C_{1-12}$ alkyl, $C_{6-12}$ aryl, 3-10 member heterocycle, 4-16 member heteroaralkyl, and $C_{7-18}$ aralkyl,
    or $R'_{63}$ and $R'_{64}$ are taken together with the nitrogen atom to form a 3 to 10 member heterocycle.

In a further embodiment, $R'_1$ and/or $R'_2$ are each independently phenyl or benzyl, which in each case is unsubstituted or substituted by one or more substituents chosen from halogen, $C_{1-6}$ alkyl, $NR'_{63}R'_{64}$, nitro, $CONR'_{63}R'_{64}$, $C_{1-6}$ alkyloxy, $C(O)OR'_{62}$, cyano, and azido;
    wherein $R'_{62}$, $R'_{63}$ and $R'_{64}$ are each independently chosen from H, $C_{1-12}$ alkyl, $C_{6-12}$ aryl, 3-10 member heterocycle, 4-16 member heteroaralkyl, and $C_{7-18}$ aralkyl,
    or $R'_{63}$ and $R'_{64}$ are taken together with the nitrogen atom to form a 3 to 10 member heterocycle.

In a further embodiment, $R'_1$ and/or $R'_2$ are each independently benzyl, which in each case is unsubstituted or substituted by one or more substituents chosen from halogen, $C_{1-6}$ alkyl, $NR'_{63}R'_{64}$, nitro, $CONR'_{63}R'_{64}$, $C_{1-6}$ alkyloxy, $C(O)OR'_{62}$, cyano, and azido;
    wherein $R'_{62}$, $R'_{63}$ and $R'_{64}$ are each independently chosen from H, $C_{1-12}$ alkyl, $C_{6-12}$ aryl, 3-10 member heterocycle, 4-16 member heteroaralkyl, and $C_{7-18}$ aralkyl,
    or $R'_{63}$ and $R'_{64}$ are taken together with the nitrogen atom to form a 3 to 10 member heterocycle.

In a further embodiment, $R'_1$ and/or $R'_2$ are each independently chosen from phenyl, benzyl, pyridinyl, thiophenyl, benzofuran, thiazole, and pyrazole, which in each case is unsubstituted or substituted by one or more substituents chosen from a halogen, $C_{1-6}$ alkyl, $C_{1-6}$ alkyloxy, $CF_3$, COOH, $COOC_{1-6}$ alkyl, cyano, $NH_2$, nitro, $NH(C_{1-6}$ alkyl), $N(C_{1-6}$ alkyl)$_2$ and a 3-8 member heterocycle.

In a further embodiment, $R'_1$ and/or $R'_2$ are each independently benzyl unsubstituted or substituted by one or more substituents chosen from halogen, $C_{1-3}$ alkoxy, $SO_2C_{1-3}$alkyl, difluoromethoxy, trifluoromethoxy, trifluoromethyl, CN and pyrazoyl.

In a further embodiment, $R'_1$ and/or $R'_2$ are each independently benzyl optionally substituted in the para (p) position.

In further embodiments:
$R'_1$ and/or $R'_2$ are each independently benzyl;
$R'_1$ and/or $R'_2$ are each independently benzyl substituted with a halogen;
$R'_1$ and/or $R'_2$ are each independently benzyl substituted with Br;
$R'_1$ and/or $R'_2$ are each independently benzyl substituted with F;
$R'_1$ and/or $R'_2$ are each independently benzyl substituted with Cl;
$R'_1$ and/or $R'_2$ are each independently benzyl substituted with at least one halogen;
$R'_1$ and/or $R'_2$ are each independently benzyl substituted with a $C_{1-3}$ alkoxy;
$R'_1$ and/or $R'_2$ are each independently benzyl substituted with methoxy;
$R'_1$ and/or $R'_2$ are each independently benzyl substituted with ethoxy;
$R'_1$ and/or $R'_2$ are each independently benzyl substituted with $SO_2C_{1-3}$alkyl;
$R'_1$ and/or $R'_2$ are each independently benzyl substituted with methanesulfonyl;
$R'_1$ and/or $R'_2$ are each independently benzyl substituted with difluoromethoxy;
$R'_1$ and/or $R'_2$ are each independently benzyl substituted with trifluoromethoxy;
$R'_1$ and/or $R'_2$ are each independently benzyl substituted with trifluoromethyl;
$R'_1$ and/or $R'_2$ are each independently benzyl substituted with CN;
$R'_1$ and/or $R'_2$ are each independently benzyl substituted with pyrrazoyl; or
$R'_1$ and/or $R'_2$ are each independently benzyl optionally substituted in the para (p) position.

In a further embodiment, $R'_1$ and/or $R'_2$ are each independently azetidinyl, dioxanyl, pyrrolidinyl, piperazinyl, piperidyl, piperidino, oxetanyl, tetrahydropyranyl, tetrahydrofuranyl, morpholinyl, $CH_2$-azetidinyl, $CH_2$-dioxanyl, $CH_2$-dioxolanyl, $CH_2$-pyrrolidinyl, $CH_2$-piperazinyl, $CH_2$-piperidyl, $CH_2$-oxetanyl, $CH_2$-tetrahydropyranyl, $CH_2$-tetrahydrofuranyl, or $CH_2$-morpholinyl, any of which can be unsubstituted or substituted by one or more substituents chosen from halogen, nitro, nitroso, $SO_3R'_{62}$, $PO_3R'_{65}R'_{66}$, $CONR'_{63}R'_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$alkyl, $C(O)C_{2-6}$alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, oxo, oxime, $NR'_{63}R'_{64}$, $C(O)OR'_{62}$, cyano, azido, amidino and guanido;
    wherein $R'_{62}$, $R'_{63}$, $R'_{64}$, $R'_{65}$ and $R'_{66}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl,
    or $R'_{65}$ and $R'_{66}$ are taken together with the oxygen atoms to form a 5 to 10 member heterocycle,
    or $R'_{63}$ and $R'_{64}$ are taken together with the nitrogen atom to form a 3 to 10 member heterocycle.

In a further embodiment, $R'_1$ and/or $R'_2$ are each independently azetidinyl, dioxanyl, pyrrolidinyl, piperazinyl, piperidyl, piperidino, oxetanyl, tetrahydropyranyl, tetrahydrofuranyl, morpholinyl, $CH_2$-azetidinyl, $CH_2$-dioxanyl, $CH_2$-dioxolanyl, $CH_2$-pyrrolidinyl, $CH_2$-piperazinyl, $CH_2$-piperidyl, $CH_2$-oxetanyl, $CH_2$-tetrahydropyranyl, $CH_2$-tetrahydrofuranyl, or $CH_2$-morpholinyl, any of which can be unsubstituted or substituted by one or more substituents chosen from halogen, $C_{1-6}$ alkyl, $NR'_{63}R'_{64}$, nitro, $CONR'_{63}R'_{64}$, $C_{1-6}$ alkyloxy, $C(O)OR'_{62}$, cyano, and azido;
    wherein $R'_{62}$, $R'_{63}$ and $R'_{64}$ are each independently chosen from H, $C_{1-12}$ alkyl, $C_{6-12}$ aryl, 3-10 member heterocycle, 4-16 member heteroaralkyl, and $C_{7-18}$ aralkyl,
    or $R'_{63}$ and $R'_{64}$ are taken together with the nitrogen atom to form a 3 to 10 member heterocycle.

In a further embodiment, $R'_1$ and/or $R'_2$ are each independently azetidinyl, dioxanyl, pyrrolidinyl, piperazinyl, piperidyl, piperidino, oxetanyl, tetrahydropyranyl, tetrahydrofuranyl, morpholinyl, $CH_2$-azetidinyl, $CH_2$-dioxanyl, $CH_2$-dioxolanyl, $CH_2$-pyrrolidinyl, $CH_2$-piperazinyl, $CH_2$-piperidyl, $CH_2$-oxetanyl, $CH_2$-tetrahydropyranyl, $CH_2$-tetrahydrofuranyl, or $CH_2$-morpholinyl, any of which can be unsubstituted or substituted by one or more substituents chosen from a halogen, $C_{1-6}$ alkyl, $C_{1-6}$ alkyloxy, $CF_3$, COOH, $COOC_{1-6}$ alkyl, cyano, $NH_2$, nitro, $NH(C_{1-6}$ alkyl), $N(C_{1-6}$ alkyl)$_2$ and a 3-8 member heterocycle.

In a further embodiment, $R'_1$ and/or $R'_2$ are each independently oxetanyl, tetrahydropyranyl, tetrahydrofuranyl, morpholinyl, $CH_2$-dioxanyl, $CH_2$-dioxolanyl, $CH_2$-oxetanyl, or $CH_2$-tetrahydropyranyl, $CH_2$-tetrahydrofuranyl, any of which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido.

In a further embodiment, $R'_1$ and/or $R'_2$ are each independently $CH_2$-dioxanyl, $CH_2$-dioxolanyl, $CH_2$-oxetanyl, $CH_2$-tetrahydropyranyl, or $CH_2$-tetrahydrofuranyl, any of which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido.

In a further embodiment, $R'_1$ and/or $R'_2$ are each independently optionally substituted $C_{1-10}$ alkyl (e.g., methyl, ethyl, isopropyl, isobutyl, cyclopropyl, cyclobutyl, tert-butyl, cyclopentyl, cyclohexyl, or cycloheptyl).

In a further embodiment, $R'_1$ and/or $R'_2$ are each independently $C_{1-10}$ alkyl optionally substituted.

In a further embodiment, $R'_1$ and/or $R'_2$ are each independently $C_{1-6}$ alkyl optionally substituted.

In a further embodiment, $R'_1$ and/or $R'_2$ are each independently $C_{3-12}$ cycloalkyl optionally substituted.

In a further embodiment, $R'_1$ and/or $R'_2$ are each independently $C_{3-10}$ cycloalkyl optionally substituted.

In a further embodiment, $R'_1$ and/or $R'_2$ are each independently $C_{5-7}$ cycloalkyl optionally substituted.

In a further embodiment, $R'_1$ and/or $R'_2$ are each independently optionally substituted $C_{6-7}$ cycloalkyl.

In a further embodiment, $R'_1$ and/or $R'_2$ are each independently optionally substituted $C_6$ cycloalkyl.

In a further embodiment, $R'_1$ and/or $R'_2$ are each independently methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl, any of which unsubstituted or substituted by one or more substituents chosen from halogen, nitro, nitroso, $SO_3R'_{62}$, $PO_3R'_{65}R'_{66}$, $CONR'_{63}R'_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, oxo, oxime, $NR'_{63}R'_{64}$, $C(O)OR'_{62}$, cyano, azido, amidino, and guanido;
wherein $R'_{62}$, $R'_{63}$, $R'_{64}$, $R'65$ and $R'_{66}$ are each independently chosen from H, $C_{1-10}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl,
or $R'_{65}$ and $R'_{66}$ are taken together with the oxygen atoms to form a 5 to 10 member heterocycle,
or $R'_{63}$ and $R'_{64}$ are taken together with the nitrogen atom to form a 3 to 10 member.

In a further embodiment, $R'_1$ and/or $R'_2$ are each independently methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl, any of which unsubstituted or substituted by one or more substituents chosen from halogen, nitro, $CONR'_{63}R'_{64}$, $C_{1-6}$ alkyl, $C_{2-6}$ alkenyl, $C_{1-6}$ alkyloxy, $C_{2-6}$ alkenyloxy, $C_{2-6}$ alkynyloxy, $C(O)C_{1-6}$ alkyl, $C_{6-12}$ aryl, 3-10 member heterocycle, 4-16 member heteroaralkyl, hydroxyl, $NR'_{63}R'_{64}$, $C(O)OR'_{62}$, cyano, and azido;
wherein $R'_{62}$, $R'_{63}$ and $R'_{64}$ are each independently chosen from H, $C_{1-12}$ alkyl, $C_{6-12}$ aryl, 3-10 member heterocycle, 4-16 member heteroaralkyl, and $C_{7-18}$ aralkyl;
or $R'_{63}$ and $R'_{64}$ are taken together with the nitrogen atom to form a 3 to 10 member heterocycle.

In a further embodiment, $R'_1$ and/or $R'_2$ are each independently methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl, any of which unsubstituted or substituted by one or more substituents chosen from halogen, $C_{1-6}$ alkyl, $NR'_{63}R'_{64}$, nitro, $CONR'_{63}R'_{64}$, $C_{1-6}$ alkyloxy, $C(O)OR'_{62}$, cyano, and azido;
wherein $R'_{62}$, $R'_{63}$ and $R'_{64}$ are each independently chosen from H, $C_{1-12}$ alkyl, $C_{6-12}$ aryl, 3-10 member heterocycle, 4-16 member heteroaralkyl, and $C_{7-18}$ aralkyl,
or $R'_{63}$ and $R'_{64}$ are taken together with the nitrogen atom to form a 3 to 10 member heterocycle.

In a further embodiment, $R'_1$ and/or $R'_2$ are each independently methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl, any of which unsubstituted or substituted by one or more substituents chosen from a halogen, $C_{1-6}$ alkyl, $C_{1-6}$ alkyloxy, $CF_3$, COOH, $COOC_{1-6}$ alkyl, cyano, $NH_2$, nitro, $NH(C_{1-6}$ alkyl), $N(C_{1-6}$ alkyl)$_2$ and 3-8 member heterocycle.

In a further embodiment, $R'_1$ and/or $R'_2$ are each independently chosen from methyl, ethyl, vinyl, propyl, propenyl, isopropyl, butyl, isobutyl, pentyl, neopentyl, or tert-butyl.

In a further embodiment, $R'_1$ and/or $R'_2$ are each independently unsubstituted methyl or methyl substituted by one or more halogens.

In a further embodiment, $R'_1$ and/or $R'_2$ are each independently unsubstituted methyl or methyl substituted by one or more fluoro.

In one embodiment, $R'_1$ and/or $R'_2$ are each independently chosen from H, optionally substituted alkyl or optionally substituted $C_{7-12}$ aralkyl.

In a further embodiment, $R'_1$ and/or $R'_2$ are each independently optionally substituted $C_{1-10}$ alkyl.

In a further embodiment, $R'_1$ and/or $R'_2$ are each independently optionally substituted $C_{7-12}$ aralkyl.

In a further embodiment, $R'_2$ is methyl, ethyl, vinyl, propyl, propenyl, isopropyl, butyl, isobutyl, pentyl, neopentyl, or tert-butyl.

In a further embodiment, $R'_2$ is isopropyl or isobutyl.

In a further embodiment, $R'_2$ is H.

In a further embodiment, $R'_2$ is methyl.

In a further embodiment, $R'_2$ is ethyl.

In a further embodiment, $R'_2$ is isopropyl.

In a further embodiment, $R'_2$ is isobutyl.

In a further embodiment, $R'_1$ is dioxanyl, oxetanyl, tetrahydropyranyl, tetrahydrofuranyl, morpholinyl, $CH_2$-dioxanyl, $CH_2$-dioxolanyl, $CH_2$-oxetanyl, $CH_2$-tetrahydropyranyl, or $CH_2$-tetrahydrofuranyl, any of which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido.

In a further embodiment, $R'_1$ is oxetanyl, tetrahydropyranyl, tetrahydrofuranyl, morpholinyl, $CH_2$-dioxanyl, $CH_2$-dioxolanyl, $CH_2$-oxetanyl, $CH_2$-tetrahydropyranyl, or $CH_2$-tetrahydrofuranyl, any of which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido; and $R'_2$ is isopropyl.

In a further embodiment, $R'_1$ is $CH_2$-dioxanyl, $CH_2$-dioxolanyl, $CH_2$-tetrahydropyranyl, or $CH_2$-tetrahydrofuranyl, any of which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido; and $R'_2$ is isopropyl.

In a further embodiment, $R'_1$ is $CH_2$-dioxanyl which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido; and $R'_2$ is isopropyl.

In a further embodiment, $R'_1$ is $CH_2$-dioxolanyl which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido; and $R'_2$ is isopropyl.

In a further embodiment, $R'_1$ is $CH_2$-tetrahydrofuranyl which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido; and $R'_2$ is isopropyl.

In a further embodiment, $R'_1$ is $CH_2$-tetrahydropyranyl which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido; and $R'_2$ is H.

In a further embodiment, $R'_1$ is $CH_2$-tetrahydropyranyl, which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido; and $R'_2$ is methyl.

In a further embodiment, $R'_1$ is $CH_2$-tetrahydropyranyl which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido; and $R'_2$ is ethyl.

In a further embodiment, $R'_1$ is $CH_2$-tetrahydropyranyl which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido; and $R'_2$ is isopropyl.

In a further embodiment, $R'_1$ is $CH_2$-tetrahydropyranyl which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido; and $R'_2$ is isobutyl.

In a further embodiment, $R'_1$ is $CH_2$-dioxanyl which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido; and $R'_2$ is isopropyl and Z is C(O).

In a further embodiment, $R'_1$ is $CH_2$-dioxanyl which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido; and $R'_2$ is isopropyl and Z is $CH_2$.

In a further embodiment, $R'_1$ is $CH_2$-dioxolanyl which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido; and $R'_2$ is isopropyl and Z is C(O).

In a further embodiment, $R'_1$ is $CH_2$-dioxolanyl which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido; and $R'_2$ is isopropyl and Z is $CH_2$.

In a further embodiment, $R'_1$ is $CH_2$-tetrahydrofuranyl which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido; $R'_2$ is isopropyl and Z is C(O).

In a further embodiment, $R'_1$ is $CH_2$-tetrahydrofuranyl which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido; $R'_2$ is isopropyl and Z is $CH_2$.

In a further embodiment, $R'_1$ is $CH_2$-tetrahydropyranyl which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido; $R'_2$ is isopropyl and Z is C(O).

In a further embodiment, $R'_1$ is $CH_2$-tetrahydropyranyl which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido; $R'_2$ is H and Z is $CH_2$.

In a further embodiment, $R'_1$ is $CH_2$-tetrahydropyranyl which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido; $R'_2$ is methyl and Z is $CH_2$.

In a further embodiment, $R'_1$ is $CH_2$-tetrahydropyranyl which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido; $R'_2$ is ethyl and Z is $CH_2$.

In a further embodiment, $R'_1$ is $CH_2$-tetrahydropyranyl which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido; $R'_2$ is isopropyl and Z is $CH_2$.

In a further embodiment, $R'_1$ is $CH_2$-tetrahydropyranyl which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido; $R'_2$ is isobutyl and Z is $CH_2$.

In a further embodiment, Z is CO.

In a further embodiment, Z is $CH_2$.

Y is H or an amino protecting group selected from the group consisting of t-butyloxycarbonyl (BOC), ethyloxycarbonyl, methyloxycarbonyl, trichloroethyloxycarbonyl, allyloxycarbonyl (Alloc), benzyloxycarbonyl (CBZ), allyl, benzyl (Bn), fluorenylmethylcarbonyl (Fmoc), acetyl, chloroacetyl, dichloroacetyl, trichloroacetyl, phenylacetyl, trifluoroacetyl, and benzoyl.

In a further embodiment, Y is H.

In a further embodiment, Y is benzyl, ethyloxycarbonyl, or tert-butoxycarbonyl (Boc).

According to a further embodiment, the present invention provides novel compounds represented by formula III wherein $R'_1$ is optionally substituted $C_{1-10}$ alkyl, optionally substituted $C_{6-12}$ aryl, optionally substituted 3 to 10 membered heterocycle, optionally substituted $C_{7-12}$ aralkyl, or optionally substituted 4-16 member heteroaralkyl, and $R'_2$ is $C_{1-4}$ alkyl (e.g., isopropyl), or pharmaceutically acceptable salts, hydrates or solvates thereof.

According to a further embodiment, the present invention provides novel compounds represented by formula III, or pharmaceutically acceptable salts, hydrates or solvates thereof, wherein $R'_1$ is $C_{1-4}$ alkyl optionally substituted by halogen, cyano, nitro, oxo, amino, $C_{1-4}$ alkoxy, COOH, COO—$C_{1-4}$ alkyl, CO—$C_{1-4}$ alkyl, or phenyl, phenyl which is optionally substituted by halogen, cyano, nitro, oxo, amino, $C_{1-4}$ alkyl, $C_{1-4}$ alkoxy, halogenated $C_{1-4}$ alkyl, halogenated $C_{1-4}$ alkoxy, COOH, COO—$C_{1-4}$ alkyl, CO—$C_{1-4}$ alkyl, $C_{1-4}$ alkyl-S—, halogenated $C_{1-4}$ alkyl-S—, benzyloxy, or pyrazolyl, pyrrolidinyl, oxetanyl, tetrahydrofuranyl, furanyl, thiophenyl, thiazolyl, imidazolyl, dioxolanyl, tetrahydropyranyl, or dioxanyl, which in each case is optionally substituted by halogen, cyano, nitro, oxo, amino, $C_{1-4}$ alkyl, $C_{1-4}$ alkoxy, halogenated $C_{1-4}$ alkyl, halogenated $C_{1-4}$ alkoxy, COOH, COO—$C_{1-4}$ alkyl, CO—$C_{1-4}$ alkyl, $C_{1-4}$ alkyl-S—, halogenated $C_{1-4}$ alkyl-S—, benzyloxy, or pyrazolyl, or pyrrolidinyl-$CH_2$—, oxetanyl-$CH_2$—, tetrahydrofuran-$CH_2$—, furanyl-$CH_2$—, thiophenyl-$CH_2$—, thiazolyl-$CH_2$—, imidazolyl-$CH_2$—, dioxolanyl-$CH_2$—, tetrahydropyranyl-$CH_2$—, or dioxanyl-$CH_2$—, which in each case is optionally substituted by halogen, cyano, nitro, oxo, amino, $C_{1-4}$ alkyl, $C_{1-4}$ alkoxy, halogenated $C_{1-4}$ alkyl, halogenated $C_{1-4}$ alkoxy, COOH, COO—$C_{1-4}$ alkyl, CO—$C_{1-4}$ alkyl, $C_{1-4}$ alkyl-S—, halogenated $C_{1-4}$ alkyl-S—, benzyloxy, or pyrazolyl; and $R'_2$ is $C_{1-4}$ alkyl (e.g., isopropyl).

According to a further embodiment, the present invention provides novel compounds represented by formula III, or pharmaceutically acceptable salts, hydrates or solvates thereof, wherein $R'_1$ is $C_{1-4}$ alkyl optionally substituted by halogen, amino, $C_{1-4}$ alkoxy, COOH, COO—$C_{1-4}$ alkyl, or CO—$C_{1-4}$ alkyl, phenyl which is optionally substituted by halogen, cyano, amino, $C_{1-4}$ alkyl, $C_{1-4}$ alkoxy, halogenated $C_{1-4}$ alkyl, halogenated $C_{1-4}$ alkoxy, COOH, COO—$C_{1-4}$ alkyl, or CO—$C_{1-4}$ alkyl, or pyrrolidinyl, oxetanyl, tetrahydrofuranyl, furanyl, tetrahydropyranyl, dioxanyl, oxetanyl-$CH_2$—, tetrahydrofuran-$CH_2$—, furanyl-$CH_2$—, thiophenyl-$CH_2$—, thiazolyl-$CH_2$—, imidazolyl-$CH_2$—, dioxolanyl-$CH_2$—, tetrahydropyranyl-$CH_2$—, or dioxanyl-$CH_2$—, which in each case is optionally substituted by $C_{1-4}$ alkyl, COOH, or COO—$C_{1-4}$ alkyl; and $R'_2$ is $C_{1-4}$ alkyl (e.g., isopropyl).

According to a further embodiment, the present invention provides novel compounds represented by formula III, or pharmaceutically acceptable salts, hydrates or solvates thereof, wherein Z is CO;

$R'_1$ is $C_{1-4}$ alkyl optionally substituted by halogen, amino, $C_{1-4}$ alkoxy, COOH, COO—$C_{1-4}$ alkyl, or CO—$C_{1-4}$ alkyl, phenyl which is optionally substituted by halogen, cyano, amino, $C_{1-4}$ alkyl, $C_{1-4}$ alkoxy, halogenated $C_{1-4}$ alkyl, halogenated $C_{1-4}$ alkoxy, COOH, COO—$C_{1-4}$ alkyl, or CO—$C_{1-4}$ alkyl, or pyrrolidinyl, tetrahydrofuranyl, tetrahydropyranyl, dioxanyl, oxetanyl-$CH_2$—, tetrahydrofuran-$CH_2$—, furanyl-$CH_2$—, thiophenyl-$CH_2$—, thiazolyl-$CH_2$—, imidazolyl-$CH_2$—, dioxolanyl-$CH_2$—, tetrahydropyranyl-$CH_2$—, or dioxanyl-$CH_2$—, which in each case is optionally substituted by $C_{1-4}$ alkyl, COOH, or COO—$C_{1-4}$ alkyl; and $R'_2$ is $C_{1-4}$ alkyl (e.g., isopropyl).

In a further embodiment of the intermediate compounds of formula III, the present invention provides a 1-β compound represented by formula III', and pharmaceutically acceptable salts, hydrates or solvates thereof:

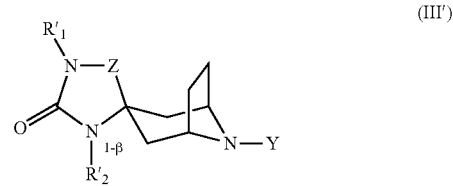

(III')

wherein $R'_1$, $R'_2$, Z and Y are as defined herein.

According to another embodiment, the present invention provides intermediate compounds represented by formula III", and pharmaceutically acceptable salts, hydrates or solvates thereof:

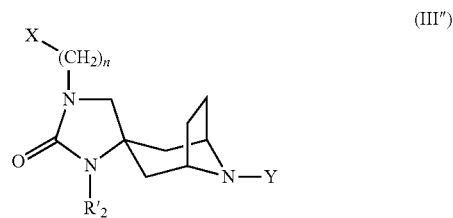

(III")

wherein;

X is an optionally substituted 4 to 7 membered ring comprising 1 or 2 oxygen atoms, provided that when X is a 4 membered ring it comprises only one oxygen atom;

n is 0, 1, or 2;

$R'_2$ is optionally substituted $C_{1-10}$ alkyl, optionally substituted $C_{2-10}$ alkenyl, or optionally substituted $C_{2-10}$ alkynyl; and Y is H or a nitrogen protecting group.

According to a further embodiment, the present invention provides novel compounds represented by formula III", or pharmaceutically acceptable salts, hydrates or solvates thereof, wherein $R'_2$ is H or $C_{1-4}$ alkyl (e.g., isopropyl).

According to a further embodiment, the present invention provides novel compounds represented by formula III", or pharmaceutically acceptable salts, hydrates or solvates thereof, wherein $R'_2$ is oxetanyl, tetrahydrofuranyl, furanyl, tetrahydropyranyl, dioxanyl, oxetanyl-$CH_2$—, tetrahydrofuran-$CH_2$—, furanyl-$CH_2$—, tetrahydropyranyl-$CH_2$—, or dioxanyl-$CH_2$— which in each case is optionally substituted by $C_{1-4}$ alkyl.

According to a further embodiment, the present invention provides novel compounds represented by formula III", or pharmaceutically acceptable salts, hydrates or solvates thereof, wherein X—$(CH_2)_n$— is oxetanyl, tetrahydrofuranyl, furanyl, tetrahydropyranyl, dioxanyl, oxetanyl-$CH_2$—, tetrahydrofuran-$CH_2$—, furanyl-$CH_2$—, tetrahydropyranyl-$CH_2$—, or dioxanyl-$CH_2$— which in each case is optionally substituted by $C_{1-4}$ alkyl, and $R'_2$ is H or $C_{1-4}$ alkyl (e.g., isopropyl).

According to a further embodiment, the present invention provides novel compounds represented by formula III", or pharmaceutically acceptable salts, hydrates or solvates thereof, wherein X—$(CH_2)_n$— is tetrahydrofuranyl, furanyl, tetrahydropyranyl, methyl-oxetanyl-$CH_2$—, tetrahydrofuran-$CH_2$—, tetrahydropyranyl-$CH_2$—, or methyl-dioxanyl-$CH_2$—.

According to a further embodiment, the present invention provides novel compounds represented by formula III", or pharmaceutically acceptable salts, hydrates or solvates thereof, wherein X—$(CH_2)_n$— is tetrahydrofuranyl, furanyl, tetrahydropyranyl, methyl-oxetanyl-CH$_2$—, tetrahydrofuran-CH$_2$—, tetrahydropyranyl-CH$_2$—, or methyl-dioxanyl-CH$_2$—, and R'$_2$ is H or C$_{1-4}$ alkyl (e.g., isopropyl).

In one embodiment, the compounds of the present invention are the (+) enantiomer having an enantiomeric excess of 99%.

In one embodiment, the compounds of the present invention are the (+) enantiomer having an enantiomeric excess of 95%.

In one embodiment, the compounds of the present invention are the (+) enantiomer having an enantiomeric excess of 90%.

In one embodiment, the compounds of the present invention are the (−) enantiomer having an enantiomeric excess of 99%.

In one embodiment, the compounds of the present invention are the (−) enantiomer having an enantiomeric excess of 95%.

In one embodiment, the compounds of the present invention are the (−) enantiomer having an enantiomeric excess of 90%.

Reference hereinafter to compounds of the general formula (I) includes the compounds and their pharmaceutically acceptable salts, hydrates and solvates.

In one embodiment, there is provided a method of modulating chemokine receptor activity in a subject comprising administering to the subject a therapeutically effective amount of a compound of formula (I) or composition of the invention.

In another embodiment, there is provided a method for the prevention or treatment of diseases associated with the modulation of chemokine receptor activity in a subject in need of such treatment comprising administering to the subject a therapeutically effective amount of a compound of formula (I) or composition of the invention.

The are numerous conditions and diseases for which a correlation with CCR5 or CCR5 chemokines has been established. It is expected that the compounds of formula I may be useful for the treatment of such conditions and diseases, and in particular, but not limited to, the following conditions and/or diseases: multiple sclerosis; Behcet's disease, Sjogren's syndrome or systemic sclerosis; arthritis, such as rheumatoid arthritis, spondyloarthropathies, gouty arthritis, osteoarthritis, systemic lupus erythematosus, and juvenile arthritis; and graft rejection, for example, solid organ transplants, such as heart, lung, liver, kidney and pancreas transplants (e.g. kidney and lung allografts), and graft versus host rejection; inflammatory bowel disease, including Crohn's disease and ulcerative colitis; inflammatory lung conditions; endometriosis; renal diseases, such as glomerular disease (e.g. glomerulonephritis); fibrosis, such as liver, pulmonary and renal fibrosis; encephalitis, such as HIV encephalitis; chronic heart failure; myocardial infarction; ischaemic heart disease; hypertension; stroke; obesity; restenosis; atherosclerotic plaque; psoriasis; atopic dermatitis; CNS diseases, such as AIDS related dementias and Alzheimer's disease; anaemia; chronic pancreatitis; type I diabetes; Hashimoto's thyroiditis; cancer, such as non-Hodgkin's lymphoma, Kaposi's sarcoma, melanoma, breast cancer and multiple myeloma; pain, such as nociceptive pain and neuropathic pain (e.g. peripheral neuropathic pain); and stress response resulting from surgery, infection, injury or other traumatic insult. Thus, according to another embodiment, there is provided a method for the treatment of any of the above-mentioned conditions and/or diseases in a subject in need of such treatment comprising administering to the subject a therapeutically effective amount of a compound of formula (I) or composition of the invention.

Infectious diseases where modulation of the CCR5 receptor is implicated include acute and chronic hepatitis B Virus (HBV) and hepatitis C Virus (HCV) infection; bubonic, septicemic, and pneumonic plague; pox virus infection, such as smallpox; toxoplasmosis infection; mycobacterium infection; trypanosomal infection such as Chagas' Disease; pneumonia; and cytosporidiosis. Thus, according to another embodiment, there is provided a method for the treatment of any of the above-mentioned infectious diseases in a subject in need of such treatment comprising administering to the subject a therapeutically effective amount of a compound of formula (I) or composition of the invention.

For a review of possible applications of chemokines and chemokine receptor blockers see Riberio and Horuk, "The Clinical Potential of Chemokine Receptor Antagonists", Pharmacology and Therapeutics 107 (2005) p 44-58.

In a further embodiment, there is provided a method for prevention or treatment of certain inflammatory diseases, immunoregulatory diseases, organ transplantation reactions and in the prevention and treatment of infectious diseases such as HIV infections in a subject in need of such treatment comprising administering to the subject a therapeutically effective amount of a compound of formula (I) or composition of the invention.

In a further embodiment, there is provided a method for treatment of inflammation in a subject in need of such treatment comprising administering to the subject a therapeutically effective amount of a compound of formula (I) or composition of the invention.

In another embodiment, there is provided a method for the prevention or treatment of diseases associated with the modulation of CCR5 chemokine receptor activity in a subject in need of such treatment comprising administering to the subject a therapeutically effective amount of a compound of formula (I) or composition of the invention.

In a further embodiment, there is provided a method for treatment of asthma in a subject in need of such treatment comprising administering to the subject a therapeutically effective amount of a compound of formula (I) or composition of the invention.

In a further embodiment, there is provided a method for treatment of rhinitis in a subject in need of such treatment comprising administering to the subject a therapeutically effective amount of a compound of formula (I) or composition of the invention.

In a further embodiment, there is provided a method for treatment of rheumatoid arthritis in a subject in need of such treatment comprising administering to the subject a therapeutically effective amount of a compound of formula (I) or composition of the invention.

In a further embodiment, there is provided a method for treatment of atherosclerosis in a subject in need of such treatment comprising administering to the subject a therapeutically effective amount of a compound of formula (I) or composition of the invention.

In still another aspect, there is provided a method for blocking cellular entry of HIV in a subject in need thereof comprising administering to the subject a therapeutically effective amount of a compound of formula (I) to block HIV from cellular entry in said subject.

In still another aspect, there is provided a method for prevention or treatment of HIV infections in a subject in need of such treatment comprising administering to the subject a therapeutically effective amount of a compound of formula (I) or composition of the invention.

In still another aspect, there is provided a method for delaying the onset of AIDS or treating AIDS in a subject in need of such treatment comprising administering to the subject a therapeutically effective amount of a compound of formula (I) or composition of the invention.

In a further embodiment, there is provided a method for the prevention or treatment of diseases associated with the modulation of chemokine receptor activity in a subject in need of such treatment comprising administering to the subject a pharmaceutical combination comprising at least one compound of formula (I) and at least one further therapeutic agent.

In a further embodiment, there is provided a method for the prevention or treatment of diseases associated with the modulation of CCR5 chemokine receptor activity in a subject in need of such treatment comprising administering to the subject a pharmaceutical combination comprising at least one compound of formula (I) and at least one further therapeutic agent.

In still another aspect, there is provided a method for blocking cellular entry of HIV in a subject or for the prevention or treatment of HIV infections in a subject in need of such treatment comprising administering to the subject a pharmaceutical combination comprising at least one compound of formula (I) and at least one further therapeutic agent.

In still another aspect, there is provided a method for delaying the onset of AIDS or treating AIDS in a subject in need of such treatment comprising administering to the subject a pharmaceutical combination comprising at least one compound of formula (I) and at least one further therapeutic agent.

In another embodiment, there is provided a combination useful for the prevention or treatment of diseases associated with the modulation of chemokine receptor activity which is a therapeutically effective amount of a compound of formula (I) and therapeutically effective amount of at least one further therapeutic agent.

In one embodiment, combinations of the present invention comprise those wherein the following embodiments are present, either independently or in combination.

In a further embodiment, the pharmaceutical combinations of this invention may contain at least one further therapeutic agent chosen from an agent used in inflammatory diseases, immunoregulatory diseases and in organ transplantation reactions.

In another embodiment, the pharmaceutical combination of this invention may contain at least one further therapeutic agent which is an antiviral agent.

In one embodiment, the pharmaceutical combination of this invention may contain at least one further antiviral agent which is chosen from nucleoside and nucleotide analog reverse transcriptase inhibitors, non-nucleoside reverse transcriptase inhibitors, protease inhibitors, attachment and fusion inhibitors, integrase inhibitors or maturation inhibitors.

In one embodiment, the pharmaceutical combinations of this invention may contain at least one other antiviral agent which is a nucleoside and nucleotide analog reverse transcriptase inhibitors chosen from 3TC (lamivudine, Epivir®), AZT (zidovudine, Retrovir®), Emtricitabine (Coviracil®, formerly FTC), d4T (2',3'-dideoxy-2',3'-didehydro-thymidine, stavudine and Zerit®), tenofovir (Viread®), 2',3'-dideoxyinosine (ddI, didanosine, Videx®), 2',3'-dideoxycytidine (ddC, zalcitabine, Hivid®), Combivir® (AZT/3TC or zidovudine/lamivudine combination), Trivizir® (AZT/3TC/ abacavir or zidovudine/lamivudine/abacavir combination), abacavir (1592U89, Ziagen®), SPD-754, ACH-126, 443 (Beta-L-Fd4C), Alovudine (MIV-310), DAPD (amdoxovir), Racivir, 9-[(2-hydroxymethyl)-1,3-dioxolan-4-yl]guanine or 2-amino-9-[(2-hydroxymethyl)-1,3-dioxolan-4-yl]adenine.

In another embodiment, the pharmaceutical combination of this invention may contain at least one other antiviral agent which is a non-nucleoside reverse transcriptase inhibitor chosen from Nevirapine (Viramune®, NVP, BI-RG-587), delavirdine (Rescriptor®, DLV), efavirenz (DMP 266, Sustiva®), (+)-Calanolide A, Capravirine (AG1549, formerly S-1153), DPC083, MIV-150, TMC120, TMC125, TMC-278 or BHAP (delavirdine), calanolides or L-697,661 (2-Pyridinone 3benzoxazolMeNH derivative).

In another embodiment, the pharmaceutical combination of this invention may contain at least one other antiviral agent which is a protease inhibitor chosen from nelfinavir (Viracept®, NFV), amprenavir (141W94, Agenerase®), indinavir (MK-639, IDV, Crixivan®), saquinavir (Invirase®, Fortovase®, SQV), ritonavir (Norvir®, RTV), lopinavir (ABT-378, Kaletra®), Atazanavir (BMS232632), mozenavir (DMP-450), fosamprenavir (GW433908), RO033-4649, Tipranavir (PNU-140690), TMC114, SPI-256 or VX-385.

In another embodiment, the pharmaceutical combination of this invention may contain at least one other antiviral agent which is an attachment and fusion inhibitor chosen from T-20 (enfuvirtide, Fuzeon®), T-1249, TRI-999, TRI-1144, Schering C (SCH-C), Schering D (SCH-D), FP21399, PRO-140, PRO 542, PRO 452, TNX-355, GW873140 (AK602), TAK-220, TAK-652, UK-427,857 or soluble CD4, CD4 fragments, CD4-hybrid molecules, BMS-806, BMS-488043, AMD3100, AMD070, AMD887, INCB9471, KRH-2731, KRH-3140 or KRH-3955.

In another embodiment, the pharmaceutical combination of this invention may contain at least one other antiviral agent which is an integrase inhibitor chosen from S-1360, L-870, 810, JKT 303, GS9137, L-870,812, MK-0518 or C-2507.

In another embodiment, the pharmaceutical combination of this invention may contain at least one other antiviral agent which is a maturation inhibitor and is PA-457.

In another embodiment, the pharmaceutical combination of this invention may contain at least one other antiviral agent which is a zinc finger inhibitor and is azodicarbonamide (ADA).

In another embodiment, the pharmaceutical combination of this invention may contain at least one other antiviral agent which is an antisense drug and is HGTV43.

In another embodiment, the pharmaceutical combination of this invention may contain at least one other antiviral agent which is an immunomodulator, immune stimulator or cytokine chosen from interleukin-2 (IL-2, Aldesleukin, Proleukin), granulocyte macrophage colony stimulating factor (GM-CSF), erythropoietin, Multikine, Ampligen, thymomodulin, thymopentin, foscarnet, HE2000, Reticulose, Murabutide, Resveratrol, HRG214, HIV-1 Immunogen (Remune) or EP HIV-1090.

In another embodiment, the pharmaceutical combination of this invention may contain at least one other antiviral agent chosen from 2',3'-dideoxyadenosine, 3'-deoxythymidine, 2',3'-dideoxy-2',3'-didehydrocytidine and ribavirin; acyclic nucleosides such as acyclovir, ganciclovir; interferons such as alpha-, beta- and gamma-interferon; glucuronation inhibitors such as probenecid; or TIBO drugs, HEPT, MAO derivatives.

The combinations referred to above may conveniently be presented for use in the form of a pharmaceutical formulation and thus pharmaceutical formulations comprising a combination as defined above together with a pharmaceutically acceptable carrier thereof comprises a further aspect of the invention.

The individual components of such combinations may be administered either sequentially or simultaneously in separate or combined pharmaceutical formulations.

The individual components of such combinations may be administered either sequentially or simultaneously in separate or combined pharmaceutical formulations.

In a further embodiment, the said compound of formula (I) and said therapeutic agent are administered sequentially.

In a further embodiment, the said compound of formula (I) and said therapeutic agent are administered simultaneously.

Thus, a further embodiment of the invention is a kit for use in administering a combinations, the kit comprising: a first containment means for storing a compound according to formula I in the form of a pharmaceutical formulation further comprising a pharmaceutically acceptable carrier; and a second containment means for storing at least one further therapeutic agent in the form of a pharmaceutical formulation further comprising a pharmaceutically acceptable carrier.

The subject to which the compounds are administered can be, for example, a mammal or a human. Preferably, the subject is a human.

In one embodiment, the present invention further provides a pharmaceutical composition comprising at least one compound having the formula (I) or pharmaceutically acceptable salts or pharmaceutically acceptable hydrates or pharmaceutically acceptable solvates thereof and at least one pharmaceutically acceptable carrier or excipient.

In another embodiment, the invention provides the use of a compound having the formula (I) for the manufacture of a medicament for prevention and treatment of diseases associated with the modulation of CCR5 chemokine receptor activity in a host comprising administering a therapeutically effective amount of a compound of formula (I).

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

The term "alkyl" represents a linear, branched or cyclic hydrocarbon moiety having, for example, 1 to 10 carbon atoms, which may have one or more double bonds or triple bonds in the chain, and is optionally substituted. For example, unless otherwise stated, suitable substituents include halogen, amino, amidino, amido, azido, cyano, guanido, hydroxyl, nitro, nitroso, urea, $OS(O)_2R_{21}$ (wherein $R_{21}$ is selected from $C_{1-6}$ alkyl, $C_{6-12}$ aryl or 3 to 10 membered heterocycle), $OS(O)_2OR_{22}$ (wherein $R_{22}$ is selected from H, $C_{1-6}$ alkyl, $C_{6-12}$ aryl or 3 to 10 membered heterocycle), $S(O)_2OR_{23}$ (wherein $R_{23}$ is selected from H, $C_{1-6}$ alkyl, $C_{6-12}$ aryl or 3 to 10 membered heterocycle), $S(O)_{0-2}R_{24}$ (wherein $R_{24}$ is selected from H, $C_{1-6}$ alkyl, $C_{6-12}$ aryl or 3 to 10 membered heterocycle), $OP(O)OR_{25}OR_{26}$, $P(O)OR_{25}OR_{26}$ (wherein $R_{25}$ and $R_{26}$ are each independently selected from H or $C_{1-6}$ alkyl), $C(O)R_{27}$ (wherein $R_{27}$ is selected from H, $C_{1-6}$ alkyl, $C_{6-12}$ aryl or 3 to 10 membered heterocycle), $C(O)OR_{28}$ (wherein $R_{28}$ is selected from H, $C_{1-6}$ alkyl, $C_{6-12}$ aryl, $C_{6-12}$ aralkyl (e.g. $C_{7-12}$ aralkyl) or 3 to 10 membered heterocycle), $NR_{29}C(O)R_{30}$, $NR_{29}C(O)OR_{30}$, $NR_{31}C(O)NR_{29}R_{30}$, $C(O)NR_{29}R_{30}$, $OC(O)NR_{29}R_{30}$ (wherein $R_{29}$, $R_{30}$ and $R_{31}$ are each independently selected from H, $C_{1-6}$ alkyl, $C_{6-12}$ aryl, $C_{6-12}$ aralkyl (e.g. $C_{7-12}$ aralkyl) or 3 to 10 membered heterocycle, or $R_{29}$ and $R_{30}$ are taken together with the atoms to which they are attached to form a 3 to 10 membered heterocycle), $SO_2NR_{32}R_{33}$, $NR_{32}SO_2R_{33}$ (wherein $R_{32}$ and $R_{33}$ are each independently selected from the group consisting of H, $C_{1-6}$ alkyl, $C_{6-12}$ aryl, 3 to 10 membered heterocycle and $C_{6-12}$ aralkyl (e.g. $C_{7-12}$ aralkyl)), $C(R_{34})NR_{35}$ or $C(R_{34})NOR_{35}$ (wherein $R_{34}$ and $R_{35}$ are each independently selected from the group consisting of H, $C_{1-6}$ alkyl, or $C_{6-12}$ aryl).

Preferred substituents for the alkyl groups include halogen (Br, Cl, I or F), cyano, nitro, oxo, amino, COOH, COO—$C_{1-4}$ alkyl, CO—$C_{1-4}$ alkyl, and phenyl.

Examples of alkyl groups include but are not limited to methyl, ethyl, propyl, isopropyl, butyl, isobutyl, sec-butyl, tert-butyl, pentyl, isopentyl, neopentyl, tert-pentyl, hexyl, isohexyl, neohexyl, allyl, vinyl, acetylenyl, ethylenyl, propenyl, isopropenyl butenyl, isobutenyl, hexenyl, butadienyl, pentenyl, pentadienyl, hexenyl, hexadienyl, hexatrienyl, heptenyl, heptadienyl, heptatrienyl, octenyl, octadienyl, octatrienyl, octatetraenyl, propynyl, butynyl, pentynyl, hexynyl, cyclopropyl, cyclobutyl, cycloheptyl, cyclohexenyl, cyclohex-dienyl and cyclohexyl.

The term alkyl is also meant to include alkyls in which one or more hydrogen atom is replaced by a halogen, i.e. an alkylhalide. Examples include but are not limited to trifluoromethyl, difluoromethyl, fluoromethyl, trichloromethyl, dichloromethyl, chloromethyl, trifluoroethyl, difluoroethyl, fluoroethyl, trichloroethyl, dichloroethyl, chloroethyl, chlorofluoromethyl, chlorodifluoromethyl, dichlorofluoroethyl.

The term "alkenyl" refers to alkyl groups may have one or more double bonds in the chain. The term "alkynyl" refers to alkyl groups may have one or more triple bonds in their chain. The alkenyl and alkynyl groups can be optionally substituted as described above for the alkyl groups.

The term "alkoxy" represents an alkyl which is covalently bonded to the adjacent atom through an oxygen atom. Examples include but are not limited to methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy and neohexyloxy.

The term "alkylamino" represents an alkyl which is covalently bonded to the adjacent atom through a nitrogen atom and may be monoalkylamino or dialkylamino, wherein the alkyl groups may be the same or different. Examples include but are not limited to methylamino, dimethylamino, ethylamino, diethylamino, methylethylamino, propylamino, isopropylamino, butylamino, isobutylamino, sec-butylamino, test-butylamino, pentylamino, isopentylamino, neopentylamino, tert-pentylamino, hexylamino, isohexylamino and neohexylamino.

The term "alkyloxycarbonyl" represents an alkyloxy which is covalently bonded to the adjacent atom through carbonyl (C=O). Examples include but are not limited to methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, tert-pentyloxycarbonyl, hexyloxycarbonyl, isohexyloxycarbonyl and neohexyloxycarbonyl.

The term "amidino" represents —C(=$NR_{10}$)$NR_{11}R_{12}$, wherein $R_{10}$, $R_{11}$ and $R_{12}$ are each independently selected from H, $C_{1-6}$ alkyl, $C_{6-12}$ aryl or $C_{6-12}$ aralkyl (e.g. $C_{7-12}$ aralkyl), or $R_{11}$ and $R_{12}$ are taken together with the nitrogen to which they are attached to form a 3 to 10 membered heterocycle.

The term "amido" represents —$CONH_2$, —$CONHR_{13}$ and —$CONR_{13}R_{14}$ wherein $R_{13}$ and $R_{14}$ are each independently selected from $C_{1-6}$ alkyl, $C_{6-12}$ aryl, 3 to 10 membered heterocycle or $C_{6-12}$ aralkyl (e.g. $C_{7-12}$ aralkyl), or $R_{13}$ and $R_{14}$ are taken together with the nitrogen to which they are attached to form a 3 to 10 membered heterocycle.

The term "amino" represents a derivative of ammonia obtained by substituting one or more hydrogen atom and include —$NH_2$, —$NHR_{15}$ and —$NR_{15}R_{16}$, wherein $R_{15}$ and $R_{16}$ are each independently selected from $C_{1-6}$ alkyl, $C_{6-12}$ aryl or $C_{6-12}$ aralkyl (e.g. $C_{7-12}$ aralkyl), or $R_{15}$ and $R_{16}$ are taken together with the nitrogen to which they are attached to form a 3 to 10 membered heterocycle.

The term "aryl" represents a carbocyclic moiety containing at least one benzenoid-type ring (i.e. the aryl group may be monocyclic or polycyclic), and which is optionally substituted with one or more substituents. For example, unless otherwise stated, suitable substituents include halogen, halogenated $C_{1-6}$ alkyl, halogenated $C_{1-6}$ alkoxy, amino, amidino, amido, azido, cyano, guanido, hydroxyl, nitro, nitroso, urea, $OS(O)_2R_{21}$ (wherein $R_{21}$ is selected from $C_{1-6}$ alkyl, $C_{6-12}$ aryl or 3 to 10 membered heterocycle), $OS(O)_2OR_{22}$ (wherein $R_{22}$ is selected from H, $C_{1-6}$ alkyl, $C_{6-12}$ aryl or 3 to 10 membered heterocycle), $S(O)_2OR_{23}$ (wherein $R_{23}$ is selected from H, $C_{1-6}$ alkyl, $C_{6-12}$ aryl or 3 to 10 membered heterocycle), $S(O)_{0-2}R_{24}$ (wherein $R_{24}$ is selected from H, $C_{1-6}$ alkyl, $C_{6-12}$ aryl or 3 to 10 membered heterocycle), $OP(O)OR_{25}OR_{26}$, $P(O)OR_{25}OR_{26}$ (wherein $R_{25}$ and $R_{26}$ are each independently selected from H or $C_{1-6}$ alkyl), $C_{1-6}$alkyl, $C_{6-12}$ aralkyl (e.g. $C_{7-12}$ aralkyl), $C_{1-6}$alkoxy, $C_{6-12}$ aralkyloxy (e.g. $C_{7-12}$ aralkyloxy), $C_{6-12}$aryloxy, 3 to 10 membered heterocycle, $C(O)R_{27}$ (wherein $R_{27}$ is selected from H, $C_{1-6}$ alkyl, $C_{6-12}$ aryl or 3 to 10 membered heterocycle), $C(O)OR_{28}$ (wherein $R_{28}$ is selected from H, $C_{1-6}$ alkyl, $C_{6-12}$ aryl, $C_{6-12}$ aralkyl (e.g. $C_{7-12}$ aralkyl) or 3 to 10 membered heterocycle), $NR_{29}C(O)R_{30}$, $NR_{29}C(O)OR_{30}$, $NR_{31}C(C)NR_{29}R_{30}$, $C(O)NR_{29}R_{30}$, $OC(O)NR_{29}R_{30}$ (wherein $R_{29}$, $R_{30}$ and $R_{31}$ are each independently selected from H, $C_{1-6}$ alkyl, $C_{6-12}$ aryl, $C_{6-12}$ aralkyl (e.g. $C_{7-12}$ aralkyl) or 3 to 10 membered heterocycle, or $R_{29}$ and $R_{30}$ are taken together with the atoms to which they are attached to form a 3 to 10 membered heterocycle), $SO_2NR_{32}R_{33}$, $NR_{32}SO_2R_{33}$ (wherein $R_{32}$ and $R_{33}$ are each independently selected from the group consisting of H, $C_{1-6}$ alkyl, $C_{6-12}$ aryl, 3 to 10 membered heterocycle and $C_{6-12}$ aralkyl (e.g. $C_{7-12}$ aralkyl)) $C(R_{34})NR_{35}$ or $C(R_{34})NOR_{35}$ (wherein $R_{34}$ and $R_{35}$ are each independently selected from the group consisting of H, $C_{1-6}$ alkyl, or $C_{6-12}$ aryl).

Preferred substituents for the aryl groups include halogen (Br, Cl, I or F), cyano, nitro, oxo, amino, $C_{1-4}$ alkyl (e.g., $CH_3$, $C_2H_5$, isopropyl), $C_{1-4}$ alkoxy (e.g., $OCH_3$, $OC_2H_5$), halogenated $C_{1-4}$ alkyl (e.g., $CF_3$, $CHF_2$), halogenated $C_{1-4}$ alkoxy (e.g., $OCF_3$, $OC_2F_5$), COOH, COO—$C_{1-4}$ alkyl, CO—$C_{1-4}$ alkyl, $C_{1-4}$ alkyl-S— (e.g., $CH_3S$, $C_2H_5S$), halogenated $C_{1-4}$ alkyl-S— (e.g., $CF_3S$, $C_2F_5S$), benzyloxy, and pyrazolyl.

Examples of aryl include but are not limited to phenyl, tolyl, dimethylphenyl, aminophenyl, anilinyl, naphthyl, anthryl, phenanthryl or biphenyl.

The term "aralkyl" represents an aryl group attached to the adjacent atom by a $C_{1-6}$alkyl. Examples include but are not limited to benzyl, benzhydryl, trityl, phenethyl, 3-phenylpropyl, 2-phenylpropyl, 4-phenylbutyl and naphthylmethyl. The aryl and alkyl portions can be optionally substituted as described above.

The term "aralkyloxy" represents an aralkyl which is covalently bonded to the adjacent atom through an oxygen atom. Examples include but are not limited to benzyloxy, benzhydryloxy, trityloxy, phenethyloxy, 3-phenylpropyloxy, 2-phenylpropyloxy, 4-phenylbutyloxy and naphthylmethoxy. The aryl and alkyl portions can be optionally substituted as described above.

The term "aryloxy" represents an aryl which is covalently bonded to the adjacent atom through an oxygen atom. Examples include but are not limited to phenoxy and naphthyloxy. The aryl portion can be optionally substituted as described above.

There is also provided "enantiomers" and "diastereoisomers" of the present invention. It will be appreciated that the compounds in accordance with the present invention can contain one or more chiral centers. The compounds in accordance with the present invention may thus exist in the form of two different optical isomers, that is (+) or (−) enantiomers or in the form of different diastereomers. All such enantiomers, diastereomers and mixtures thereof, including racemic or other ratio mixtures of individual enantiomers and diastereomers, are included within the scope of the invention. The single diastereomer can be obtained by methods well known to those of ordinary skill in the art, such as HPLC, crystallization and chromatography. The single enantiomer can be obtained by methods well known to those of ordinary skill in the art, such as chiral HPLC, enzymatic resolution and chiral auxiliary derivatization.

The optical purity is numerically equivalent to the "enantiomeric excess". The term "enantiomeric excess" is defined in percentage (%) value as follows: [mole fraction (major enantiomer)−mole fraction (minor enantiomer)]×100. An example of enantiomeric excess of 99% represents a ratio of 99.5% of one enantiomer and 0.5% of the opposite enantiomer.

The term "guanido" or "guanidino" represents —$NR_{17}C$(=$NR_{18}$)$NR_{19}R_{20}$ wherein $R_{17}$, $R_{18}$, $R_{19}$, and $R_{20}$ are each independently selected from H, $C_{1-6}$ alkyl, $C_{6-12}$ aryl or $C_{6-12}$ aralkyl (e.g. $C_{7-12}$ aralkyl), or $R_{19}$ and $R_{20}$ are taken together with the nitrogen to which they are attached to form a 3 to 10 membered heterocycle.

The term "halogen" is specifically a fluoride atom, chloride atom, bromide atom or iodide atom.

The term "heterocycle" represents an optionally substituted saturated, unsaturated or aromatic cyclic moiety wherein said cyclic moiety is interrupted by at least one heteroatom selected from oxygen (O), sulfur (S) or nitrogen (N). Heterocycles may be monocyclic or polycyclic rings. For example, unless otherwise stated, suitable substituents include halogen, halogenated $C_{1-6}$ alkyl, halogenated $C_{1-6}$ alkoxy, amino, amidino, amido, amido, cyano, guanido, hydroxyl, nitro, nitroso, urea, $OS(O)_2R_{21}$ (wherein $R_{21}$ is selected from $C_{1-6}$ alkyl, $C_{6-12}$ aryl or 3 to 10 membered heterocycle), $OS(O)_2OR_{22}$ (wherein $R_{22}$ is selected from H, $C_{1-6}$ alkyl, $C_{6-12}$ aryl or 3 to 10 membered heterocycle), $S(O)_2OR_{23}$ (wherein $R_{23}$ is selected from H, $C_{1-6}$ alkyl, $C_{6-12}$ aryl or 3 to 10 membered heterocycle), $S(O)_{0-2}R_{24}$ (wherein $R_{24}$ is selected from H, $C_{1-6}$ alkyl, $C_{6-12}$ aryl or 3 to 10 membered heterocycle), $OP(O)OR_{25}OR_{26}$, $P(O)OR_{25}OR_{26}$ (wherein $R_{25}$ and $R_{26}$ are each independently selected from H or $C_{1-6}$ alkyl), $C_{1-6}$alkyl, $C_{6-12}$ aralkyl (e.g. $C_{7-12}$ aralkyl), $C_{1-6}$alkoxy, $C_{6-12}$ aryl, $C_{6-12}$ aralkyloxy (e.g. $C_{7-12}$ aralkyloxy), $C_{6-12}$aryloxy, $C(O)R_{27}$ (wherein $R_{27}$ is selected from H, $C_{1-6}$ alkyl, $C_{6-12}$ aryl or 3 to 10 membered heterocycle), $C(O)OR_{28}$ (wherein $R_{28}$ is selected from H, $C_{1-6}$ alkyl, $C_{6-12}$ aryl, $C_{6-12}$ aralkyl (e.g. $C_{7-12}$ aralkyl) or 3 to 10 membered heterocycle), $NR_{29}C(O)R_{30}$, $NR_{29}C(O)OR_{30}$, $NR_{31}C(O)NR_{29}R_{30}$, $C(O)NR_{29}R_{30}$, $OC(O)NR_{29}R_{30}$ (wherein $R_{29}$, $R_{30}$ and $R_{31}$ are each independently selected from H, $C_{1-6}$ alkyl, $C_{6-12}$ aryl, $C_{6-12}$ aralkyl (e.g. $C_{7-12}$ aralkyl) or 3 to 10 membered heterocycle, or $R_{29}$ and $R_{30}$ are taken together with the atoms to which they are attached to form a 3 to 10 membered heterocycle), $SO_2NR_{32}R_{33}$, $NR_{32}SO_2R_{33}$ (wherein $R_{32}$ and $R_{33}$ are each independently selected from the group consisting of H, $C_{1-6}$ alkyl, $C_{6-12}$ aryl, 3 to 10 membered heterocycle and $C_{6-12}$ aralkyl (e.g. $C_{7-12}$ aralkyl)), $C(R_{34})NR_{35}$ or $C(R_{34})NOR_{35}$ (wherein $R_{34}$ and $R_{35}$ are each independently selected from the group consisting of H, $C_{1-6}$ alkyl, or $C_{6-12}$ aryl).

Preferred substituents for the heterocycle groups include halogen (Br, Cl, I or F), cyano, nitro, oxo, amino, $C_{1-4}$ alkyl (e.g., $CH_3$, $C_2H_5$, isopropyl), $C_{1-4}$ alkoxy (e.g., $OCH_3$, $OC_2H_5$), halogenated $C_{1-4}$ alkyl (e.g., $CF_3$, $CHF_2$), halogenated $C_{1-4}$ alkoxy (e.g., $OCF_3$, $OC_2F_5$), COOH, COO—$C_{1-4}$ alkyl, CO—$C_{1-4}$ alkyl, $C_{1-4}$ alkyl-S— (e.g., $CH_3S$, $C_2H_5S$), halogenated $C_{1-4}$ alkyl-S— (e.g., $CF_3S$, $C_2F_5S$), benzyloxy, and pyrazolyl.

Examples of heterocycles include but are not limited to azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, morpholino, oxetanyl, oxadiazolyl, oxiranyl, oxazinyl, oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazinyl, thiadiazolyl, triazolyl, thiazolyl, thienyl, tetrazinyl, thiadiazinyl, triazinyl, thiazinyl, thiopyranyl furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl.

The term "heteroaralkyl" represents a heterocycle group attached to the adjacent atom by a $C_{1-6}$ alkyl. The heterocycle and alkyl portions can be optionally substituted as described above.

The term "4 to 7 membered ring comprising 1 or 2 oxygen" represents an optionally substituted saturated, unsaturated or aromatic cyclic moiety wherein said cyclic moiety is interrupted by at least one oxygen (O). For example, unless otherwise stated, suitable substituents include halogen, halogenated $C_{1-6}$ alkyl, halogenated $C_{1-6}$ alkoxy, amino, amidino, amido, azido, cyano, guanido, hydroxyl, nitro, nitroso, urea, $OS(O)_2R_{21}$ (wherein $R_{21}$ is selected from $C_{1-6}$ alkyl, $C_{6-12}$ aryl or 3 to 10 membered heterocycle), $OS(O)_2OR_{22}$ (wherein $R_{22}$ is selected from H, $C_{1-6}$ alkyl, $C_{6-12}$ aryl or 3 to 10 membered heterocycle), $S(O)_2OR_{23}$ (wherein $R_{23}$ is selected from H, $C_{1-6}$ alkyl, $C_{6-12}$ aryl or 3 to 10 membered heterocycle), $S(O)_{0-2}R_{24}$ (wherein $R_{24}$ is selected from H, $C_{1-6}$ alkyl, $C_{6-12}$ aryl or 3 to 10 membered heterocycle), $OP(O)OR_{25}OR_{26}$, $P(O)OR_{25}OR_{26}$ (wherein $R_{25}$ and $R_{26}$ are each independently selected from H or $C_{1-6}$ alkyl), $C_{1-6}$alkyl, $C_{6-12}$ aralkyl (e.g. $C_{7-12}$ aralkyl), $C_{1-6}$alkoxy, $C_{6-12}$ aryl, $C_{6-12}$ aralkyloxy (e.g. $C_{7-12}$ aralkyloxy), $C_{6-12}$arylyloxy, $C(O)R_{27}$ (wherein $R_{27}$ is selected from H, $C_{1-6}$ alkyl, $C_{6-12}$ aryl or 3 to 10 membered heterocycle), $C(O)OR_{28}$ (wherein $R_{28}$ is selected from H, $C_{1-6}$ alkyl, $C_{6-12}$ aryl, $C_{6-12}$ aralkyl (e.g. $C_{7-12}$ aralkyl) or 3 to 10 membered heterocycle), $NR_{29}C(O)R_{30}$, $NR_{31}C(O)NR_{29}R_{30}$, $C(O)NR_{29}R_{30}$, $OC(O)NR_{29}R_{30}$ (wherein $R_{29}$, $R_{30}$ and $R_{31}$ are each independently selected from H, $C_{1-6}$ alkyl, $C_{6-12}$ aryl, $C_{6-12}$ aralkyl (e.g. $C_{7-12}$ aralkyl) or 3 to 10 membered heterocycle, or $R_{29}$ and $R_{30}$ are taken together with the atoms to which they are attached to form a 3 to 10 membered heterocycle), $SO_2NR_{32}R_{33}$, $NR_{32}SO_2R_{33}$ (wherein $R_{32}$ and $R_{33}$ are each independently selected from the group consisting of H, $C_{1-6}$ alkyl, $C_{6-12}$ aryl, 3 to 10 membered heterocycle and $C_{6-12}$ aralkyl (e.g. $C_{7-12}$ aralkyl)), $C(R_{34})NR_{35}$ or $C(R_{34})NOR_{35}$ (wherein $R_{34}$ and $R_{35}$ are each independently selected from the group consisting of H, $C_{1-6}$ alkyl, or $C_{6-12}$ aryl).

Preferred substituents for the 4 to 7 membered ring comprising 1 or 2 oxygen include halogen (Br, Cl, I or F), cyano, nitro, oxo, amino, $C_{1-4}$ alkyl (e.g., $CH_3$, $C_2H_5$, isopropyl), $C_{1-4}$ alkoxy (e.g., $OCH_3$, $OC_2H_5$), halogenated $C_{1-4}$ alkyl (e.g., $CF_3$, $CHF_2$), halogenated $C_{1-4}$ alkoxy (e.g., $OCF_3$, $OC_2F_5$), COOH, COO—$C_{1-4}$ alkyl, CO—$C_{1-4}$ alkyl, $C_{1-4}$ alkyl-S— (e.g., $CH_3S$, $C_2H_5S$), halogenated $C_{1-4}$ alkyl-S— (e.g., $CF_3S$, $C_2F_5S$), benzyloxy, and pyrazolyl.

Examples of 4 to 7 membered ring comprising 1 or 2 oxygen include but are not limited to oxetanyl, furanyl, tetrahydrofuranyl, pyranyl, tetrahydropyranyl, oxepanyl, oxepinyl, dioxolanyl, dioxanyl, dioxepinyl and dioxepanyl.

The term "independently" means that a substituent can be the same or a different definition for each item.

Unless otherwise stated, the term "optionally substituted" represents one or more halogen, halogenated $C_{1-6}$ alkyl, halogenated $C_{1-6}$ alkoxy, amino, amidino, amido, azido, cyano, guanido, hydroxyl, nitro, nitroso, urea, $OS(O)_2R_{21}$ (wherein $R_{21}$ is selected from $C_{1-6}$ alkyl, $C_{6-12}$ aryl or 3 to 10 membered heterocycle), $OS(O)_2OR_{22}$ (wherein $R_{22}$ is selected from H, $C_{1-6}$ alkyl, $C_{6-12}$ aryl or 3 to 10 membered heterocycle), $S(O)_2OR_{23}$ (wherein $R_{23}$ is selected from H, $C_{1-6}$ alkyl, $C_{6-12}$ aryl or 3 to 10 membered heterocycle), $S(O)_{0-2}R_{24}$ (wherein $R_{24}$ is selected from H, $C_{1-6}$ alkyl, $C_{6-12}$ aryl or 3 to 10 membered heterocycle), $OP(O)OR_{25}OR_{26}$, $P(O)OR_{25}OR_{26}$ (wherein $R_{25}$ and $R_{26}$ are each independently selected from H or $C_{1-6}$ alkyl), $C_{1-6}$alkyl, $C_{6-12}$ aralkyl (e.g. $C_{7-12}$ aralkyl), $C_{6-12}$ aryl, $C_{1-6}$ alkoxy, $C_{6-12}$ aralkyloxy (e.g. $C_{7-12}$ aralkyloxy), $C_{6-12}$ aryloxy, 3 to 10 membered heterocycle, $C(O)R_{27}$ (wherein $R_{27}$ is selected from H, $C_{1-6}$ alkyl, $C_{6-12}$ aryl or 3 to 10 membered heterocycle), $C(O)OR_{28}$ (wherein $R_{26}$ is selected from H, $C_{1-6}$ alkyl, $C_{6-12}$ aryl, $C_{6-12}$ aralkyl (e.g. $C_{7-12}$ aralkyl) or 3 to 10 membered heterocycle), $NR_{29}C(O)R_{30}$, $NR_{29}C(O)OR_{30}$, $NR_{31}C(O)NR_{29}R_{30}$, $C(O)NR_{29}R_{30}$, $OC(O)NR_{29}R_{30}$ (wherein $R_{29}$, $R_{30}$ and $R_{31}$ are each independently selected from H, $C_{1-6}$ alkyl, $C_{6-12}$ aryl, $C_{6-12}$ aralkyl (e.g. $C_{7-12}$ aralkyl) or 3 to 10 membered heterocycle, or $R_{29}$ and $R_{30}$ are taken together with the atoms to which they are attached to form a 3 to 10 membered heterocycle), $SO_2NR_{32}R_{33}$, $NR_{32}SO_2R_{33}$ (wherein $R_{32}$ and $R_{33}$ are each independently selected from the group consisting of H, $C_{1-6}$ alkyl, $C_{6-12}$ aryl, 3 to 10 membered heterocycle and $C_{6-12}$ aralkyl (e.g. $C_{7-12}$ aralkyl)), $C(R_{34})NR_{35}$ or $C(R_{34})NOR_{35}$ (wherein $R_{34}$ and $R_{35}$ are each independently selected from the group consisting of H, $C_{1-6}$ alkyl, or $C_{6-12}$ aryl).

The term "urea" represents —$N(R_{36})CONR_{37}R_{38}$ wherein $R_{36}$ is H or $C_{1-6}$ alkyl and wherein $R_{37}$ and $R_{38}$ are each independently selected from the group consisting of H, $C_{1-6}$ alkyl, $C_{6-12}$ aryl, 3 to 10 membered heterocycle and $C_{6-12}$ aralkyl (e.g. $C_{7-12}$ aralkyl), or $R_{37}$ and $R_{38}$ are taken together with the nitrogen to which they are attached to form a 3 to 10 membered heterocycle.

"Oxidation levels": When there is a sulfur atom present, the sulfur atom can be at different oxidation levels, i.e. S, SO, or $SO_2$. All such oxidation levels are within the scope of the present invention. When there is a nitrogen atom present, the nitrogen atom can be at different oxidation levels, i.e. N or NO. All such oxidation levels are within the scope of the present invention.

The term "protecting group" such as "hydroxyl protecting group" and "amine protecting group" are well understood by one skilled in the art. In particular one skilled in the art is aware of various protecting groups for use to protect hydroxyl and primary and secondary amine groups. Protecting groups, including include those described for example, in T. W. Greene and P. G. M. Wuts, "Protecting Groups in Organic Synthesis" (1991) provided that they are suitable for use in the chemistries described herein. Particular examples of hydroxyl protecting groups include methyl, benzyl, benzyloxymethyl, or allyl.

Amino protecting groups are well known in the art and include those described in detail in Protecting Groups in Organic Synthesis, T. W. Greene and P. G. M. Wuts, 3.sup.rd edition, John Wiley & Sons, 1999, the entirety of which is incorporated herein by reference. Suitable amino protecting groups, taken with the —N— moiety to which it is attached, include, but are not limited to, aralkylamines, carbamates, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxycarbonyl (CBZ), allyl, benzyl (Bn), fluorenylmethylcarbonyl (Fmoc), acetyl, chloroacetyl, dichloroacetyl, trichloroacetyl, phenylacetyl, trifluoroacetyl, benzoyl, and the like. In still other embodiments, an amino group may be in protected form as a phthalimide or azide.

One of ordinary skill in the art will appreciate that certain moieties are incompatible with (i.e. may interfere with) certain chemical transformations as described herein. Thus, it will be understood that in for certain chemical transformations, certain moieties, e.g. a hydroxyl group or an amino group (primary or secondary), are preferably protected by a suitable protecting group as described herein prior to those transformations.

Suitable leaving groups are well known in the art, e.g., see, "Advanced Organic Chemistry," Jerry March, 5.sup.th Ed., pp. 445-448, John Wiley and Sons, N.Y. Such leaving groups include, but are not limited to, halogen, alkoxy, sulfonyloxy, optionally substituted alkylsulfonyloxy, optionally substituted alkenylsulfonyloxy, optionally substituted arylsulfonyloxy. Examples of suitable leaving groups include chloro, iodo, bromo, fluoro, methanesulfonyl (mesyl), tosyl, triflyl, nitrophenylsulfonyl (nosyl), bromophenylsulfonyl (brosyl), and the like.

There is also provided "pharmaceutically acceptable hydrates" of the compounds of the present invention. "Hydrates" exist when the compound of the invention incorporates water. The hydrate may contain one or more molecule of water per molecule of compound of the invention. Illustrative non-limiting examples include monohydrate, dihydrate, trihydrate and tetrahydrate. The hydrate may contain one or more molecule of compound of the invention per molecule of water. Illustrative non-limiting examples include semi-hydrate. In one embodiment, the water may be held in the crystal in various ways and thus, the water molecules may occupy lattice positions in the crystal, or they may form bonds with salts of the compounds as described herein. The hydrate must be "acceptable" in the sense of not being deleterious to the recipient thereof. The hydration may be assessed by methods known in the art such as Loss on Drying techniques (LOD) and Karl Fisher titration.

There is also provided "pharmaceutically acceptable salts" of the compounds of the present invention. By the term "pharmaceutically acceptable salts" of compounds are meant those derived from pharmaceutically acceptable inorganic and organic acids and bases. Examples of suitable acids include but are not limited to hydrochloric, hydrobromic, sulphuric, nitric, perchloric, fumaric, maleic, phosphoric, glycolic, lactic, salicylic, succinic, toluene-p-sulphonic, tartaric, acetic, trifluoroacetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts.

Salts derived from appropriate bases include alkali metal, alkaline earth metal or ammonium salts. The salt(s) must be "acceptable" in the sense of not being deleterious to the recipient thereof. Non-limiting examples of such salts known by those of ordinary skill in the art include without limitation calcium, potassium, sodium, choline, ethylenediamine, tromethamine, arginine, glycinelycine, lycine, magnesium and meglumine.

There is also provided a "pharmaceutically acceptable solvates" of the compounds of the present invention. The term "solvate" means that the compound of the invention incorporates one or more pharmaceutically acceptable solvent. The solvate may contain one or more molecule of solvent per molecule of compound of the invention or may contain one or more molecule of compound of the invention per molecule of solvent. In one embodiment, the solvent may be held in the crystal in various ways and thus, the solvent molecule may occupy lattice positions in the crystal, or they may form bonds with salts of the compounds as described herein. The solvate(s) must be "acceptable" in the sense of not being deleterious to the recipient thereof. The salvation may be assessed by methods known in the art such as Loss on Drying techniques (LOD).

"Polymorphs": It will be appreciated by those skilled in the art that the compounds in accordance with the present invention can exist in several different crystalline forms due to a different arrangement of molecules in the crystal lattice. This may include solvate or hydrate (also known as pseudopolymorphs) and amorphous forms. All such crystalline forms and polymorphs are included within the scope of the invention. The polymorphs may be characterized by methods well known in the art. Examples of analytical procedures that may be used to determine whether polymorphism occurs include: melting point (including hot-stage microscopy), infrared (not in solution), X-ray powder diffraction, thermal analysis methods (e.g. differential scanning calorimetry (DSC), differential thermal analysis (DTA), thermogravimetric analysis (TGA)), Raman spectroscopy, comparative intrinsic dissolution rate, scanning electron microscopy (SEM).

In one aspect, the present invention provides novel compounds according to formula I including:

| # | |
|---|---|
| 1 | 4,4-Difluoro-1-methylcyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide; |
| 2 | Isopropylcarboxylic acid {(S)-3-[1-isopropyl-3-(tetrahydropyran-4-ylmethyl)-bicyclo[3.2.1]-2-oxo-1β,3,8-triaza-spiro[4.5]dodec-8-yl]-1-phenyl-propyl}-amide; |
| 3 | 4,4-Difluoro-cyclohexanecarboxylic acid {(S)-3-[3-(tetrahydro-pyran-4-ylmethyl)-bicyclo[3.2.1]-2-oxo-1β,3,8-triaza-spiro[4.5]dodec-8-yl]-1-phenyl-propyl}-amide; |

| # | |
|---|---|
| 4 | 4,4-Difluoro-cyclohexanecarboxylic acid {(S)-3-[1-methyl-3-(tetrahydro-pyran-4-ylmethyl)-bicyclo[3.2.1]-2-oxo-1β,3,8-triaza-spiro[4.5]dodec-8-yl]-1-phenyl-propyl}-amide; |
| 5 | 4,4-Difluoro-cyclohexanecarboxylic acid {(S)-3-[1-ethyl-3-(tetrahydro-pyran-4-ylmethyl)-bicyclo[3.2.1]-2-oxo-1β,3,8-triaza-spiro[4.5]dodec-8-yl]-1-phenyl-propyl}-amide; |
| 6 | 4,4-Difluoro-cyclohexanecarboxylic acid {(S)-3-[1-isobutyl-3-(tetrahydro-pyran-4-ylmethyl)-bicyclo[3.2.1]-2-oxo-1β,3,8-triaza-spiro[4.5]dodec-8-yl]-1-phenyl-propyl}-amide; |
| 7 | Cyclopropylcarboxylic acid {(S)-3-[1-isopropyl-3-(tetrahydropyran-4-ylmethyl)-bicyclo[3.2.1]-2-oxo-1β,3,8-triaza-spiro[4.5]dodec-8-yl]-1-phenyl-propyl}-amide; |
| 8 | Cyclopent-1-enecarboxylic acid {(S)-3-[1-isopropyl-3-(tetrahydropyran-4-ylmethyl)-bicyclo[3.2.1]-2-oxo-1β,3,8-triaza-spiro[4.5]dodec-8-yl]-1-phenyl-propyl}-amide; |
| 9 | 1-Methyl-1H-imidazole-2-carboxylic acid {(S)-3-[1-isopropyl-3-(tetrahydropyran-4-ylmethyl)-bicyclo[3.2.1]-2-oxo-1β,3,8-triaza-spiro[4.5]dodec-8-yl]-1-phenyl-propyl}-amide; |
| 10 | Isopropylcarboxylic acid {(S)-3-[3-(tetrahydropyran-4-ylmethyl)-bicyclo[3.2.1]-2-oxo-1β,3,8-triaza-spiro[4.5]dodec-8-yl]-1-phenyl-propyl}-amide; |
| 11 | Isopropylcarboxylic acid {(S)-3-[1-methyl-3-(tetrahydropyran-4-ylmethyl)-bicyclo[3.2.1]-2-oxo-1β,3,8-triaza-spiro[4.5]dodec-8-yl]-1-phenyl-propyl}-amide; |
| 12 | Isopropylcarboxylic acid {(S)-3-[1-ethyl-3-(tetrahydropyran-4-ylmethyl)-bicyclo[3.2.1]-2-oxo-1β,3,8-triaza-spiro[4.5]dodec-8-yl]-1-phenyl-propyl}-amide; |
| 13 | 4,4-Difluoro-cyclohexanecarboxylic acid {(S)-1-isopropyl-3-(5-methyl-[1,3]dioxan-5-ylmethyl)-bicyclo[3.2.1]-2-oxo-1β,3,8-triaza-spiro[4.5]dodec-8-yl]-1-phenyl-propyl}-amide; | and pharmaceutically acceptable salts (e.g., hydrochloride salts), hydrates or solvates thereof.

In another aspect, the present invention provides novel compounds according to formula I including:

| 14 | 4,4-Difluoro-cyclohexanecarboxylic acid {(S)-3-[1-isopropyl-3-(tetrahydropyran-3-yl)-bicyclo[3.2.1]-2-oxo-1β,3,8-triaza-spiro[4.5]dodec-8-yl]-1-phenyl-propyl}-amide |
|---|---|
| 15 | 4,4-Difluoro-cyclohexanecarboxylic acid {(S)-3-[1-isopropyl-3-(3-methyl-oxetan-3-ylmethyl)-bicyclo[3.2.1]-2-oxo-1β,3,8-triaza-spiro[4.5]dodec-8-yl]-1-phenyl-propyl}-amide |
| 16 | 4-Hydroxy-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 17 | Cyclohex-1-enecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 18 | N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-2-trifluoromethyl-acrylamide |
| 19 | N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-2-methyl-acrylamide |
| 20 | 2-Ethyl-N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-butyramide |
| 21 | N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-propionamide |
| 22 | 4,4-Difluoro-cyclohexanecarboxylic acid {(S)-3-[3-(5-methyl-[1,3]dioxan-5-ylmethyl)-bicyclo[3.2.1]-2-oxo-1β,3,8-triaza-spiro[4.5]dodec-8-yl]-1-phenyl-propyl}-amide |
| 23 | 4,4-Difluoro-cyclohexanecarboxylic acid {(S)-3-[1-methyl-3-(5-methyl-[1,3]dioxan-5-ylmethyl)-bicyclo[3.2.1]-2-oxo-1β,3,8-triaza-spiro[4.5]dodec-8-yl]-1-phenyl-propyl}-amide |
| 24 | 4,4-Difluoro-cyclohexanecarboxylic acid {(S)-3-[1-ethyl-3-(5-methyl-[1,3]dioxan-5-ylmethyl)-bicyclo[3.2.1]-2-oxo-1β,3,8-triaza-spiro[4.5]dodec-8-yl]-1-phenyl-propyl}-amide |
| 25 | N-{(S)-3-[1-methyl-3-(5-methyl-[1,3]dioxan-5-ylmethyl)-bicyclo[3.2.1]-2-oxo-1β,3,-triaza-spiro[4.5]dodec-8-yl]-1-phenyl-propyl}-isobutyramide |
| 26 | N-{(S)-3-[1-ethyl-3-(5-methyl-[1,3]dioxan-5-ylmethyl)-bicyclo[3.2.1]-2-oxo-1β,3,-triaza-spiro[4.5]dodec-8-yl]-1-phenyl-propyl}-isobutyramide |
| 27 | N-{(S)-3-[1-isopropyl-3-(5-methyl-[1,3]dioxan-5-ylmethyl)-bicyclo[3.2.1]-2-oxo-1β,3,-triaza-spiro[4.5]dodec-8-yl]-1-phenyl-propyl}-isobutyramide |
| 28 | 4,4-Difluoro-cyclohexanecarboxylic acid {(S)-3-[1-isopropyl-3-(5-ethyl-[1,3]dioxan-5-ylmethyl)-bicyclo[3.2.1]-2-oxo-1β,3,8-triaza-spiro[4.5]dodec-8-yl]-1-phenyl-propyl}-amide |
| 29 | 4,4-Difluoro-cyclohexanecarboxylic acid {(S)-3-[3-([1,3]dioxolan-2-ylmethyl)-1-isopropyl-bicyclo[3.2.1]-2-oxo-1β,3,8-triaza-spiro[4.5]dodec-8-yl]-1-phenyl-propyl}-amide |
| 30 | 4,4-Difluoro-cyclohexanecarboxylic acid {(S)-3-[3-(5-ethyl-[1,3]dioxan-5-ylmethyl)-bicyclo[3.2.1]-2-oxo-1β,3,8-triaza-spiro[4.5]dodec-8-yl]-1-phenyl-propyl}-amide |
| 31 | 4,4-Difluoro-cyclohexanecarboxylic acid {(S)-3-[1-ethyl-3-(5-ethyl-[1,3]dioxan-5-ylmethyl)-bicyclo[3.2.1]-2-oxo-1β,3,8-triaza-spiro[4.5]dodec-8-yl]-1-phenyl-propyl}-amide |
| 32 | N-{(S)-3-[1-ethyl-3-(5-ethyl-[1,3]dioxan-5-ylmethyl)-bicyclo[3.2.1]-2-oxo-1β,3,8-triaza-spiro[4.5]dodec-8-yl]-1-phenyl-propyl}-isobutyramide |
| 33 | {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-carbamic acid methyl ester |
| 34 | {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-carbamic acid ethyl ester |
| 35 | {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-carbamic acid isopropyl ester |
| 36 | Cis-4-hydroxy-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 37 | 4-Methoxy-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 38 | N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-acetamide |
| 39 | 2,2,2-Trifluoro-N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-acetamide |
| 40 | 4,4-Difluoro-cyclohexanecarboxylic acid {(S)-3-[3-([1,3]dioxan-5-ylmethyl)-bicyclo[3.2.1]-2-oxo-1β,3,8-triaza-spiro[4.5]dodec-8-yl]-1-phenyl-propyl}-amide |
| 41 | 4,4-Difluoro-cyclohexanecarboxylic acid {(S)-3-[1-ethyl-3-([1,3]dioxan-5-ylmethyl)-bicyclo[3.2.1]-2-oxo-1β,3,8-triaza-spiro[4.5]dodec-8-yl]-1-phenyl-propyl}-amide |
| 42 | 4,4-Difluoro-cyclohexanecarboxylic acid {(S)-3-[1-isopropyl-3-([1,3]dioxan-5-ylmethyl)-bicyclo[3.2.1]-2-oxo-1β,3,8-triaza-spiro[4.5]dodec-8-yl]-1-phenyl-propyl}-amide |
| 43 | 4,4-Difluoro-cyclohexanecarboxylic acid {(S)-3-[1-methyl-3-([1,3]dioxan-5-ylmethyl)-bicyclo[3.2.1]-2-oxo-1β,3,8-triaza-spiro[4.5]dodec-8-yl]-1-phenyl-propyl}-amide |
| 44 | 2,2-Difluoro-cyclopropanecarboxylic acid {(S)-3-[1-isopropyl-3-(tetrahydro-pyran-4-ylmethyl)- |

| 45 | 3,3,3-Trifluoro-N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-propionamide |
| --- | --- |
| 46 | Trans-4-hydroxy-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 47 | 3,3-Difluoro-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 48 | 3,3-Difluoro-cyclobutanecarboxylic acid {(S)-3-[1-isopropyl-3-([1,3]dioxan-5-ylmethyl)-bicyclo[3.2.1]-2-oxo-1β,3,8-triaza-spiro[4.5]dodec-8-yl]-1-phenyl-propyl}-amide |
| 49 | Trans-4-trifluoromethyl-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 50 | 1-Acetyl-piperidine-4-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 51 | Tetrahydro-thiopyran-4-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 52 | 2H-Thiopyran-4-carboxamide tetrahydro-N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-1-oxide |
| 53 | 2H-Thiopyran-4-carboxamide tetrahydro-N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-1,1-dioxide |
| 54 | 4-Fluoro-N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-benzamide |
| 55 | Trans-4-methoxy-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 56 | Cis-4-methoxy-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 57 | 6-Oxo-piperidine-3-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 58 | Trans-4-ethoxy-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 59 | 2-Oxo-piperidine-4-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 60 | Trans-4-trifluoromethoxy-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 61 | Trans-4-fluoro-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 62 | 4-Hydroxy-4-methyl-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 63 | 4-Hydroxy-4-trifluoromethyl-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 64 | Trans-4-[1,2,3]triazol-1-yl-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 65 | Isopropyl-carbamic acid 4-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propylcarbamoyl}-cyclohexyl ester |
| 66 | 1-Hydroxy-piperidine-4-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 67 | 4-Hydroxyimino-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 68 | 4-Methoxyimino-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 69 | 5-Oxo-pyrrolidine-3-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 70 | 1-Methyl-5-oxo-pyrrolidine-3-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 71 | 2-Oxo-imidazolidine-4-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 72 | 3-Hydroxy-cyclopentanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 73 | 2-Hydroxy-N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-2-methyl-propionamide |
| 74 | N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-2-methoxy-2-methyl-propionamide |
| 75 | 4-Hydroxy-but-2-ynoic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 76 | 4-Hydroxy-4-methyl-pent-2-ynoic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 77 | 3-Hydroxy-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 78 | 3-Methoxy-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 79 | 3-Hydroxy-3-methyl-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 80 | 3-Hydroxy-3-trifluoromethyl-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 81 | (S)-4-Oxo-azetidine-2-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 82 | 3-Hydroxyimino-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 83 | 3-Methoxyimino-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 84 | 1-Acetyl-azetidine-3-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |

| | -continued |
|---|---|
| 85 | Trans-3-acetylamino-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 86 | Cis-3-acetylamino-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide | and pharmaceutically acceptable salts (e.g., hydrochloride salts), hydrates or solvates thereof.

It will be appreciated that the amount of a compound of the invention required for use in treatment will vary not only with the particular compound selected but also with the route of administration, the nature of the condition for which treatment is required and the age and condition of the patient and will be ultimately at the discretion of the attendant physician or veterinarian. In general however a suitable dose will be in the range of from about 0.1 to about 750 mg/kg of body weight per day, preferably in the range of 0.5 to 60 mg/kg/day, most preferably in the range of 1 to 20 mg/kg/day.

The desired dose may conveniently be presented in a single dose or as divided dose administered at appropriate intervals, for example as two, three, four or more doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 μM, preferably about 2 to 50 μM, most preferably about 3 to about 30 μM. This may be achieved, for example, by the intravenous injection of a 0.1 to 5% solution of the active ingredient, optionally in saline, or orally administered as a bolus containing about 1 to about 500 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of the invention may be administered as the raw chemical it is preferable to present the active ingredient as a pharmaceutical formulation. The invention thus further provides a pharmaceutical formulation comprising a compound of formula (I) or a pharmaceutically acceptable derivative thereof together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), transdermal, vaginal or parenteral (including intramuscular, subcutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulation suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis, the compounds according to the invention may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops. Drops may be formulated with an aqueous or non-aqueous base also comprising one more dispersing agents, solubilising agents or suspending agents. Liquid sprays are conveniently delivered from pressurized packs.

For administration by inhalation the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

When the compound (I) or a pharmaceutically acceptable salt, hydrate or solvate thereof is used in combination with a second therapeutic active agent, the dose of each compound may be either the same as or different from that when the compound is used alone. Conventional doses and regimens are readily appreciated by those skilled in the art, including doses described in the Physicians Desk Reference, 56$^{th}$ edition, 2002.

The present invention is directed to the use of the compounds as modulators of CCR5 chemokine receptor activity. In particular, certain compounds of the invention have been found to have activity in binding to the CCR5 receptor in the biological assay, as described in Example 5, generally with an IC$_{50}$ value of less than 25 μM. The terms "modulator" or "modulation" are meant to include antagonism, agonism, mixed and partial antagonism and agonism.

Certain compounds of the present invention have also been tested in an assay for HIV activity, as described in Example 5, and generally having an IC$_{50}$ value of less than 1 μM.

According to s further aspect, the present invention provides novel intermediate compounds according to formula III including:

| # | |
|---|---|
| A | 1-Isopropyl-3-(4-methoxy-phenyl)-bicyclo[3.2.1]-1β,3,8-triaza-spiro[4.5]dodecan-2,4-dione; |
| B | 1-Isopropyl-3-(3-methoxy-phenyl)-bicyclo[3.2.1]-1β,3,8-triaza-spiro[4.5]dodecan-2,4-dione; |
| C | 1-Isopropyl-3-(2-methoxy-phenyl)-bicyclo[3.2.1]-1β,3,8-triaza-spiro[4.5]dodecan-2,4-dione; |
| D | 1-Isopropyl-3-(tetrahydropyran-4-yl)-bicyclo[3.2.1]-1β,3,8-triaza-spiro[4.5]dodecan-2,4-dione; |
| E | 1-Isopropyl-3-(tetrahydropyran-4-ylmethyl)-bicyclo[3.2.1]-1β,3,8-triaza-spiro[4.5]dodecan-2,4-dione; |
| F | 1-Isopropyl-3-(tetrahydrofuran-3-yl)-bicyclo[3.2.1]-1β,3,8-triaza-spiro[4.5]dodecan-2,4-dione; |
| G | 3-(1-Isopropyl-bicyclo[3.2.1]-1β,3,8-triaza-spiro[4.5]dodecan-2,4-dione)-pyrrolidine-1-carboxylic acid tert-butyl ester; |
| H | 3-[1,3]Dioxan-5-yl-1-isopropyl-bicyclo[3.2.1]-1β,3,8-triaza-spiro[4.5]dodecan-2,4-dione; |
| I | 1-Isopropyl-3-(2-methoxyethyl)-bicyclo[3.2.1]-1β,3,8-triaza-spiro[4.5]dodecan-2,4-dione; |
| J | 1-Isopropyl-3-(2-methoxy-2-methylpropyl)-bicyclo[3.2.1]-1β,3,8-triaza-spiro[4.5]dodecan-2,4-dione; |
| K | 1-Isopropyl-3-(3-methoxypropyl)-bicyclo[3.2.1]-1β,3,8-triaza-spiro[4.5]dodecan-2,4-dione; |
| L | 3-(2-Isopropoxyethyl)-1-isopropyl-bicyclo[3.2.1]-1β,3,8-triaza-spiro[4.5]dodecan-2,4-dione; |
| M | 1-Isopropyl-3-(tetrahydrofuran-3-ylmethyl)-bicyclo[3.2.1]-1β,3,8-triaza-spiro[4.5]dodecan-2,4-dione; |
| N | 1-Isopropyl-3-(tetrahydrofuran-2-ylmethyl)-bicyclo[3.2.1]-1β,3,8-triaza-spiro[4.5]dodecan-2,4-dione; |
| O | 3-[1,3]Dioxolan-4-ylmethyl-1-isopropyl-bicyclo[3.2.1]-1β,3,8-triaza-spiro[4.5]dodecan-2,4-dione; |
| P | 3-Furan-2-ylmethyl-1-isopropyl-bicyclo[3.2.1]-1β,3,8-triaza-spiro[4.5]dodecan-2,4-dione; |
| Q | 1-Isopropyl-3-thiophen-2-ylmethyl-bicyclo[3.2.1]-1β,3,8-triaza-spiro[4.5]dodecan-2,4-dione; |
| R | 1-Isopropyl-3-thiazol-2-ylmethyl-bicyclo[3.2.1]-1β,3,8-triaza-spiro[4.5]dodecan-2,4-dione; |
| S | (S)-1-isopropyl-3-(tetrahydrofuran-3-yl)-bicyclo[3.2.1]-1β,3,8-triaza-spiro[4.5]dodecan-2-one; |
| T | 1-Isopropyl-3-(tetrahydropyran-4-ylmethyl)-bicyclo[3.2.1]-1β,3,8-triaza-spiro[4.5]dodecan-2-one; |
| U | (R)-1-isopropyl-3-(tetrahydrofuran-3-yl)-bicyclo[3.2.1]-1β,3,8-triaza-spiro[4.5]dodecan-2-one; |
| V | 1-Isopropyl-3-(tetrahydrofuran-3-yl)-bicyclo[3.2.1]-1β,3,8-triaza-spiro[4.5]dodecan-2-one; |
| W | 1-Isopropyl-3-(tetrahydropyran-4-yl)-bicyclo[3.2.1]-1β,3,8-triaza-spiro[4.5]dodecan-2-one; |
| X | 1-Isopropyl-3-(tetrahydropyran-3-yl)-bicyclo[3.2.1]-1β,3,8-triaza-spiro[4.5]dodecan-2-one; |
| Y | 1-Isopropyl-3-(4-methoxy-cyclohexyl)-bicyclo[3.2.1]-1β,3,8-triaza-spiro[4.5]dodecan-2-one; |
| Z | 1-Isopropyl-3-(tetrahydropyran-3-ylmethyl)-bicyclo[3.2.1]-1β,3,8-triaza-spiro[4.5]dodecan-2-one; |
| AA | 1-Isopropyl-3-(tetrahydropyran-2-ylmethyl)-bicyclo[3.2.1]-1β,3,8-triaza-spiro[4.5]dodecan-2-one; |
| AB | 1-Isopropyl-3-(5-methyl-[1,3]dioxan-5-ylmethyl)-bicyclo[3.2.1]-1β,3,8-triaza-spiro[4.5]dodecan-2-one; |
| AC | 1-Isopropyl-3-(tetrahydrofuran-3-ylmethyl)-bicyclo[3.2.1]-1β,3,8-triaza-spiro[4.5]dodecan-2-one; |
| AD | 1-Isopropyl-3-(tetrahydrofuran-2-ylmethyl)-bicyclo[3.2.1]-1β,3,8-triaza-spiro[4.5]dodecan-2-one; |
| AE | (R)-1-Isopropyl-3-(tetrahydrofuran-2-ylmethyl)-bicyclo[3.2.1]-1β,3,8-triaza-spiro[4.5]dodecan-2-one; |
| AF | (S)-1-Isopropyl-3-(tetrahydrofuran-2-ylmethyl)-bicyclo[3.2.1]-1β,3,8-triaza-spiro[4.5]dodecan-2-one; |
| AG | 1-Isopropyl-3-(3-methyl-oxetan-3-ylmethyl)-bicyclo[3.2.1]-1β,3,8-triaza-spiro[4.5]dodecan-2-one; |
| AH | 1-Isopropyl-3-(2-methoxyethyl)-bicyclo[3.2.1]-1β,3,8-triaza-spiro[4.5]dodecan-2-one; |
| AI | 1-Isopropyl-3-(2-ethoxyethyl)-bicyclo[3.2.1]-1β,3,8-triaza-spiro[4.5]dodecan-2-one; |
| AJ | 1-Isopropyl-3-(2-methoxy-2-methylpropyl)-bicyclo[3.2.1]-1β,3,8-triaza-spiro[4.5]dodecan-2-one; |
| AK | 1-Isopropyl-3-(3-methoxypropyl)-bicyclo[3.2.1]-1β,3,8-triaza-spiro[4.5]dodecan-2-one; |
| AL | 3-(2-Isopropoxyethyl)-1-isopropyl-bicyclo[3.2.1]-1β,3,8-triaza-spiro[4.5]dodecan-2-one; |
| AM | 3-Furan-2-ylmethyl-1-isopropyl-bicyclo[3.2.1]-1β,3,8-triaza-spiro[4.5]dodecan-2-one; |
| AN | 1-Isopropyl-3-thiophen-2-ylmethyl-bicyclo[3.2.1]-1β,3,8-triaza-spiro[4.5]dodecan-2-one; |
| AO | 1-Isopropyl-3-thiazol-2-ylmethyl-bicyclo[3.2.1]-1β,3,8-triaza-spiro[4.5]dodecan-2-one; |
| AP | 1-Isopropyl-3-(1-methyl-1H-imidazol-2-ylmethyl)-bicyclo[3.2.1]-1β,3,8-triaza-spiro[4.5]dodecan-2-one; |
| AQ | 1-Isopropyl-3-(4-methoxy-phenyl)-bicyclo[3.2.1]-1β,3,8-triaza-spiro[4.5]dodecan-2-one |
| AR | 1-Isopropyl-3-(3-methoxy-phenyl)-bicyclo[3.2.1]-1β,3,8-triaza-spiro[4.5]dodecan-2-one; |
| AS | 1-Isopropyl-3-(2-methoxy-phenyl)-bicyclo[3.2.1]-1β,3,8-triaza-spiro[4.5]dodecan-2-one; |
| AT | 3-(Tetrahydropyran-4-ylmethyl)-bicyclo[3.2.1]-1β,3,8-triaza-spiro[4.5]dodecan-2-one; |
| AU | 1-Methyl-3-(tetrahydropyran-4-ylmethyl)-bicyclo[3.2.1]-1β,3,8-triaza-spiro[4.5]dodecan-2-one; |
| AV | 1-Ethyl-3-(tetrahydropyran-4-ylmethyl)-bicyclo[3.2.1]-1β,3,8-triaza-spiro[4.5]dodecan-2-one; |
| AW | 1-Isobutyl-3-(tetrahydropyran-4-ylmethyl)-bicyclo[3.2.1]-1β,3,8-triaza-spiro[4.5]dodecan-2-one; | and pharmaceutically acceptable salts, hydrates or solvates thereof.

The purity and mass of the following examples were characterized by mass spectra (LC/MS) and or NMR spectra.

In the foregoing and in the following examples, all temperatures are set forth uncorrected in degrees Celsius; and, unless otherwise indicated, all parts and percentages are by weight.

The entire disclosures of all applications, patents and publications, cited above and below, are hereby incorporated by reference.

The following general schemes and examples are provided to illustrate various embodiments of the present invention and shall not be considered as limiting in scope.

The following abbreviations may be used as follows:

| | |
|---|---|
| br | broad |
| DCM | dichloromethane |
| DMAC | dimethylacetamide |
| DMSO | dimethyl sulfoxide |
| DMF | N,N-dimethylformamide |
| LAH | lithium aluminium hydride |
| L | Leaving group |
| OMs | mesylate |
| OTs | toluenesulfonyl |
| NMP | 1-methyl-2-pyrrolidinone |
| PG | Protecting group |
| Quint. | quintet |
| Sept. | septuplet |
| THF | tetrahydrofuran |

Scheme 1

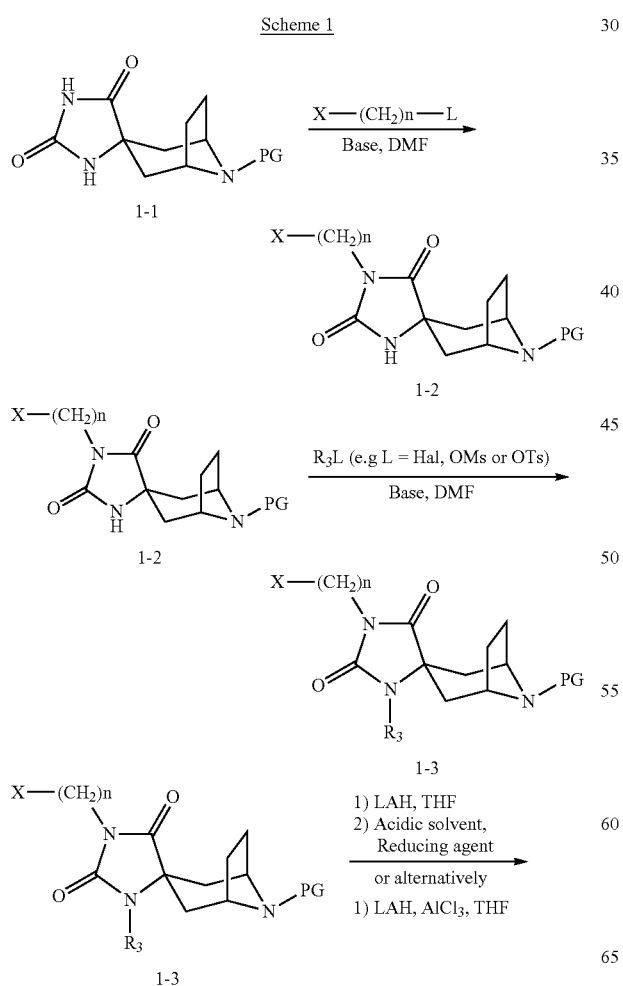

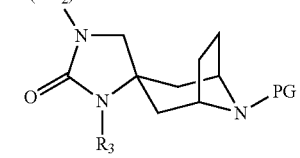

1-4

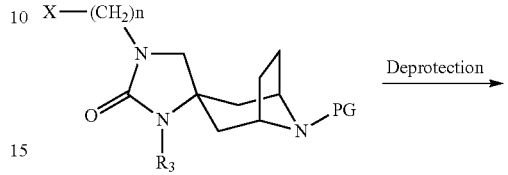

1-4

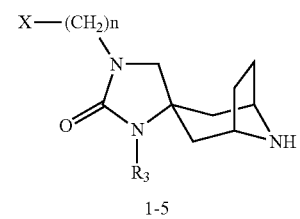

1-5

General procedure: The N8-PG-bicyclo[3.2.1]-1β,3,8-triaza-spiro[4.5]dodecan-2,4-dione 1-1 is treated with $X$—$(CH_2)_n$-L and a base such as $Na_2CO_3$, $K_2CO_3$ or $Cs_2CO_3$ in polar solvent such as DMF at temperature between 20 to 100° C. to yield the hydantoin 1-2.

Further N1-alkylation takes place by treating the hydantoin 1-2 with a strong base such as KH, NaH or LiH and an electrophile $R_3L$ in aprotic solvent such as DMF, NMP, DMAC or DMSO at temperature between 20 and 100° C. N1 and N3 bisalkylated hydantoin 1-3 is sequentially reduced by treatment with LAH followed by a reducing agent such as sodium hydride or sodium triacetoxyborohydride in acidic solvent such as formic acid or acetic acid, or alternatively in one step by treatment with $LAH/AlCl_3$. Then N1 and N3 bisalkylated urea 1-4 is finally deprotected using standards procedures of hydrogenolysis or acidic treatment depending on the nature of the protecting group (PG).

Preparation 1

Methanesulfonic acid tetrahydropyran-4-ylmethyl ester

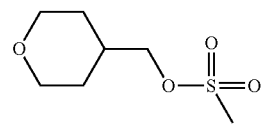

A solution of 90 g (774.8 mmol) of tetrahydropyran-4-methanol and 129.6 mL (929.76 mmol, 1.2 eq.) of triethylamine in 775 mL of anhydrous DCM was cooled to 0° C. with in an ice bath. Methanesulfonyl chloride (66.2 mL, 852.28 mmol, 1.1 eq.) of was then added dropwise over 60 minutes while maintaining the temperature around 0° C. The reaction mixture was stirred for 30 minutes at 0° C. and quenched with a saturated solution of sodium bicarbonate (800 mL). The aqueous layer was extracted with DCM (800 mL). The combined organic layers were washed with water (2×800 mL), brine (800 mL) and dried over sodium sulfate. After filtration and concentration in vacuo, a yellowish solid (146.1 g, 97%) was obtained corresponding to the methanesulfonic acid tetrahydropyran-4-ylmethyl ester.

1H NMR (400 MHz, DMSO-d$_6$): δ [ppm] 4.02 (d, 2H), 3.82 (m, 2H), 3.27 (t×d, 2H), 3.14 (s, 3H), 1.89 (m, 1H), 1.55 (m, 2H), 1.21 (q×d, 2H).

Preparation 2

1-Isopropyl-3-(tetrahydropyran-4-ylmethyl)-bicyclo[3.2.1]-1β,3,8-triaza-spiro[4.5]dodecan-2-one

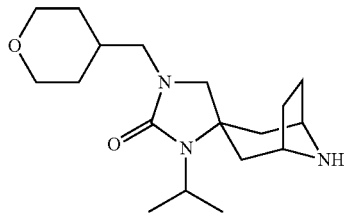

Step 1: To 400 g (1.846 mol) of 8-benzyl-8-aza-bicyclo[3.2.1]octan-3-one dissolved in 2000 mL of methanol was added successively 1149 g (14.768 mol, 8 eq.) of ammonium acetate and 110 g (2.25 mol, 1.15 eq.) of sodium cyanide. The reaction was stirred for 28.5 hours at room temperature. Then, 2000 mL of DCM and 1000 mL of water were added successively. The mixture was stirred for 5 minutes. After separation of the organic layer, the aqueous layer was extracted with 2000 mL of DCM. The organic layers were dried over sodium sulfate, filtered and evaporated in vacuo to yield 450 g (95%) of pale yellow solid of 3β-amino-8-benzyl-8-aza-bicyclo[3.2.1]-octane-3-carbonitrile and 8-benzyl-8-aza-bicyclo-[3.2.1]octan-3-one, respectively, in a ratio 90:10 as determined by 1H NMR.

Step 2: To 19.8 g (82 mmol) of 3β-amino-8-benzyl-8-aza-bicyclo[3.2.1]octane-3-carbonitrile dissolved in 68 mL of acetic acid (1.2M) was added dropwise a solution of 33.3 g (410 mmol, 5 eq.) of potassium cyanate in 34 mL of water (12M) over 30 minutes. The internal temperature rose to 75° C. Acetic acid was removed under reduced pressure. The resulting residue was neutralized with NaOH 1N-3N and extracted with DCM, dried over sodium sulfate, filtered off and concentrated. The residue was triturated with acetone to remove traces of starting material to yield a mixture (15.8 g) of (8-benzyl-3-cyano-8-aza-bicyclo[3.2.1]oct-3β-yl)-urea and 8-benzyl-4-imino-bicyclo[3.2.1]-1β,3,8-triaza-spiro[4.5]dodecan-2-one.

Step 3: To 15.8 g (56 mmol) of the previous mixture was added 140 mL of HCl 6N. The reaction mixture was heated for 2 hours at 110° C. and the solvent was removed in vacuo. The residue was neutralized with saturated solution of sodium bicarbonate and extracted with ethyl acetate (3×), dried over sodium sulfate, filtered and evaporated in vacuo. The residue was triturated with cold ethyl acetate to yield 13 g (11.8 g (1$^{st}$ trituration)+1.2 g (2$^{nd}$ trituration)) of 8-benzyl-bicyclo[3.2.1]-1β,3,8-triaza-spiro[4.5]dodecan-2,4-dione as a white solid.

Step 4: To 2.2 g (7.72 mmol) of 8-benzyl-bicyclo[3.2.1]-1β,3,8-triaza-spiro[4.5]dodecan-2,4-dione previously dissolved in 19 mL of anhydrous DMF was added 1.5 g (7.72 mmol, 1 eq.) of methanesulfonic acid tetrahydropyran-4-yl-methyl ester and 2.77 g (8.5 mmol, 1.1 eq.) of cesium carbonate. The reaction mixture was stirred for 15 hours at 60° C. While stirring, 38 mL of water were slowly added to obtain a white precipitate. The white precipitate was filtered off, washed back with water (3×20 mL), hexanes (2×20 mL) and dried in vacuo to yield 2.66 g (89.8%) of 8-benzyl-3-(tetrahydropyran-4-ylmethyl)-bicyclo[3.2.1]-1β,3,8-triaza-spiro[4.5]dodecan-2,4-dione.

1H NMR (400 MHz, DMSO-d$_6$): δ [ppm] 8.09 (s, 1H), 7.36-7.27 (m, 4H), 7.20 (m, 1H), 3.77 (br d×d, 2H), 3.52 (s, 2H), 3.21-3.14 (m, 6H), 1.98-1.89 (m, 6H), 1.79 (m, 1H), 1.70 (d×d, 2H), 1.38 (m, 2H), 1.10 (q×d, 2H).

Step 5: To a solution of 10 g (0.026 mol) of 8-benzyl-3-(tetrahydropyran-4-ylmethyl)-bicyclo[3.2.1]-1β,3,8-triaza-spiro[4.5]dodecan-2,4-dione in 200 mL of anhydrous DMF was added 3.13 g (0.078 mol) of sodium hydride in 5 portions over 5-10 minutes at room temperature. After hydrogene evolution had slowed down or stopped, 10.4 mL (0.104 mol) of isopropyl iodide was added and the reaction mixture was stirred for 24 hours at room temperature. The reaction sequence was repeated with additional 1.04 g of sodium hydride and 3.5 mL of isopropyl iodide. After an overnight stirring at room temperature, 70 mL of water was slowly added until appearance of solid. The suspension was cooled down to 0° C. and stirred for an additional hour, filtered then washed with 200 mL of cold water and 200 mL of hexanes. The precipitate was dried in the vacuum oven to yield 8.29 g (75%) of 8-benzyl-1-isopropyl-3-(tetrahydropyran-4-ylmethyl)-bicyclo[3.2.1]-1β,3,8-triaza-spiro[4.5]dodecan-2,4-dione as a pale beige powder.

Step 6: 3.62 g (8.521 mmol) of 8-benzyl-1-isopropyl-3-(tetrahydropyran-4-ylmethyl)-bicyclo[3.2.1]-1β,3,8-triaza-spiro[4.5]dodecan-2,4-dione was dissolved in 85 mL of anhydrous THF and the solution was cooled in an ice/water bath. Then 8.6 mL of LAH (1M in THF) was added dropwise and the reaction mixture was stirred for 60 minutes before being quenched by adding successively 0.33 mL of water followed by 0.33 mL of NaOH 15% (w/w) and 1 mL of water. The suspension was then warmed to room temperature. The white solid was filtered off and the filtrate was evaporated to give 3.74 g of 8-benzyl-4-hydroxy-1-isopropyl-3-(tetrahydropyran-4-ylmethyl)-bicyclo[3.2.1]-1β,3,8-triaza-spiro[4.5]dodecan-2-one used directly in the next step.

Step 7: 3.74 g (8.721 mmol) of 8-benzyl-4-hydroxy-1-isopropyl-3-(tetrahydropyran-4-ylmethyl)-bicyclo[3.2.1]-1β,3,8-triaza-spiro[4.5]dodecan-2-one was dissolved in 23 mL of formic acid and the solution was cooled in an ice/water bath. Then 1.33 g (35.184 mmol) of sodium borohydride was added in three portions. The reaction mixture was warmed to room temperature and stirred for an additional 90 minutes. The mixture was then cooled again in an ice water bath and 63 mL of NaOH 30% (w/w) was added carefully to bring the mixture to pH=14. The mixture was then extracted with DCM (3×100 mL). The combined organic layers were dried over Na$_2$SO$_4$, filtered and evaporated to give 3.42 g (98%) of 8-benzyl-1-isopropyl-3-(tetrahydropyran-4-ylmethyl)-bicyclo[3.2.1]-1β,3,8-triaza-spiro[4.5]dodecan-2-one.

Or alternatively to steps 6 and 7,

Step 8: AlCl$_3$ (237 mg, 1.777 mmol) was dissolved in 1.5 mL of anhydrous THF and the solution was cooled in an ice bath before adding dropwise 1.34 mL of LAH (1M in THF) (caution: the reaction was very exothermic). The solution was then stirred for 90 minutes and 191.2 mg (0.445 mmol) of 8-benzyl-1-isopropyl-3-(tetrahydropyran-4-ylmethyl)-bicyclo[3.2.1]-1β,3,8-triaza-spiro[4.5]dodecan-2,4-dione previously dissolved in 2 mL of anhydrous THF was then added dropwise. The resulting solution was stirred at 0° C. for an additional 60 minutes. The reaction mixture was then quenched with 2 mL of saturated Rochelle's salt and 5 mL of water. The resulting mixture was extracted with ethyl acetate (3×10 mL), the combined organic extracts were washed with brine, dried over Na$_2$SO$_4$, filtered and evaporated to give 133.7 mg (73%) of 8-benzyl-1-isopropyl-3-(tetrahydropyran-4-ylmethyl)-bicyclo[3.2.1]-1β,3,8-triaza-spiro[4.6]dodecan-2-one.

Step 9: 483 mg (1.173 mmol) of 8-benzyl-1-isopropyl-3-(tetrahydropyran-4-ylmethyl)-bicyclo[3.2.1]-1β,3,8-triaza-spiro[4.5]dodecan-2-one was dissolved in 7.5 mL of ethanol followed by palladium on charcoal (10% w/w dry basis, wet, 50 mg) and ammonium formate (222 mg, 3.52 mmol). The reaction mixture was then refluxed for two hours, cooled to room temperature, filtered over celite and evaporated to give 368 mg (98%) of 1-isopropyl-3-(tetrahydropyran-4-ylmethyl)-bicyclo[3.2.1]-1β,3,8-triaza-spiro[4.5]dodecan-2-one.

1H NMR (400 MHz, DMSO-d$_6$): δ [ppm] 4.32 (br s, 1H), 3.79 (br d×d, 2H), 3.40 (q, 4H), 3.24 (m, 3H), 2.79 (d, 2H), 1.77 (br d×d, 2H), 1.70 (m, 1H), 1.63 (br s, 4H), 1.52 (d, 2H), 1.43 (d×d, 2H), 1.19 (d, 6H), 1.12-1.02 (q×d, 2H).

Scheme 2

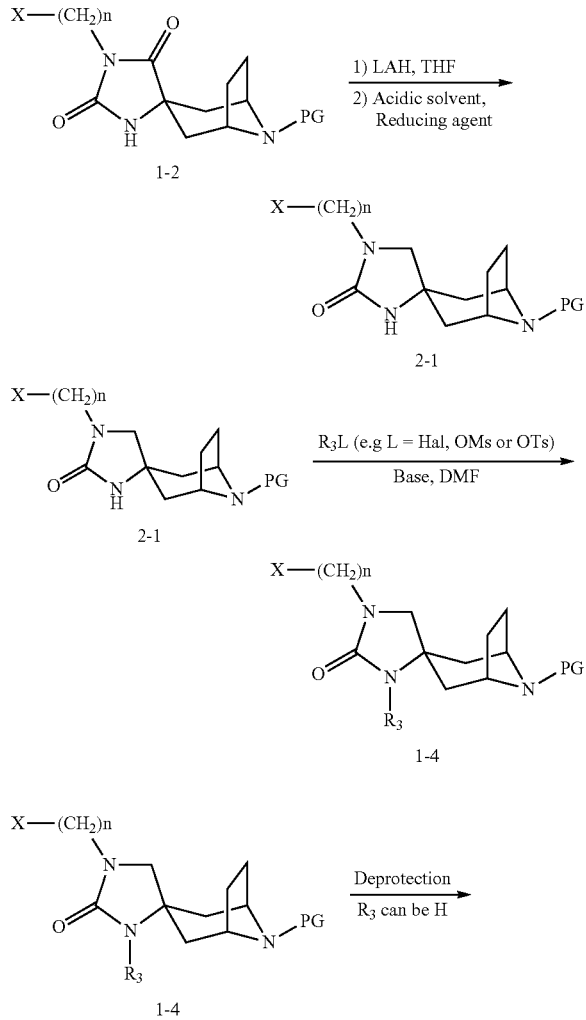

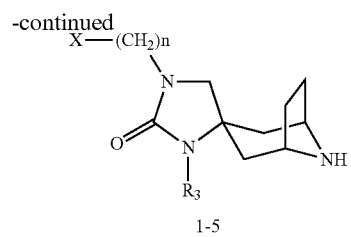

General procedure: N3 alkylated hydantoin 1-2 is sequentially reduced by treatment with LAH followed by a reducing agent such as sodium hydride or sodium triacetoxyborohydride in acidic solvent such as formic acid or acetic acid. Further N1-alkylation takes place by treating the urea 2-1 with a strong base such as KH, NaH or LiH and an electrophile R$_3$L in aprotic solvent such as DMF, NMP, DMAC or DMSO at temperature between 20 and 100° C. Then the resulting N3 monoalkylated urea 2-1 and the N1 and N3 bisalkylated urea 1-4 are finally deprotected using standards procedures of hydrogenolysis or acidic treatment depending on the nature of the protecting group (PG).

Preparation 3

3-(Tetrahydropyran-4-ylmethyl)-bicyclo[3.2.1]-1β,3,8-triaza-spiro[4.5]dodecan-2-one

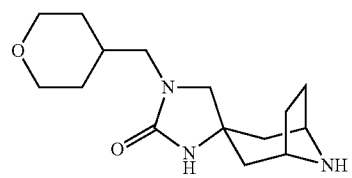

Step 1: To a solution of 8-benzyl-3-(tetrahydropyran-4-ylmethyl)-bicyclo[3.2.1]-1β,3,8-triaza-spiro[4.5]dodecan-2,4-dione (4.02 g, 10.48 mmol) in THF (50 mL) at 0° C. was added lithium aluminum hydride 1M/THF (14 mL, 14 mmol) dropwise. The mixture was warmed to room temperature and stirred overnight. The reaction mixture was quenched with water (0.5 mL) (very vigorous exotherm), aqueous NaOH (4M, 0.5 mL) and then water (1.5 mL). The mixture was filtered and the filter cake thoroughly rinsed with DCM. The mother liquor was evaporated to give 8-benzyl-4-hydroxy-3-(tetrahydropyran-4-ylmethyl)-bicyclo[3.2.1]-1β,3,8-triaza-spiro[4.5]dodecan-2-one as a white solid (3.4 g, 84%).

Step 2: To a solution of 8-benzyl-4-hydroxy-3-(tetrahydropyran-4-ylmethyl)-bicyclo[3.2.1]-1β,3,8-triaza-spiro[4.5]dodecan-2-one (3.4 g, 8.83 mmol) in formic acid (16 mL) at 0° C. was added sodium borohydride (1.33 g, 35.3 mmol) portionwise (vigorous reaction). The reaction was stirred at room temperature for 1.5 hour. The reaction mixture was neutralized with aqueous NaOH (4M, 100 mL) and extracted with DCM. The organic extracts were dried over sodium sulfate and evaporated to give 3-(tetrahydropyran-4-ylmethyl)-bicyclo[3.2.1]-1β,3,8-triaza-spiro[4.5]dodecan-2-one as a white solid (3.12 g, 96%).

1H NMR (400 MHz, CDCl$_3$): δ [ppm] 7.37-7.23 (m, 5H), 4.43 (s, 1H), 3.97-3.93 (m, 2H), 3.53 (s, 2H), 3.38 (s, 2H), 3.34 (d×t, 2H), 3.27 (s, 2H), 3.01 (d, 2H), 2.12-2.09 (m, 4H), 1.83-1.52 (m, 6H), 1.36-1.26 (d×q, 2H).

Step 3: Debenzylation was performed as described in Preparation 2, Step 9.

Preparation 4

1-Methyl-3-(tetrahydropyran-4-ylmethyl)-bicyclo[3.2.1]-1β,3,8-triaza-spiro[4.5]dodecan-2-one

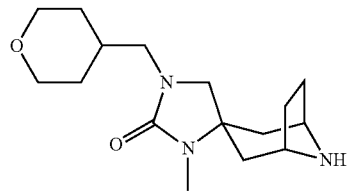

The N1-methylation of 3-(tetrahydropyran-4-ylmethyl)-bicyclo[3.2.1]-1β,3,8-triaza-spiro[4.5]dodecan-2-one was performed as described in Preparation 2, Step 5 using methyl iodide as alkylating agent.

1H NMR (400 MHz, CDCl$_3$): δ [ppm] 3.91 (dxd, 2H), 3.70 (br s, 2H), 3.32 (dxt, 2H), 3.32 (s, 2H), 2.98 (d, 2H), 2.65 (s, 3H), 2.08 (dxd, 2H), 1.93-1.89 (m, 2H), 1.76 (q, 2H), 1.75-1.70 (m, 1H), 1.63 (d, 2H), 1.52 (dxd, 2H), 1.28 (dxq, 2H).

Preparation 5

1-Ethyl-3-(tetrahydropyran-4-ylmethyl)-bicyclo[3.2.1]-1β,3,8-triaza-spiro[4.5]dodecan-2-one

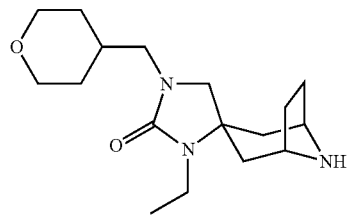

The N1-ethylation of 3-(tetrahydropyran-4-ylmethyl)-bicyclo[3.2.1]-1β,3,8-triaza-spiro[4.5]dodecan-2-one was performed as described in Preparation 2, Step 5 using ethyl iodide as alkylating agent.

1H NMR (400 MHz, CDCl$_3$): δ [ppm] 4.11 (br s, 2H), 3.95 (dxd, 2H), 3.36 (s, 2H), 3.32 (dxd, 2H), 3.25 (q, 2H), 3.00 (d, 2H), 2.47 (dxd, 2H), 2.43-2.29 (m, 2H), 1.93 (q, 2H), 1.85 (d, 2H), 1.76 (m, 1H), 1.53 (dxd, 2H), 1.36-1.26 (dxq, 2H), 1.13 (t, 3H).

Preparation 6

1-Isobutyl-3-(tetrahydropyran-4-ylmethyl)-bicyclo[3.2.1]-1β,3,8-triaza-spiro[4.5]dodecan-2-one

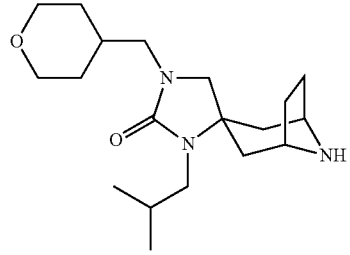

The N1-alkylation of 3-(tetrahydropyran-4-ylmethyl)-bicyclo[3.2.1]-1β,3,8-triaza-spiro[4.5]dodecan-2-one was performed as described in Preparation 2, Step 5 using isobutyl iodide as alkylating agent.

1H NMR (400 MHz, CDCl$_3$): δ [ppm] 3.92 (m, 2H), 3.68 (br s, 2H), 3.40 (m, 1H), 3.34 (dxt, 2H), 3.31 (s, 2H), 3.00 (d, 2H), 2.77 (d, 2H), 2.00 (dxd, 2H), 1.95-1.85 (m, 2H), 1.84-1.67 (m, 5H), 1.53 (m, 2H), 1.32 (dxq, 2H), 0.84 (d, 6H).

Scheme 3

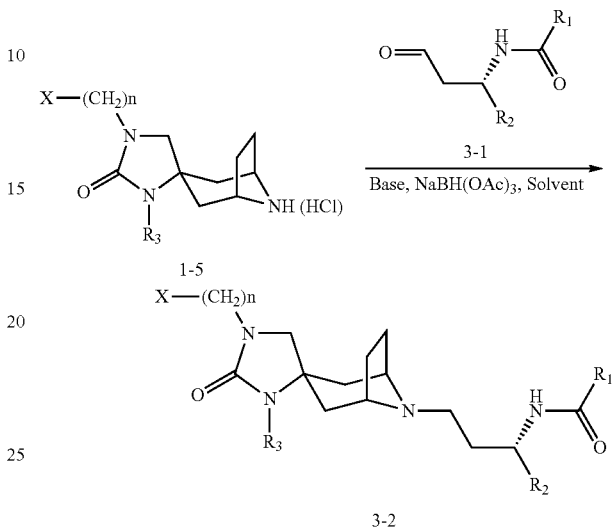

General procedure: The urea 1-5 is coupled to the chiral aldehyde 3-1 using standard reductive amination conditions in solvent such as DCE, toluene or THF at room temperature to yield the compound 3-2.

Example 1

4,4-Difluoro-cyclohexanecarboxylic acid {(S)-3-[1-methyl-3-(tetrahydropyran-4-ylmethyl)-bicyclo[3.2.1]-2-oxo-1β,3,8-triaza-spiro[4.5]dodec-8-yl]-1-phenyl-propyl}-amide hydrochloride

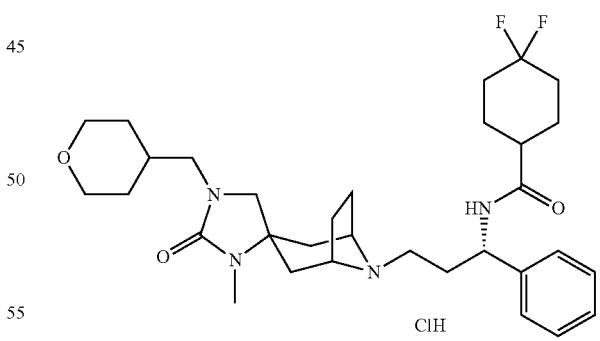

To 21.1 mg (0.072 mmol) of 1-methyl-3-(tetrahydropyran-4-ylmethyl)-bicyclo[3.2.1]-1β,3,8-triaza-spiro[4.5]dodecan-2-one in 1.5 mL of DCE was added 21.2 mg (0.072 mmol, 1 eq.) of 4,4-difluoro-cyclohexanecarboxylic acid ((S)-3-oxo-1-phenyl-propyl)-amide, 19 mg (0.09 mmol, 1.25 eq.) of sodium triacetoxyborohydride and 12 μL (0.086 mmol, 1.2 eq.) of triethylamine. The reaction mixture was stirred overnight at room temperature and concentrated in vacuo. The crude was purified by flash chromatography on silica gel (DCM/MeOH: 0 to 100) and redissolved in 1 mL of methanol and 100 μL of HCl (1N). The solution was then concentrated in vacuo and diluted with 2 mL of water to give after lyophilization 17.5 mg (40%) of 4,4-difluoro-cyclohexanecarboxylic acid {(S)-3-[1-methyl-3-(tetrahydropyran-4-ylmethyl)-bicyclo[3.2.1]-2-oxo-1β,3,8-triaza-spiro[4.5]dodec-8-yl]-1-phenyl-propyl}-amide hydrochloride.

LC/MS: m/z=573.50 (M+H$^+$).

Example 2

Isopropylcarboxylic acid {(S)-3-[1-methyl-3-(tetrahydropyran-4-ylmethyl)-bicyclo[3.2.1]-2-oxo-1β,3,8-triaza-spiro[4.5]dodec-8-yl]-1-phenyl-propyl}-amide

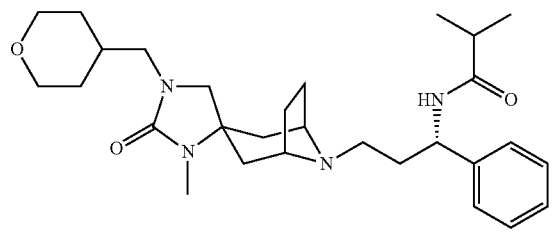

To 86.5 mg (0.295 mmol) of 1-methyl-3-(tetrahydropyran-4-ylmethyl)-bicyclo[3.2.1]-1β,3,8-triaza-spiro[4.5]dodecan-2-one in 3 mL of DCE was added 65 mg (0.296 mmol, 1 eq.) of N-((S)-3-oxo-1-phenyl-propyl)-isobutyramide, 78 mg (0.368 mmol, 1.25 eq.) of sodium triacetoxyborohydride and 49 μL (0.351 mmol, 1.2 eq.) of triethylamine. The reaction mixture was stirred overnight at room temperature, diluted with DCM, washed with a saturated solution of sodium bicarbonate, brine and dried over sodium sulfate. The crude was purified by flash chromatography on silica gel (DCM/MeOH: 0 to 10%) to yield 69.4 mg (47%) of isopropylcarboxylic acid {(S)-3-[1-methyl-3-(tetrahydropyran-4-ylmethyl)-bicyclo[3.2.1]-2-oxo-1β,3,8-triaza-spiro[4.5]dodec-8-yl]-1-phenyl-propyl}-amide.

1H NMR (400 MHz, CDCl$_3$): δ [ppm] 7.33-7.20 (m, 5H), 5.09 (q, 1H), 3.95 (br d×d, 2H), 3.38-3.31 (m, 6H), 3.01 (d, 2H), 2.66 (s, 3H), 2.40-2.30 (m, 3H), 2.11-1.65 (m, 10H), 1.53 (t, 4H), 1.31 (q×d, 2H), 1.13 (d×d, 6H).

Scheme 4

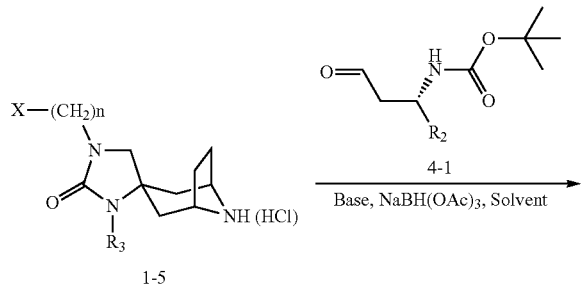

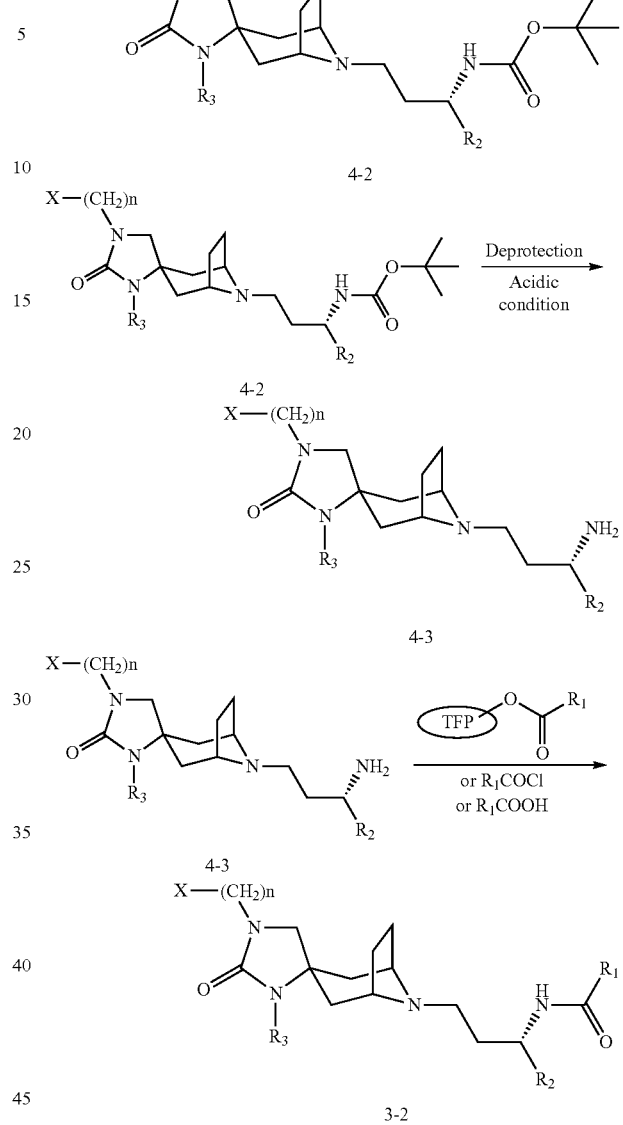

General procedure: The urea 1-5 is coupled to the chiral aldehyde 4-1 using standard reductive amination conditions in solvent such as DCE, toluene or THF at room temperature. Then the Boc compound 4-2 is deprotected under acidic condition and the free amine 4-3 is subsequently condensed with preactivated carboxylic acid R$_1$COOH on polymeric 4-hydroxy-2,3,5,6-tetrafluorobenzamido (TFP) resin (see preparation in J. M. Salvino et al. *J. Comb. Chem.* 2000, 2, 691-697) in solvent such as DMF, or condensed with acid chloride R$_1$COCl in solvent such as DCM in presence of a base such as triethylamine or diisopropylethylamine, or condensed with a carboxylic acid R$_1$COOH in solvents such as DMF, DCM or DCE with coupling agents such as HOBt, DIC, HATU, BOP, PyBOP, or supported coupling agent such as PL-EDC, to provide acylated compound 3-2.

Various carboxylic acids R$_1$COOH for use in scheme 4 can be obtained from commercial sources such as Aldrich or can be obtained by methods well known in the art of chemical synthesis. See, for example: Macromolecular Syntheses, (1982), 8 pp 41-44; J. Med. Chem. (1999) 1576; Arkiv foer Kemi (1966) 26(6), 73-77, Journal of Organic Chemistry (2007) 72, 1174, Tet. Lett. (2001) 42, 8247, Journal of Organic Chemistry (1959) 24, 715; WO 2006/030984; EP (1995) 688752; WO2007/023143; WO 2006/106812; and WO 2000/039125.

Preparation 7

[(S)-3-(1-Isopropyl-3-(tetrahydropyran-4-ylmethyl)-bicyclo[3.2.1]-2-oxo-1β,3,8-triaza-spiro[4.5]dodec-8-yl)-1-phenyl-propyl]-carbamic acid tert-butyl ester

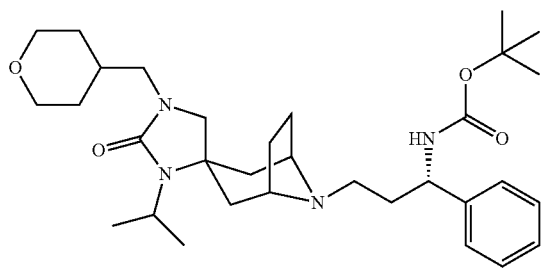

To 500 mg (1.55 mmol) of 1-isopropyl-3-(tetrahydropyran-4-ylmethyl)-bicyclo[3.2.1]-1β,3,8-triaza-spiro[4.5]dodecan-2-one in anhydrous DCE (40 mL) was added 388 mg (1.55 mmol) of ((S)-3-oxo-1-phenyl-propyl)-carbamic acid text-butyl ester and 260 µL (1.86 mmol) of triethylamine. The reaction mixture was stirred for 30 minutes and 412 mg (1.94 mmol) of sodium triacetoxyborohydride was added in one portion. Then the reaction mixture was agitated overnight at room temperature, diluted with DCM, washed with saturated solution of sodium bicarbonate and dried over sodium sulfate. The residue was purified by flash chromatography on silica gel eluting with DCM/Methanol (0 to 8%) to yield 731 mg (85%) of [(S)-3-(1-isopropyl-3-(tetrahydropyran-4-ylmethyl)-bicyclo[3.2.1]-2-oxo-1β,3,8-triaza-spiro[4.5]dodec-8-yl)-1-phenyl-propyl]-carbamic acid tert-butyl ester as a white solid.

Preparation 8

8-((S)-3-Amino-3-phenyl-propyl)-1-isopropyl-3-(tetrahydropyran-4-ylmethyl)-bicyclo[3.2.1]-1β,3,8-triaza-spiro[4.5]dodecane-2-one

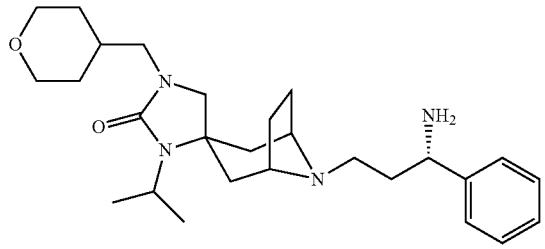

To 730 mg (1.31 mmol) of [(S)-3-(1-isopropyl-3-(tetrahydropyran-4-ylmethyl)-bicyclo[3.2.1]-2-oxo-1β,3,8-triaza-spiro[4.5]dodec-8-yl)-1-phenyl-propyl]-carbamic acid tert-butyl ester in 7.5 mL of anhydrous DCM was added 2.5 mL of TFA. The reaction mixture was stirred at room temperature for 1 hour, diluted with DCM, washed twice with 1N NaOH and dried over sodium sulfate to give, after concentration in vacuo, 600 mg (100%) of 8-((S)-3-amino-3-phenyl-propyl)-1-isopropyl-3-(tetrahydropyran-4-ylmethyl)-bicyclo[3.2.1]-1β,3,8-triaza-spiro[4.5]dodecane-2-one.

LC/MS: m/z=455.47 (M+H$^+$).

Example 3

Isobutyryl acid {(S)-3-[1-isopropyl-3-(tetrahydropyran-4-ylmethyl)-bicyclo[3.2.1]-2-oxo-1β,3,8-triaza-spiro[4.5]dodec-8-yl]-1-phenyl-propyl}-amide hydrochloride

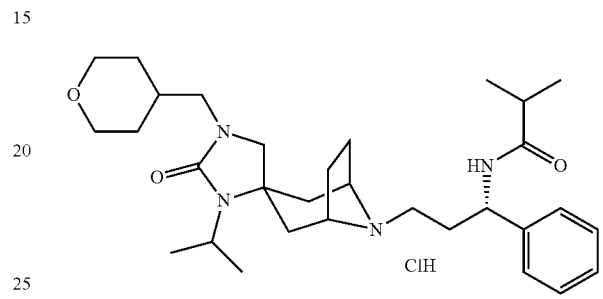

To 50 mg (0.11 mmol) of 8-((S)-3-amino-3-phenyl-propyl)-1-isopropyl-3-(tetrahydropyran-4-ylmethyl)-bicyclo[3.2.1]-1β,3,8-triaza-spiro[4.5]dodecane-2-one in 2 mL of anhydrous DMF was added 24 mg (0.275 mmol) of isobutyric acid followed by 34 µL (0.242 mmol) of triethylamine and 51 mg (0.133 mmol) of HATU. The reaction mixture was stirred for 18 hours at room temperature and concentrated in vacuo. The crude was purified by flash chromatography on silica gel (DCM/MeOH: 0 to 10%) and redissolved in 3 mL of methanol and 5 mL of HCl (5%). The solution was then concentrated in vacuo and diluted with 5 mL of water to give after lyophilization 43 mg (69%) of isobutyryl acid {(S)-3-[1-isopropyl-3-(tetrahydropyran-4-ylmethyl)-bicyclo[3.2.1]-2-oxo-1β,3,8-triaza-spiro[4.5]dodec-8-yl]-1-phenyl-propyl}-amide hydrochloride.

LC/MS: m/z=525.53 (M+H$^+$).

Example 4

Cyclopropanecarboxylic acid {(S)-3-[1-isopropyl-3-(tetrahydropyran-4-ylmethyl)-bicyclo[3.2.1]-2-oxo-1β,3,8-triaza-spiro[4.5]dodec-8-yl]-1-phenyl-propyl}-amide hydrochloride

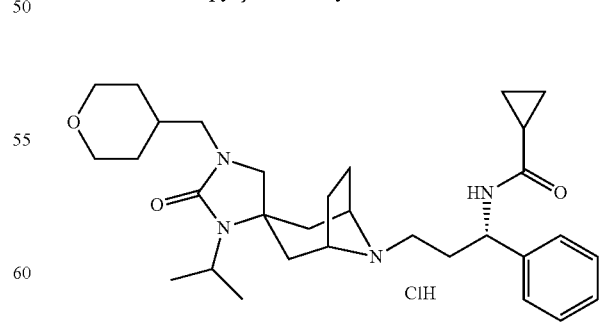

To 50 mg (0.11 mmol) of 8-((S)-3-amino-3-phenyl-propyl)-1-isopropyl-3-(tetrahydropyran-4-ylmethyl)-bicyclo[3.2.1]-1β,3,8-triaza-spiro[4.5]dodecane-2-one in 2 mL of anhydrous DMF was added 24 mg (0.275 mmol) of cyclopropanecarboxylic acid followed by 34 μL (0.242 mmol) of triethylamine and 51 mg (0.133 mmol) of HATU. The reaction mixture was stirred for 18 hours at room temperature and concentrated in vacuo. The crude was purified by flash chromatography on silica gel (DCM/MeOH: 0 to 10%) and redissolved in 3 mL of methanol and 5 mL of HCl (5%). The solution was then concentrated in vacuo and diluted with 5 mL of water to give after lyophilization 37 mg (60%) of cyclopropanecarboxylic acid {(S)-3-[1-isopropyl-3-(tetrahydropyran-4-ylmethyl)-bicyclo[3.2.1]-2-oxo-1β,3,8-triazaspiro[4.5]dodec-8-yl]-1-phenyl-propyl}-amide hydrochloride.

LC/MS: m/z=523.52 (M+H⁺).

Table 1 of compounds illustrates some of the compounds of the present invention which were synthesized using the procedures described in schemes 3 and 4.

TABLE 1

| # | MOLSTRUCTURE | Compound name | m/z (M + H⁺) |
|---|---|---|---|
| 1 | *(structure)* | 4,4-Difluoro-1-methylcyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide hydrochloride | 615.51 |
| 2 | *(structure)* | Isopropylcarboxylic acid {(S)-3-[1-isopropyl-3-(tetrahydropyran-4-ylmethyl)-bicyclo[3.2.1]-2-oxo-1β,3,8-triaza-spiro[4.5]dodec-8-yl]-1-phenyl-propyl}-amide hydrochloride | 525.53 |
| 3 | *(structure)* | 4,4-Difluoro-cyclohexanecarboxylic acid {(S)-3-[3-(tetrahydro-pyran-4-ylmethyl)-bicyclo[3.2.1]-2-oxo-1β,3,8-triaza-spiro[4.5]dodec-8-yl]-1-phenyl-propyl}-amide hydrochloride | 559.48 |
| 4 | *(structure)* | 4,4-Difluoro-cyclohexanecarboxylic acid {(S)-3-[1-methyl-3-(tetrahydro-pyran-4-ylmethyl)-bicyclo[3.2.1]-2-oxo-1β,3,8-triaza-spiro[4.5]dodec-8-yl]-1-phenyl-propyl}-amide hydrochloride | 573.50 |

TABLE 1-continued

| # | MOLSTRUCTURE | Compound name | m/z (M + H+) |
|---|---|---|---|
| 5 | 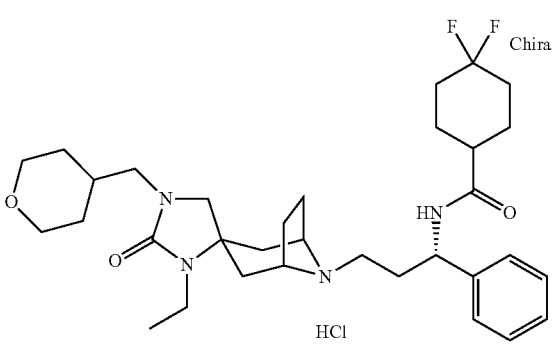 | 4,4-Difluoro-cyclohexanecarboxylic acid {(S)-3-[1-ethyl-3-(tetrahydro-pyran-4-ylmethyl)-bicyclo[3.2.1]-2-oxo-1β,3,8-triaza-spiro[4.5]dodec-8-yl]-1-phenyl-propyl}-amide hydrochloride | 587.51 |
| 6 | 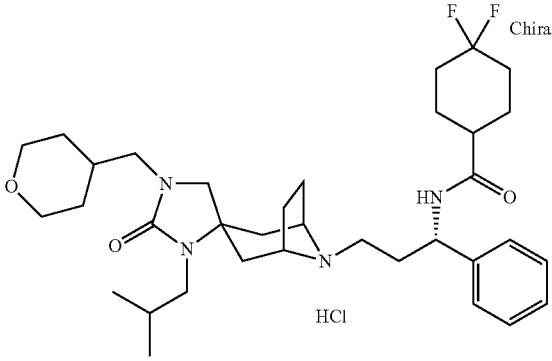 | 4,4-Difluoro-cyclohexanecarboxylic acid {(S)-3-[1-isobutyl-3-(tetrahydro-pyran-4-ylmethyl)-bicyclo[3.2.1]-2-oxo-1β,3,8-triaza-spiro[4.5]dodec-8-yl]-1-phenyl-propyl}-amide hydrochloride | 615.56 |
| 7 | 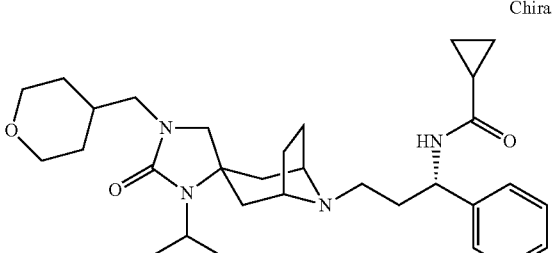 | Cyclopropylcarboxylic acid {(S)-3-[1-isopropyl-3-(tetrahydropyran-4-ylmethyl)-bicyclo[3,2,1]-2-oxo-1β,3,8-triaza-spiro[4.5]dodec-8-yl]-1-phenyl-propyl}-amide hydrochloride | 523.52 |
| 8 | 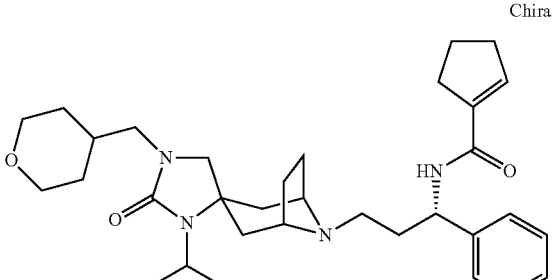 | Cyclopent-1-enecarboxylic acid {(S)-3-[1-isopropyl-3-(tetrahydropyran-4-ylmethyl)-bicyclo[3.2.1]-2-oxo-1β,3,8-triaza-spiro[4.5]dodec-8-yl]-1-phenyl-propyl}-amide hydrochloride | 549.54 |

TABLE 1-continued

| # | MOLSTRUCTURE | Compound name | m/z (M + H+) |
|---|---|---|---|
| 9 | 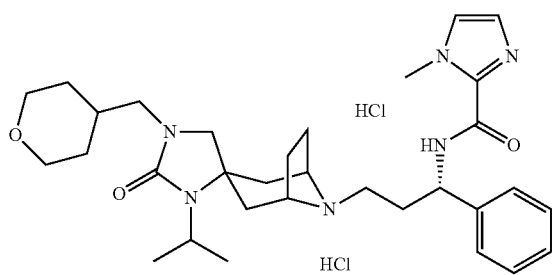 Chiral | 1-Methyl-1H-imidazole-2-carboxylic acid{(S)-3-[1-isopropyl-3-(tetrahydropyran-4-ylmethyl)-bicyclo[3.2.1]-2-oxo-1β,3,8-triaza-spiro[4.5]dodec-8-yl]-1-phenyl-propyl}-amide dihydrochloride | 563.51 |
| 10 | 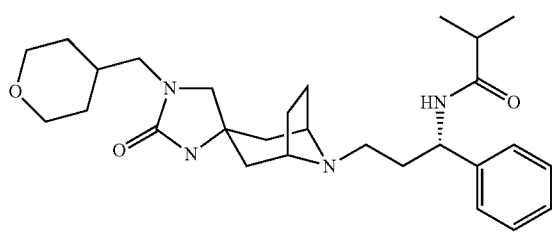 Chiral | Isopropylcarboxylic acid {(S)-3-[3-(tetrahydropyran-4-ylmethyl)-bicyclo[3.2.1]-2-oxo-1β,3,8-triaza-spiro[4.5]dodec-8-yl]-1-phenyl-propyl}-amide | 483.47 |
| 11 | 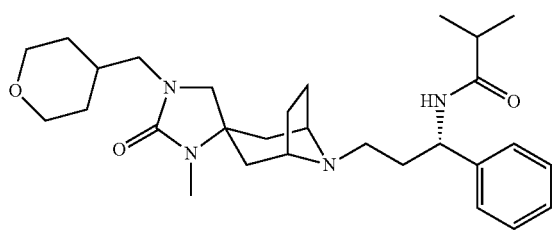 Chiral | Isopropylcarboxylxc acid {(S)-3-[1-methyl-3-(tetrahydropyran-4-ylmethyl)-bicyclo[3.2.1]-2-oxo-1β,3,8-triaza-spiro[4.5]dodec-8-yl]-1-phenyl-propyl}-amide | 497.40 |
| 12 | 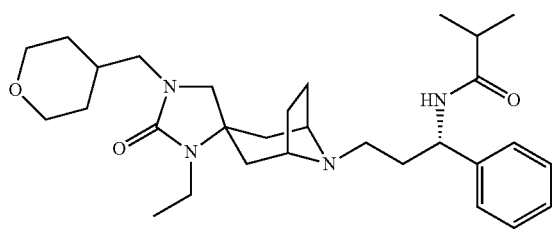 Chiral | Isopropylcarboxylic acid {(S)-3-[1-ethyl-3-(tetrahydropyran-4-ylmethyl)-bicyclo[3.2.1]-2-oxo-1β,3,8-triaza-spiro[4.5]dodec-8-yl]-1-phenyl-propyl}-amide | 511.51 |
| 13 | 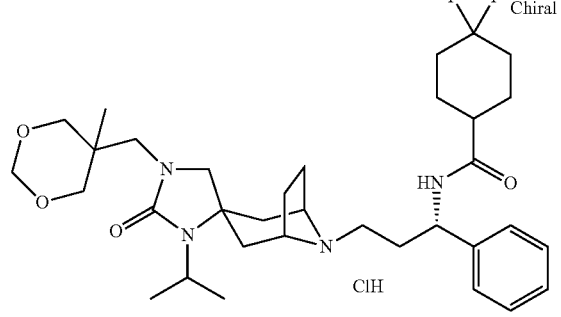 Chiral | 4,4-Difluoro-cyclohexanecarboxylic acid {(S)-1-isopropyl-3-(5-methyl-[1,3]dioxan-5-ylmethyl)-bicyclo[3.2.1]-2-oxo-1β,3,8-triaza-spiro[4.5]dodec-8-yl]-1-phenyl-propyl}-amide hydrochloride | 617.58 |

Table 2 of compounds illustrates additional compounds of Formula I of the present invention.

TABLE 2

| | | | | |
|---|---|---|---|---|
| 14 | 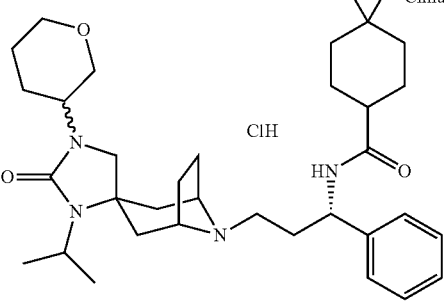 | | 4,4-Difluoro-cyclohexanecarboxylic acid {(S)-3-[1-isopropyl-3-(tetrahydropyran-3-yl)-bicyclo[3.2.1]-2-oxo-1-triaza-spiro[4.5]dodec-8-yl]-1-phenyl-propyl}-amide hydrochloride | 587.52 |
| 15 | 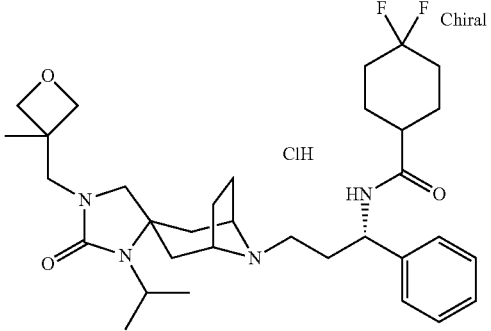 | | 4,4-Difluoro-cyclohexanecarboxylic acid {(S)-3-[1-isopropyl-3-{3-methyl-oxetan-3-ylmethyl)-bicyclo[3.2.1]-2-oxo-1β,3,8-triaza-spiro[4.5]dodec-8-yl]-1-phenyl-propyl}-amide hydrochloride | 587.47 |
| 16 | 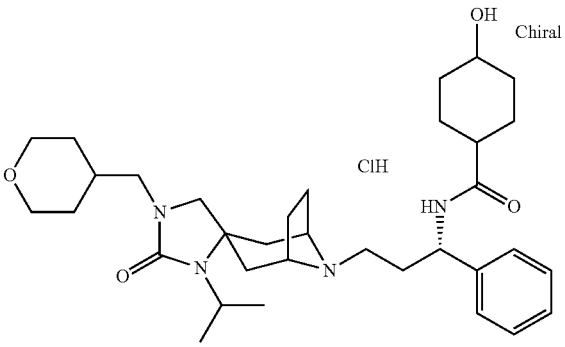 | | 4-Hydroxy-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide hydrochloride | 581.62 |
| 17 | 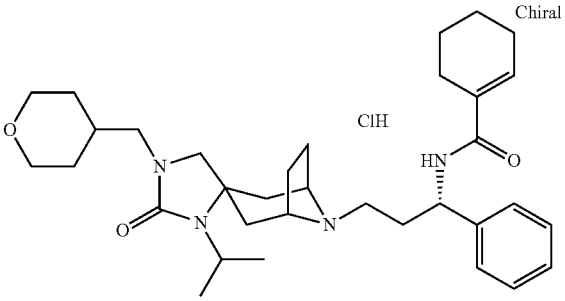 | | Cyclohex-1-enecarboxylic acid {(S)-3-1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide hydrochloride | 563.59 |

TABLE 2-continued

| # | Structure | | Name | MW |
|---|---|---|---|---|
| 18 | | Chiral, ClH | N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-2-trifluoromethyl-acrylamide hydrochloride | 577.54 |
| 19 | | Chiral, ClH | N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-2-methyl-acrylamlde hydrochloride | 523.55 |
| 20 | | Chiral, ClH | 2-Ethyl-N-{(S)-3-[1-isopropyl-3-(tetrahydro-pyran-4-ylmethyl}-bicyclo[3.2.1]-2-oxo-1β,3,8-triaza-spiro[4.5]dodec-8-yl]-1-phenyl-propyl}-butyramide hydrochloride | 553.61 |
| 21 | | Chiral, ClH | N-{(S)[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-propionamide hydrochloride | 511.55 |
| 22 | | Chiral, ClH | 4,4-Difluoro-cyclohexanecarboxylic acid {(S)-3-[3-(5-methyl-[1,3]dioxan-5-ylmethyl)-bicyclo[3.2.1]-2-oxo-1β,3,8-triaza-spiro[4.5]dodec-8-yl]-1-phenyl-propyl}-amide hydrochloride | 575.56 |

TABLE 2-continued

| # | Structure | | Name | MW |
|---|---|---|---|---|
| 23 | 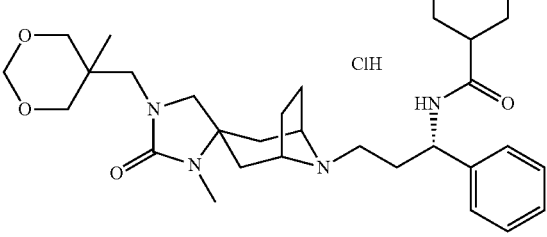 | Chiral | 4,4-Difluoro-cyclohexanecarboxylic acid {(S)-3-[1-methyl-3-(5-methyl-[1,3]dioxan-5-ylmethyl)-bicyclo[3.2.1]-2-oxo-1β,3,8-triaza-spiro[4.5]dodec-8-yl]-1-phenyl-propyl}-amide hydrochloride | 589.62 |
| 24 | 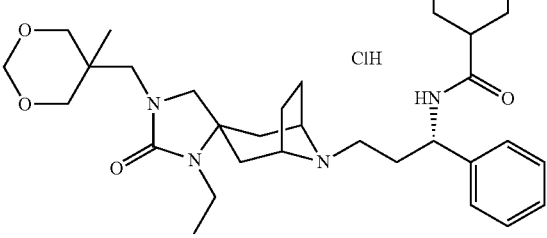 | Chiral | 4,4-Difluoro-cyclohexanecarboxylic acid {(S)-3-[1-ethyl-3-(5-methyl-[1,3]dioxan-5-ylmethyl)-bicyclo[3.2.1]-2-oxo-1β,3,8-triaza-spiro[4.5]dodec-8-yl]-1-phenyl-propyl}-amide hydrochloride | 603.64 |
| 25 | 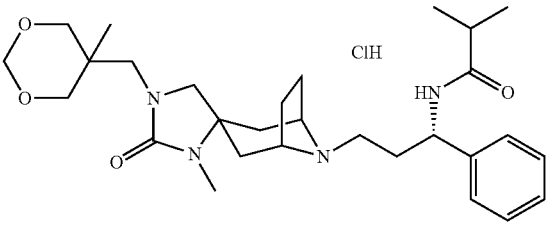 | Chiral | N-{(S)-3-[1-methyl-3-(5-methyl-[1,3]dioxan-5-ylmethyl)-bicyclo[3.2.1]-2-oxo-1β,3,-triaza-spiro[4.5]dodec-8-yl]-1-phenyl-propyl}-isobutyramide hydrochloride | 513.57 |
| 26 | 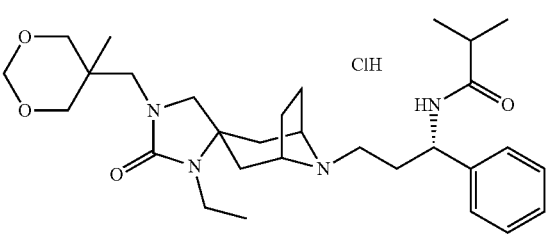 | Chiral | N-{(S)-3-[1-ethyl-3-(5-methyl-[1,3]dioxan-5-ylmethyl)-bicyclo[3.2.1]-2-oxo-1β,3,-triaza-spiro[4.5]dodec-8-yl]-1-phenyl-propyl}-isobutyramide hydrochloride | 527.58 |
| 27 | 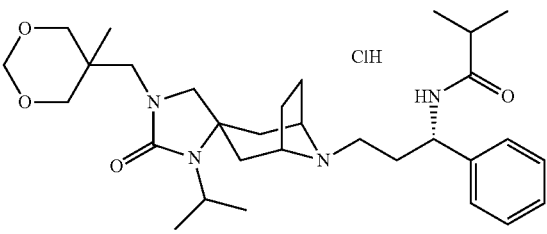 | Chiral | N-{(S)-3-[1-isopropyl-3-(5-methyl-[1,3]dioxan-5-ylmethyl)-bicyclo[3.2.1]-2-oxo-1β,3,-triaza-spiro[4.5]dodec-8-yl]-1-phenyl-propyl}-isobutyramide hydrochloride | 541.54 |

TABLE 2-continued

| | | | | |
|---|---|---|---|---|
| 28 | 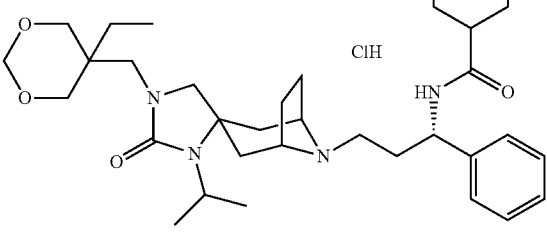 | Chiral | 4,4-Difluoro-cyclohexanecarboxylic acid {(S)-3-[1-isopropyl-3-(5-ethyl-[1,3]dioxan-5-ylmethyl)-bicyclo{3.2.1]-2-oxo-1β,3,8-triaza-spiro[4.5]dodec-8-yl]-1-phenyl-propyl}-amide hydrochloride | 631.67 |
| 29 | 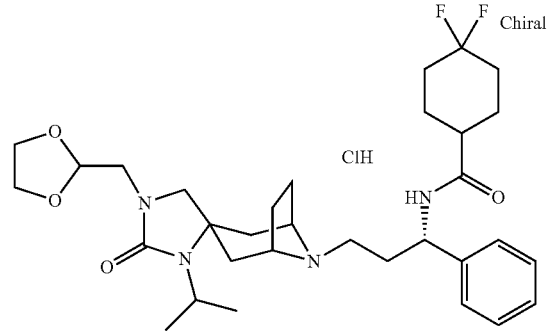 | Chiral | 4,4-Difluoro-cyclohexanecarboxylic acid {(S)-3-[3-([1,3]dioxolan-2-ylmethyl)-1-isopropyl-bicyclo[3.2.1]-2-oxo-1β,3,8-triaza-spiro[4.5]dodec-8-yl]-1-phenyl-propyl}-amide hydrochloride | 589.57 |
| 30 | 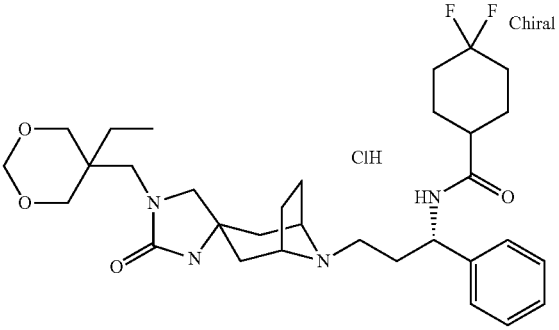 | Chiral | 4,4-Difluoro-cyclohexanecarboxylic acid {(S)-3-[3-(5-ethyl-[1,3]dioxan-5-ylmethyl)-bicyclo[3.2.1]-2-oxo-1β,3,8-triaza-spiro[4.5]dodec-8-yl]-1-phenyl-propyl}-amide hydrochloride | 589.7 |
| 31 | 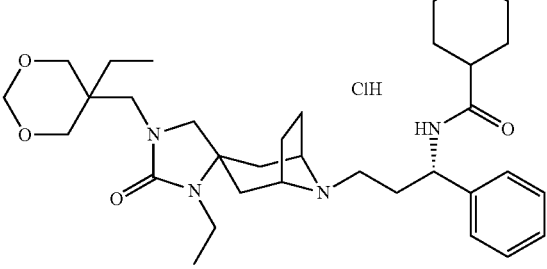 | Chiral | 4,4-Difluoro-cyclohexanecarboxylic acid {(S)-3-[1-ethyl-3-(5-ethyl-[1,3]dioxan-5-ylmethyl)-bicyclo[3.2.1]-2-oxo-1β,3,8-triaza-spiro[4.5]dodec-8-yl]-1-phenyl-propyl}-amide hydrochloride | 617.76 |

TABLE 2-continued

| # | Structure | | Name | MW |
|---|---|---|---|---|
| 32 | | Chiral, ClH | N-{(S)-3-[1-ethyl-3-(5-ethyl-[1,3]dioxan-5-ylmethyl)-bicyclo[3.2.1]-2-oxo-1β,3,8-triaza-spiro[4.5]dodec-8-yl]-1-phenyl-propyl}-isobutyramide hydrochloride | 541.69 |
| 33 | | Chiral | {(S)-3-[1-isopropyl-3-{tetrahydro-pyran-4-ylmethyl)-bicyclo[3.2.1]-2-oxo-1β,3,8-triaza-spiro[4.5]dodec-8-yl]-1-phenyl-propyl}-carbamic acid methyl ester | 513.54 |
| 34 | | Chiral | {(S)-3-[1-isopropyl-3-(tetrahydro-pyran-4-ylmethyl)-bicyclo[3.2.1]-2-oxo-1β,3,8-triaza-spiro[4,5]dodec-8-yl]-1-phenyl-propyl}-carbamic acid ethyl ester? | 527.56 |
| 35 | | Chiral | {(S)-3-[1-isopropyl-3-(tetrahydro-pyran-4-ylmethyl}-bicyclo[3.2.1]-2-oxo-1β,3,8-triaza-spiro[4.5]dodec-8-yl]-1-phenyl-propyl}-carbamic acid isopropyl ester | 541.58 |
| 36 | | Chiral, ClH | Cis-4-hydroxy-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide hydrochloride | 581.65 |

TABLE 2-continued

| | | | | |
|---|---|---|---|---|
| 37 | 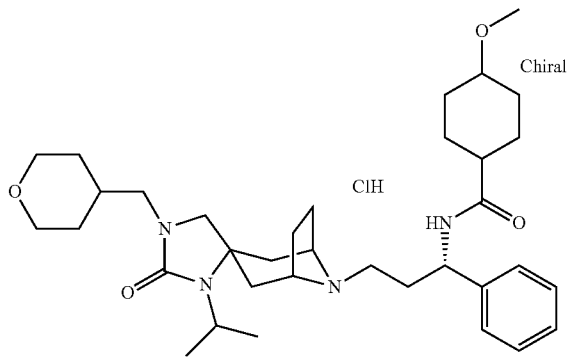 | Chiral ClH | 4-Methoxy-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide hydrochloride | 595.66 |
| 38 | 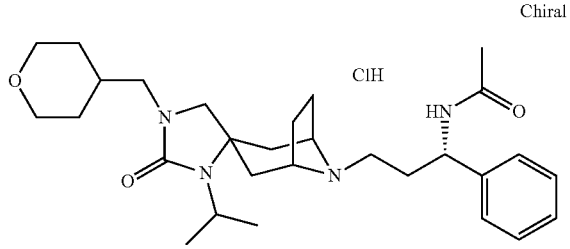 | Chiral ClH | N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-acetamide hydrochloride | 497.55 |
| 39 | 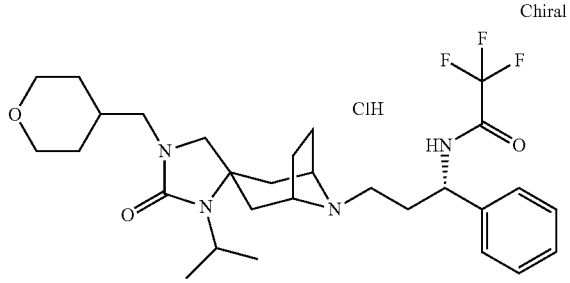 | Chiral ClH | 2,2,2-Trifluoro-N-{(S)-3-[1-isopropyl-3-(tetrahydro-pyran-4-ylmethyl)-bicyclo[3,2.1]-2-oxo-1β,3,8-triaza-spiro[4.5]dodec-8-yl]-1-phenyl-propyl}-acetamide hydrochloride | 553.62 |
| 40 | 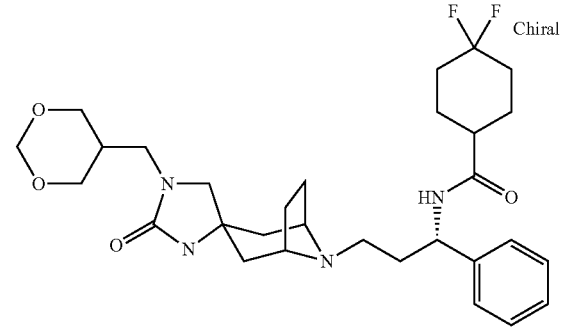 | Chiral | 4,4-Difluoro-cyclohexanecarboxylic acid {(S)-3-[3-([1,3]dioxan-5-ylmethyl)-bicyclo[3,2.1]-2-oxo-1β,3,8-triaza-spiro[4.5]dodec-8-yl]-1-phenyl-propyl}-amide | 561.49 |
| 41 | 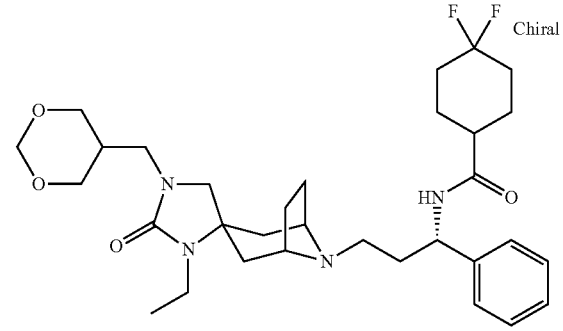 | Chiral | 4,4-Difluoro-cyclohexanecarboxylic acid {(S)-3-[1-ethyl-3-([1,3]dioxan-5-ylmethyl)-bicyclo[3.2.1]-2-oxo-1β,3,8-triaza-spiro[4.5]dodec-8-yl]-1-phenyl-propyl}-amide | 589.58 |

TABLE 2-continued

| | | | | |
|---|---|---|---|---|
| 42 | 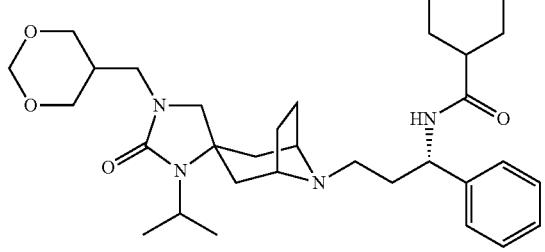 | Chiral | 4,4-Difluoro-cyclohexanecarboxylic acid {(S)-3-[1-isopropyl-3-([1,3]dioxan-5-ylmethyl)-bicyclo[3.2.1]-2-oxo-1β,3,8-triaza-spiro[4.5]dodec-8-yl]-1-phenyl-propyl}-amide | 603.54 |
| 43 | 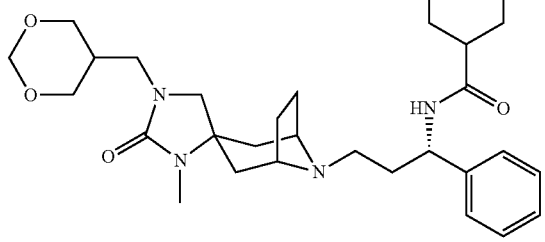 | Chiral | 4,4-Difluoro-cyclohexanecarboxylic acid {(S)-3-[1-methyl-3-([1,3]dioxan-5-ylmethyl)-bicyclo[3.2.1]-2-oxo-1β,3,8-triaza-spiro[4.5]dodec-8-yl]-1-phenyl-propyl}-amide | 575.55 |
| 44 | 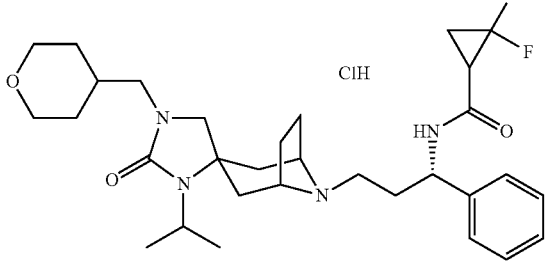 | Chiral ClH | 2,2-Difluoro-cyclopropanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-3-yl]-1-phenyl-propyl}-amide hydrochloride | 559.46 |
| 45 | 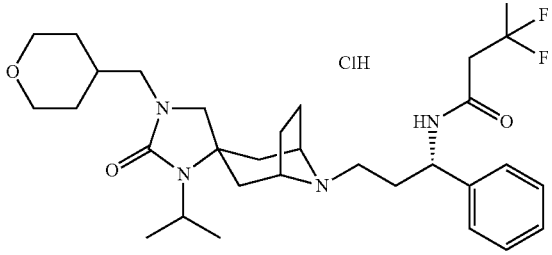 | Chiral ClH | 3,3,3-Trifluoro-N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-propionamide hydrochloride | 565.31 |
| 46 | 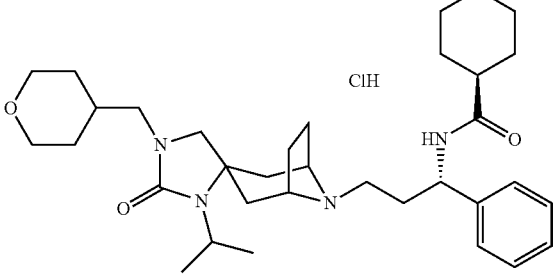 | Chiral ClH | Trans-4-hydroxy-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide hydrochloride | 581.5 |

TABLE 2-continued

| | | | | |
|---|---|---|---|---|
| 47 | 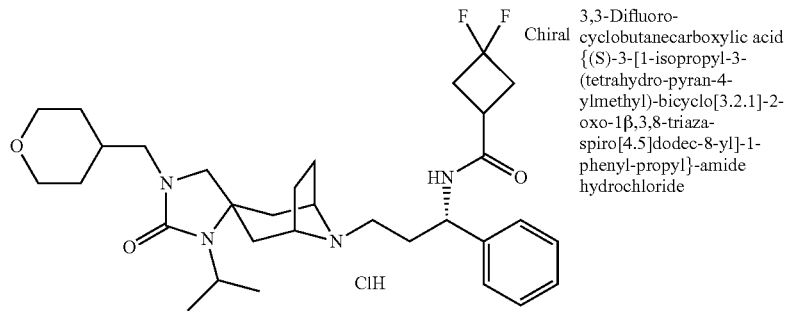 | Chiral | 3,3-Difluoro-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide hydrochloride | 573.57 |
| 48 | 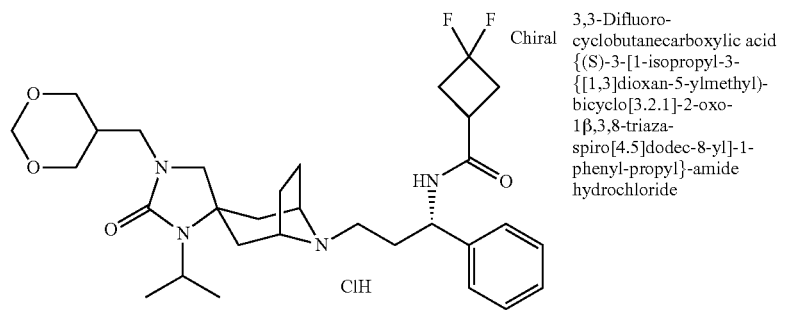 | Chiral | 3,3-Difluoro-cyclobutanecarboxylic acid {(S)-3-[1-isopropyl-3-{[1,3]dioxan-5-ylmethyl)-bicyclo[3.2.1]-2-oxo-1β,3,8-triaza-spiro[4.5]dodec-8-yl]-1-phenyl-propyl}-amide hydrochloride | 575.51 |
| 49 | 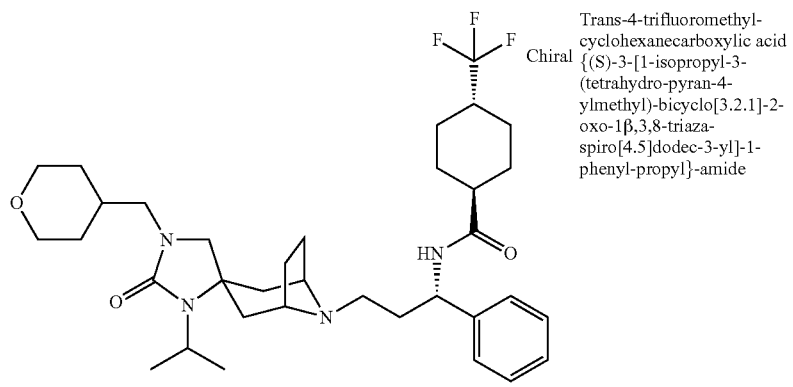 | Chiral | Trans-4-trifluoromethyl-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-3-yl]-1-phenyl-propyl}-amide | |
| 50 | 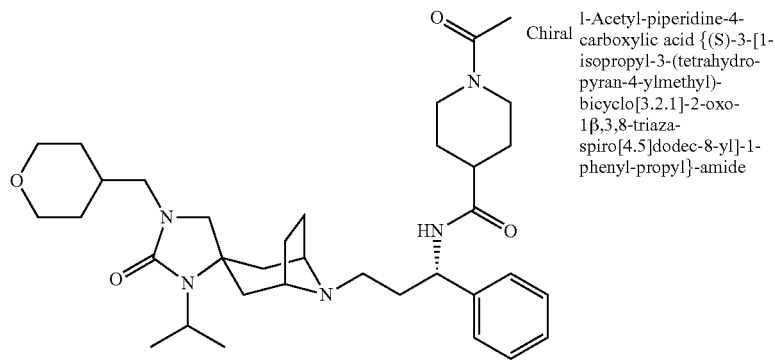 | Chiral | 1-Acetyl-piperidine-4-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide | |

TABLE 2-continued

| | | | |
|---|---|---|---|
| 51 | 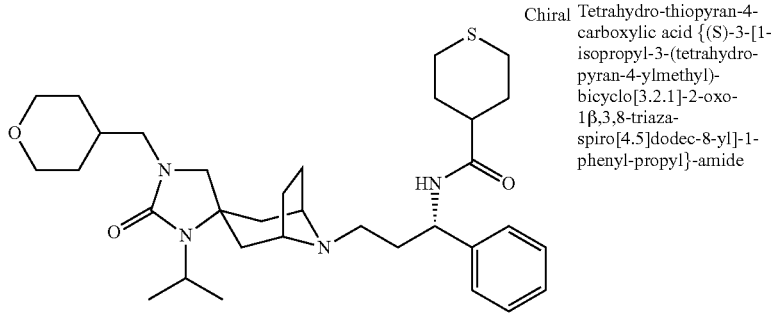 | Chiral | Tetrahydro-thiopyran-4-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 52 | 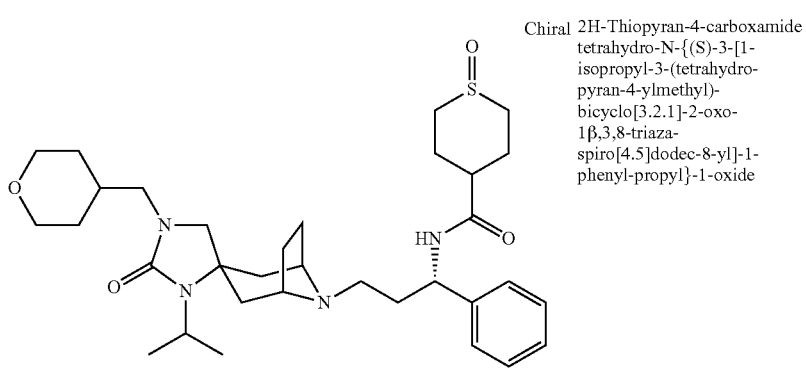 | Chiral | 2H-Thiopyran-4-carboxamide tetrahydro-N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-1-oxide |
| 53 | 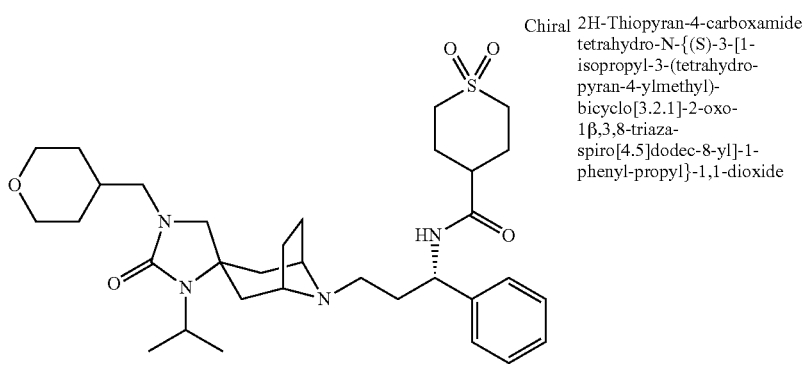 | Chiral | 2H-Thiopyran-4-carboxamide tetrahydro-N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-1,1-dioxide |
| 54 | 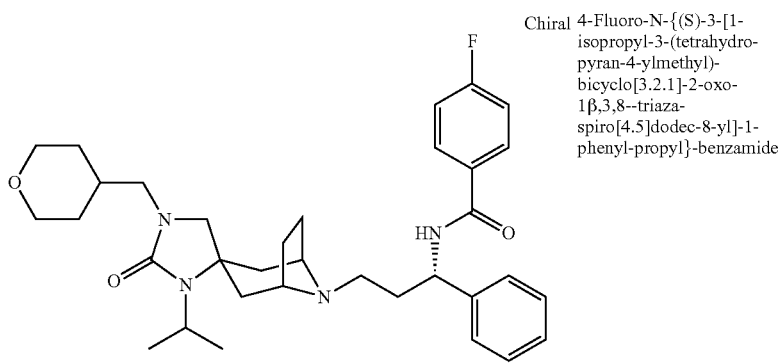 | Chiral | 4-Fluoro-N-{(S)-3-[1-isopropyl-3-(tetrahydro-pyran-4-ylmethyl)-bicyclo[3.2.1]-2-oxo-1β,3,8--triaza-spiro[4.5]dodec-8-yl]-1-phenyl-propyl}-benzamide |

TABLE 2-continued

| | | | |
|---|---|---|---|
| 55 | 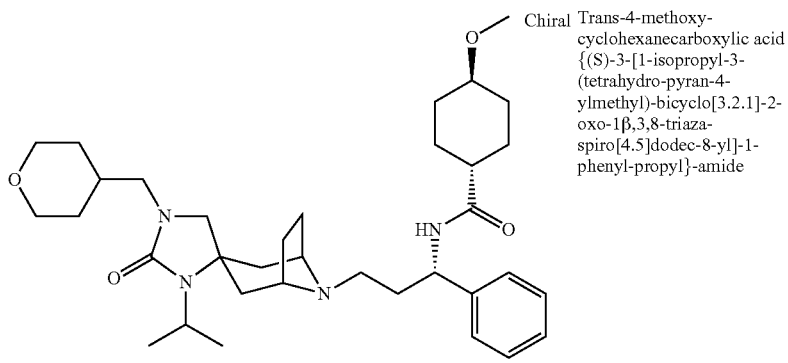 | Chiral | Trans-4-methoxy-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 56 | 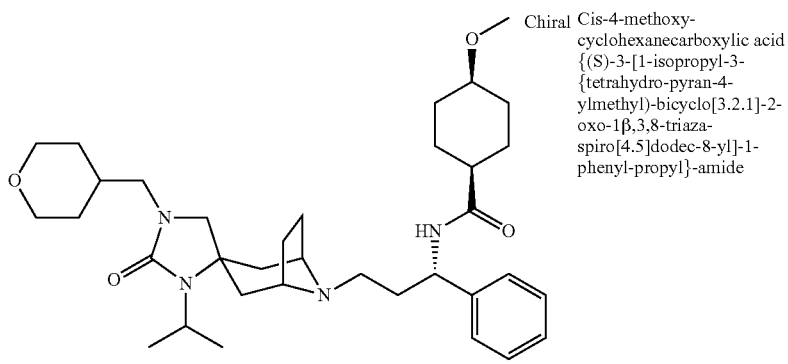 | Chiral | Cis-4-methoxy-cyclohexanecarboxylic acid {(S)-3-[1-isopropyl-3-{tetrahydro-pyran-4-ylmethyl)-bicyclo[3.2.1]-2-oxo-1β,3,8-triaza-spiro[4.5]dodec-8-yl]-1-phenyl-propyl}-amide |
| 57 | 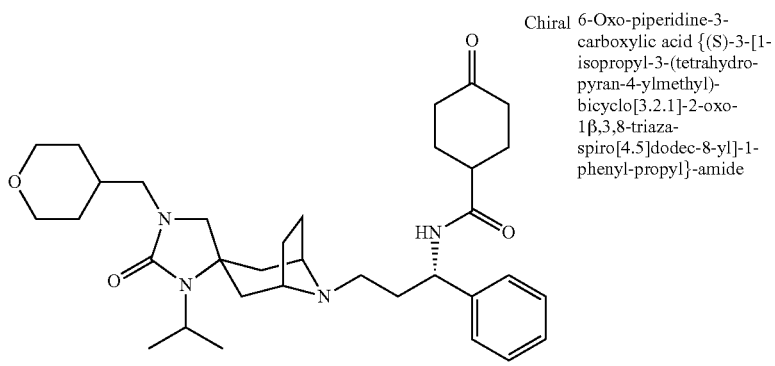 | Chiral | 6-Oxo-piperidine-3-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 58 | 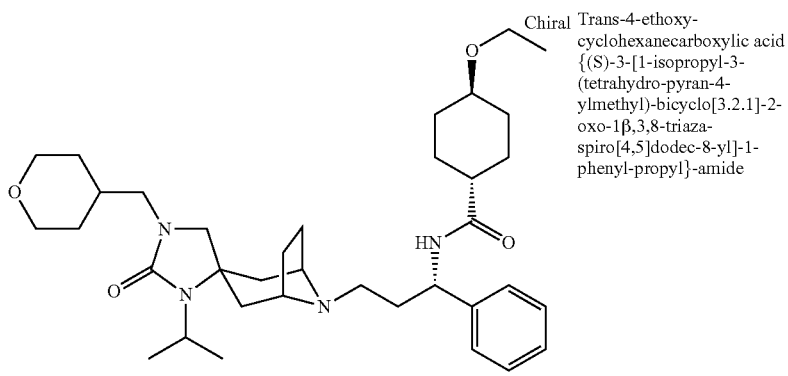 | Chiral | Trans-4-ethoxy-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |

TABLE 2-continued

| | | | |
|---|---|---|---|
| 59 | 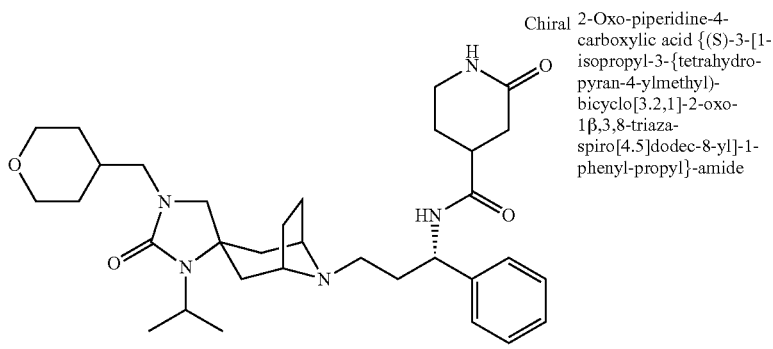 | Chiral | 2-Oxo-piperidine-4-carboxylic acid {(S)-3-[1-isopropyl-3-{tetrahydro-pyran-4-ylmethyl)-bicyclo[3.2.1]-2-oxo-1β,3,8-triaza-spiro[4.5]dodec-8-yl]-1-phenyl-propyl}-amide |
| 60 | 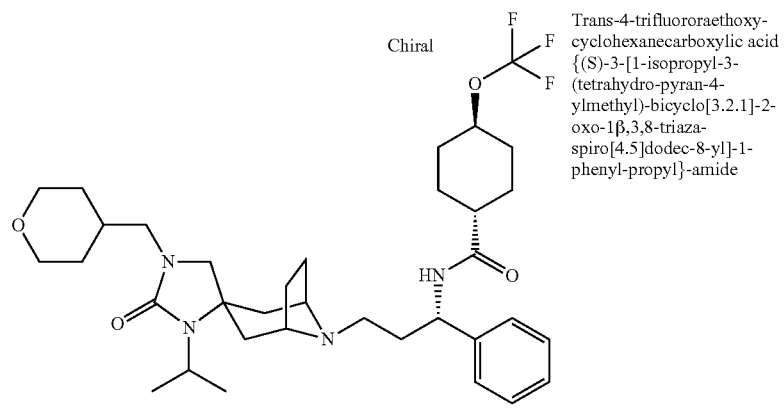 | Chiral | Trans-4-trifluororaethoxy-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 61 | 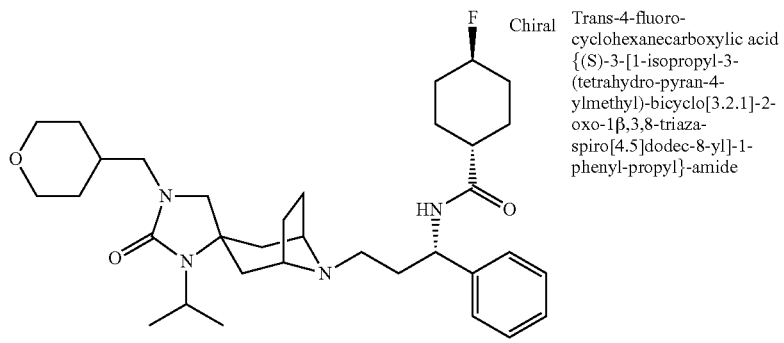 | Chiral | Trans-4-fluoro-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 62 | 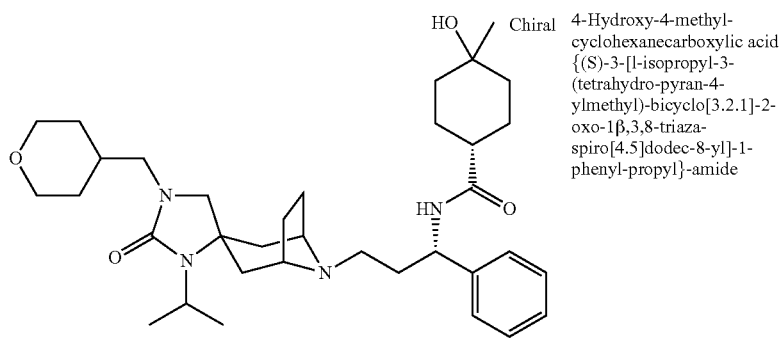 | Chiral | 4-Hydroxy-4-methyl-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |

TABLE 2-continued

| | | | |
|---|---|---|---|
| 63 | 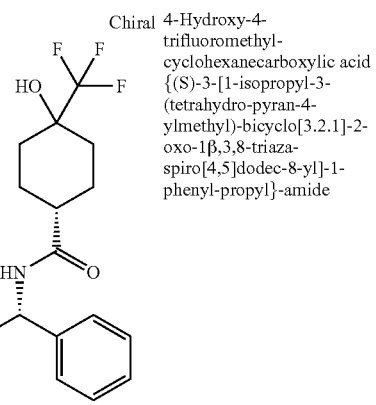 | Chiral | 4-Hydroxy-4-trifluoromethyl-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4,5]dodec-8-yl]-1-phenyl-propyl}-amide |
| 64 | 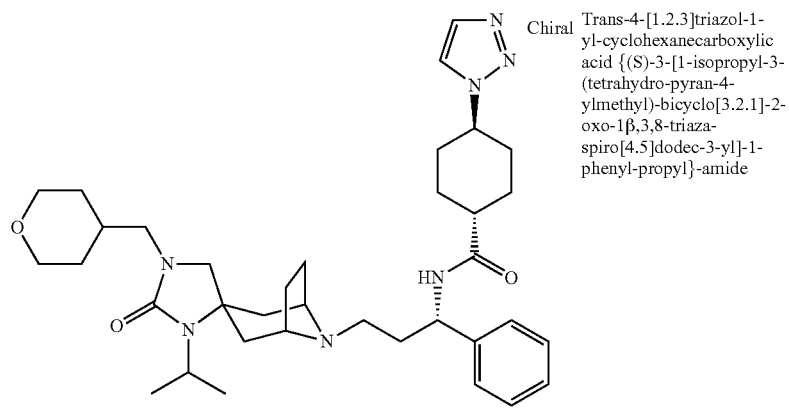 | Chiral | Trans-4-[1.2.3]triazol-1-yl-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-3-yl]-1-phenyl-propyl}-amide |
| 65 | 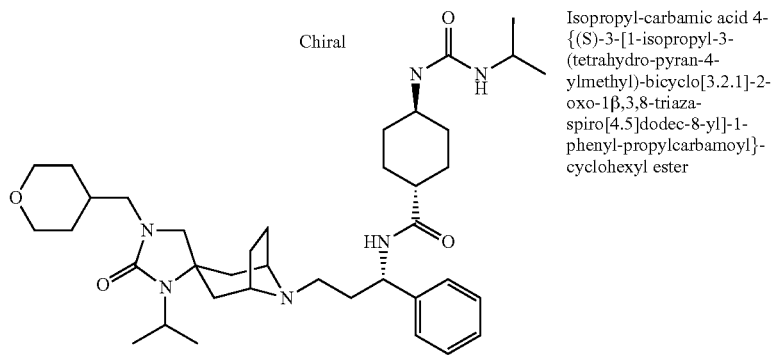 | Chiral | Isopropyl-carbamic acid 4-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propylcarbamoyl}-cyclohexyl ester |
| 66 | 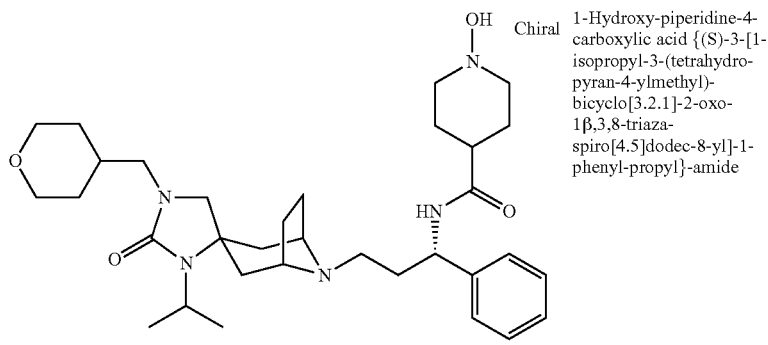 | Chiral | 1-Hydroxy-piperidine-4-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |

TABLE 2-continued

| 67 | 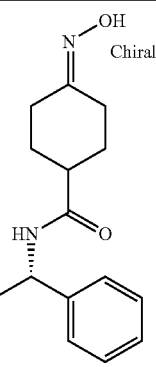 | 4-Hydroxyimino cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| --- | --- | --- |
| 68 | 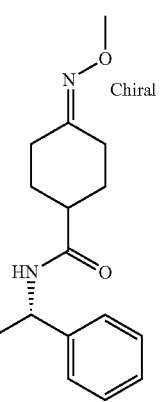 | 4-Methoxyimino-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 69 | 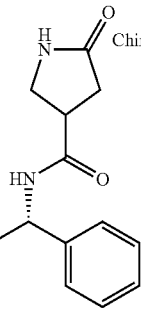 | 5-Oxo-pyrrolidine-3-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 70 | 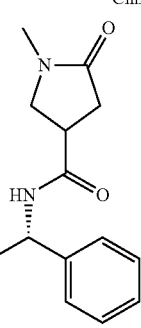 | 1-Methyl-5-oxo-pyrrolidine-3-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |

TABLE 2-continued

| | | | |
|---|---|---|---|
| 71 | 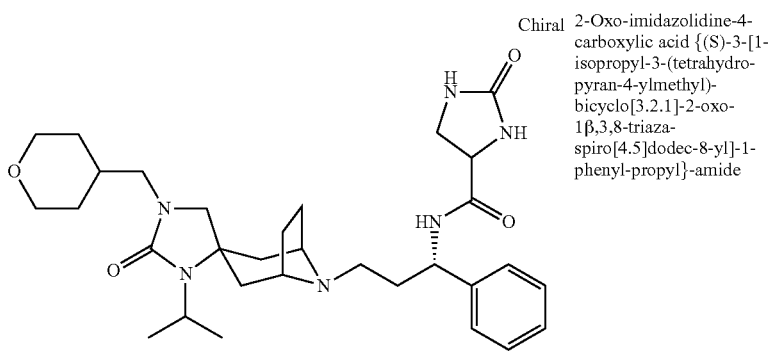 | Chiral | 2-Oxo-imidazolidine-4-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 72 | 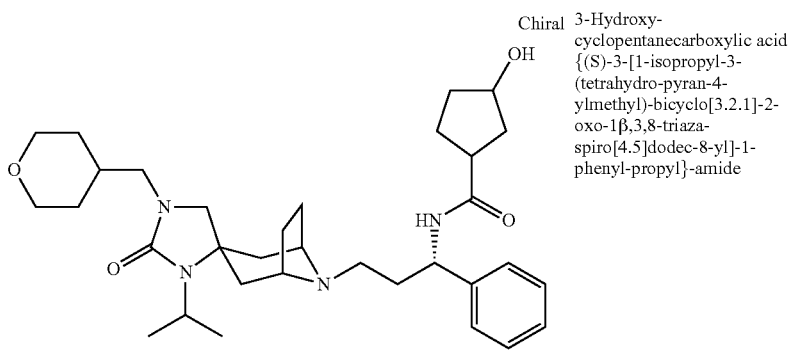 | Chiral | 3-Hydroxy-cyclopentanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 73 | 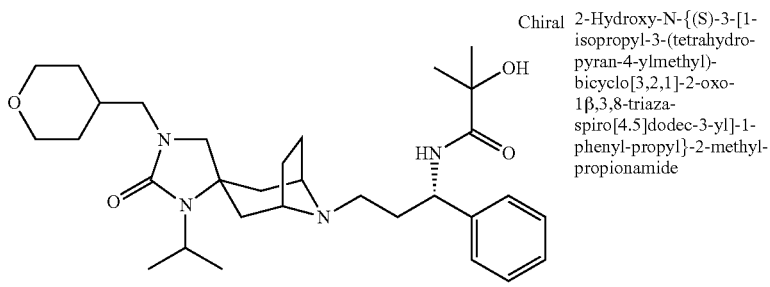 | Chiral | 2-Hydroxy-N-{(S)-3-[1-isopropyl-3-(tetrahydro-pyran-4-ylmethyl)-bicyclo[3,2,1]-2-oxo-1β,3,8-triaza-spiro[4.5]dodec-3-yl]-1-phenyl-propyl}-2-methyl-propionamide |
| 74 | 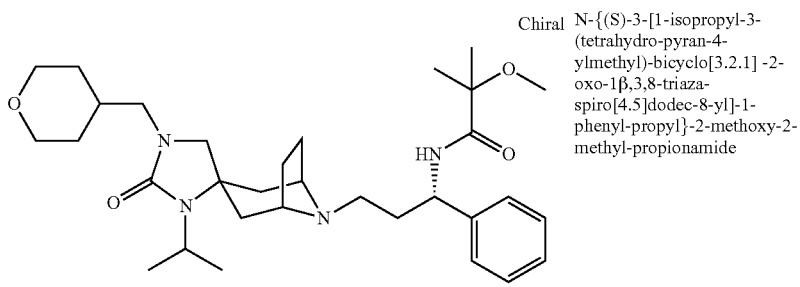 | Chiral | N-{(S)-3-[1-isopropyl-3-(tetrahydro-pyran-4-ylmethyl)-bicyclo[3.2.1] -2-oxo-1β,3,8-triaza-spiro[4.5]dodec-8-yl]-1-phenyl-propyl}-2-methoxy-2-methyl-propionamide |
| 75 | 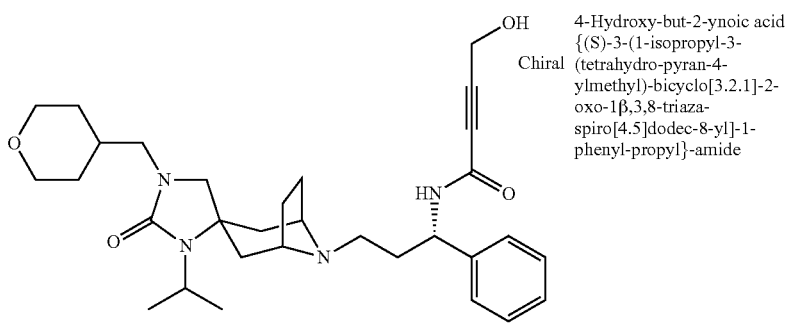 | Chiral | 4-Hydroxy-but-2-ynoic acid {(S)-3-(1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |

TABLE 2-continued

| # | Structure | Name |
|---|---|---|
| 76 | 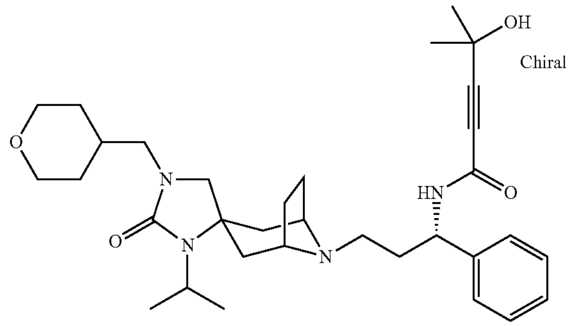 | 4-Hydroxy-4-methyl-pent-2-ynoic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-l-phenyl-propyl}-amide |
| 77 | 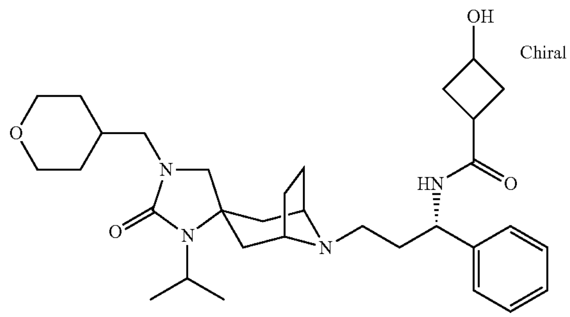 | 3-Hydroxy-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| 78 | 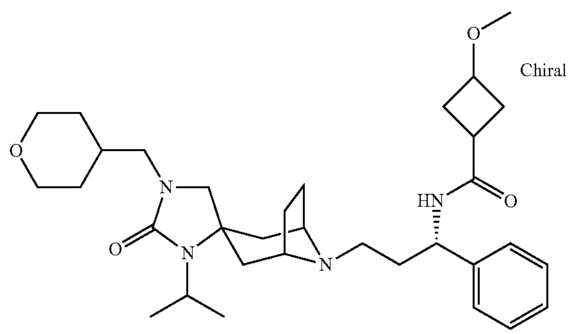 | 3-Methoxy-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4,5]dodec-8-yl]-1-phenyl-propyl}-amide |
| 79 | 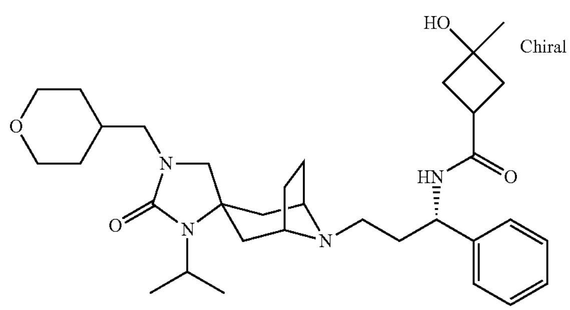 | 3-Hydroxy-3-methyl-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4,5]dodec-8-yl]-phenyl-propyl}-amide |
| 80 | 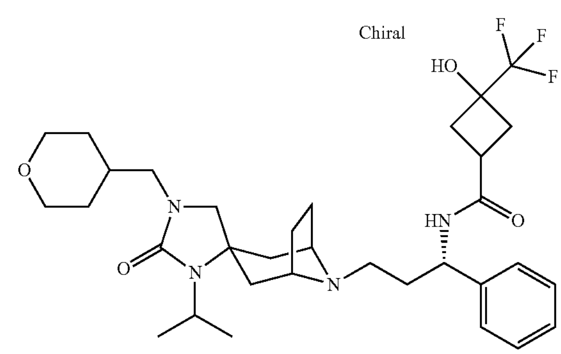 | 3-Hydroxy-3-trifluoromethyl-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |

TABLE 2-continued

| 81 | 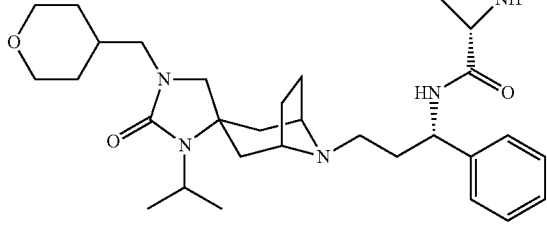 | (S)-4-Oxo-azetidine-2-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |
| --- | --- | --- |
| 82 | 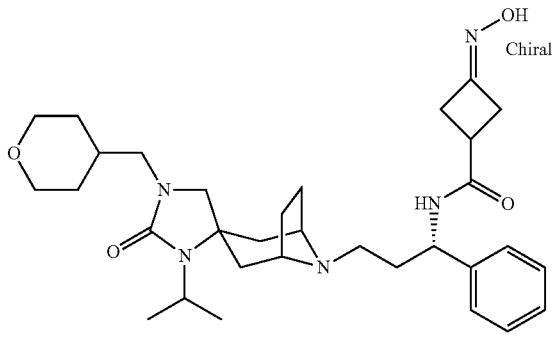 | 3-Hydroxyimino-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-3-yl]-1-phenyl-propyl}-amide |
| 83 | 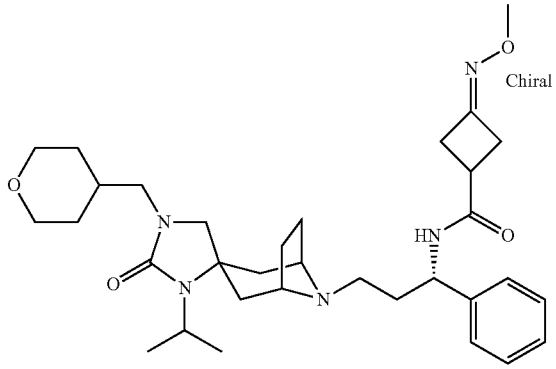 | 3-Methoxyimino-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-phenyl-propyl}-amide |
| 84 | 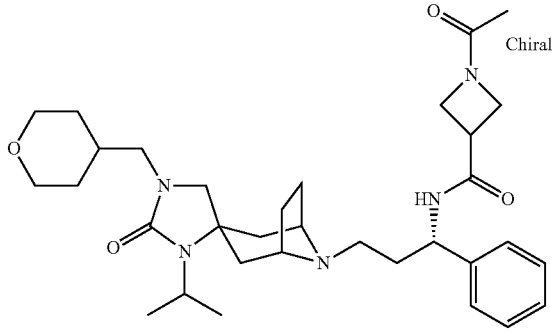 | 1-Acetyl-azetidine-3-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |

TABLE 2-continued

| 85 | 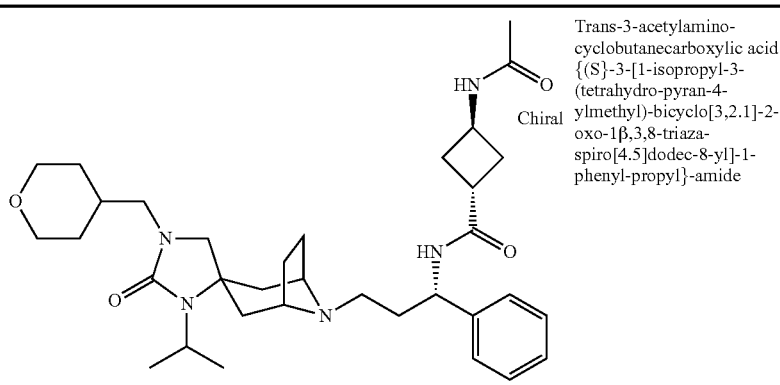 | Trans-3-acetylamino-cyclobutanecarboxylic acid {(S)-3-[1-isopropyl-3-(tetrahydro-pyran-4-ylmethyl)-bicyclo[3,2.1]-2-oxo-1β,3,8-triaza-spiro[4.5]dodec-8-yl]-1-phenyl-propyl}-amide |
| --- | --- | --- |
| 86 | 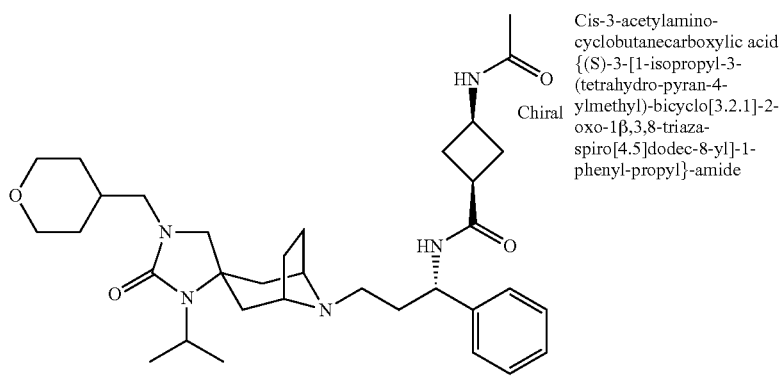 | Cis-3-acetylamino-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide |

Example 5

Chemokine Binding assay: Membranes (1 µg/well) from human embryonic kidney (HEK-293) cells expressing human CCR5 are incubated with 0.1 nM $^{125}$I-labeled MIP-1α (Amersham) in the presence of varying concentrations of a test compound (10000-0.01 nM) in buffer (50 mM Hepes, pH 7.3/5 mM MgCl$_2$/1 mM CaCl$_2$/0.5% BSA) for 90 min at room temperature. Reaction mixtures (100 µL) are filtered through Multiscreen GFB filters (Millipore) and washed six times with cold wash buffer (50 mM Hepes, pH 7.3/0.5 M NaCl, 0.1% BSA). Bound $^{125}$I-MIP-1α is quantitated by liquid scintillation counting. The nonspecific binding of $^{125}$I-labeled MIP-1α to the membrane is determined based on the radioactivity from the wells added with 100 nM non-radiolabeled MIP-1α. $IC_{50}$ and $K_D$ values are calculated by using GRAPH-PAD PRISM software (Intuitive Software for Science, San Diego).

HIV-1 Replication in PBMC Cultures. Isolated PBMC are stimulated in vitro with 5 µg/ml phytohemagglutinin and 50 units/ml IL-2 for 3 days. The cells are resuspended at 4×10$^6$/ml in complete medium (RPMI, 10% FBS/50 units/ml IL-2), seeded into 96-well plates (2×10$^5$/well), incubated with inhibitor for 1 h at 37° C., and infected in triplicate with 25-100 tissue culture 50% infective dose (TCID$_{50}$) per well of the R5 HIV-1$_{JR-FL}$ strain for 3-4 h. The cells are washed twice in PBS to remove residual virus and cultured in the presence of inhibitor for 4-6 days. HIV-1 replication is determined by the presence of viral RT activity in harvested supernatant fluid. The $IC_{50}$ values for the virus are determined by using GRAPHPAD PRISM software.

HIV-1 Replication in PBMC Cultures: Lymphoprep™-Isolated human PBMC are stimulated in vitro with 2 µg/ml phytohemagglutinin for three days. The cells are infected at a MOI of 1.0 for 3 h and then ished twice with complete media to remove residual virus. The cells are then resuspended at 1.6×10$^6$/ml in complete medium (RPMI, 10% FBS, 1% sodium pyruvate, 25 units/ml IL-2), and seeded into 96-well plates (2.0×10$^5$/well). The cells are cultured in the presence or absence of various concentrations of test compounds in serial dilutions for 4 days at 37° C. After 4 days, 100 µL of cultured medium is replaced with 120 µL of fresh medium containing the test compound. The level of HIV-1 replication is determined at days 6 after infection by the presence of viral RT activity in harvested supernatant fluid. The $IC_{50}$ and $IC_{90}$ values for the virus replication are determined by using GRAPHPAD PRISM software.

HIV-1 Replication in PM1 cell line: The cells are infected at a MOI of 0.5 for 3 h and then ished twice with complete media to remove residual virus. Cells are then resuspended at 0.5×10$^6$/ml in complete medium (RPMI, 10% FBS, 1% sodium pyruvate), and seeded into 96-well plates (6.25×10$^4$/well). The cells are cultured in the presence or absence of various concentrations of test compounds in serial dilutions for 4 days at 37° C. After 4 days, 100 µL of cultured medium with cells are replaced with 120 µL of fresh medium containing the test compound. The level of HIV-1 replication is determined at days 6 after infection by the presence of viral RT activity in harvested supernatant fluid. The $IC_{50}$ and $IC_{90}$ values for the virus replication are determined by using GRAPHPAD PRISM software.

The following reaction schemes and Preparation examples relate to the procedures for preparing compounds of Formula III.

Scheme 5

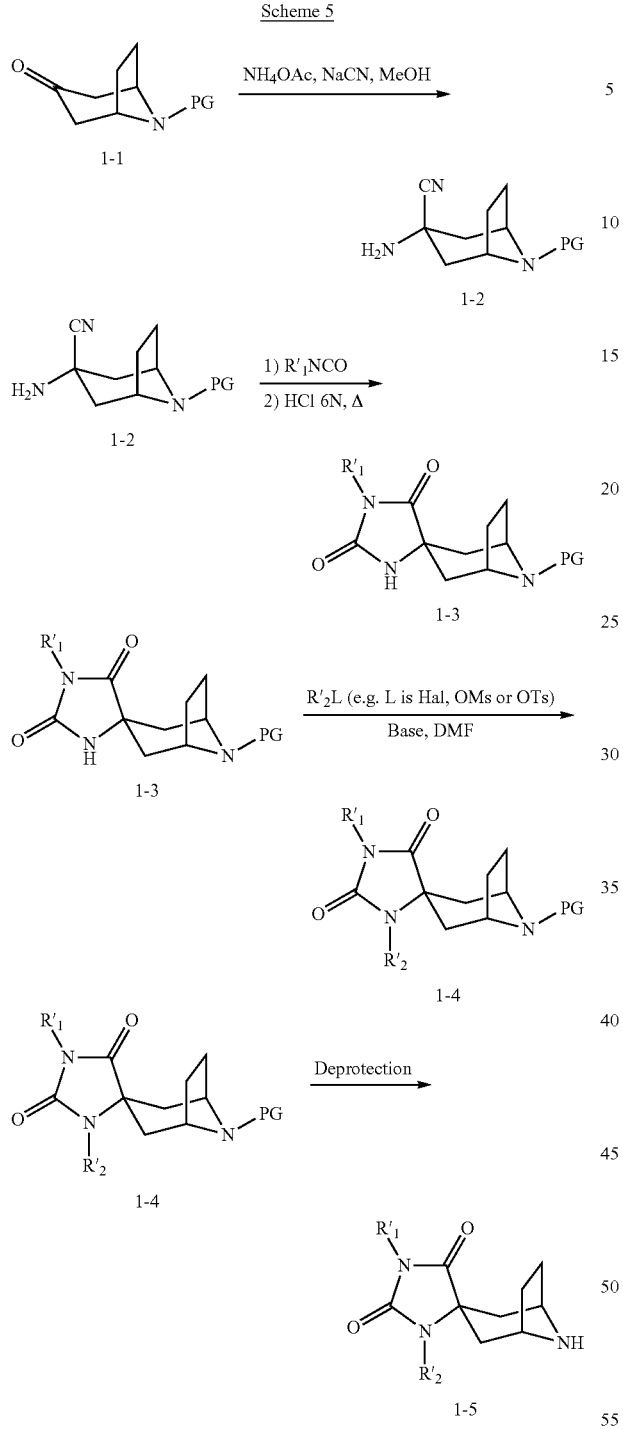

General procedure: N-PG-Nortropinone 1-1 is treated with ammonium acetate and sodium cyanide in methanol at room temperature to yield the regioisomeric aminonitrile 1-2 which is subsequently coupled to isocyanate R₁NCO in polar solvent such as DCM. The urea intermediate is heated under reflux with aqueous hydrochloric acid solution (6N) to give the hydantoin 1-3. Further N1-alkylation takes place by treating the hydantoin 1-3 with a strong base such as KH, NaH or LiH and an electrophile R'₂L (L is an appropriate leaving group such as halogen (Hal), OMs or OTs) in aprotic solvent such as DMF, NMP, DMAC or DMSO at temperature between 20 and 100° C. Then N1 and N3 bisalkylated hydantoin 1-4 is finally deprotected using standards procedures of hydrogenolysis or acidic treatment depending on the nature of the protecting group (PG).

Preparation 9

1-Isopropyl-3-(4-methoxy-phenyl)-bicyclo[3.2.1]-1β,3,8-triaza-spiro[4.5]dodecan-2,4-dione

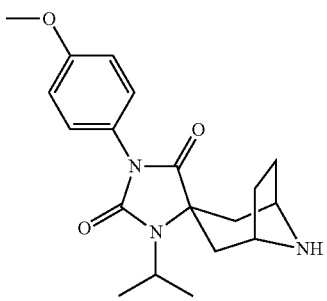

Step 1: To 400 g (1.846 mol) of 8-benzyl-8-aza-bicyclo[3.2.1]octan-3-one in 2000 mL of methanol was added successively 1149 g (14.768 mol, 8 eq.) of ammonium acetate and 110 g (2.25 mol, 1.15 eq.) of sodium cyanide. The reaction was stirred for 28.5 hours at room temperature. Then, 2000 mL of DCM and 1000 mL of water was added successively. The mixture was stirred for 5 minutes. After separation of the organic layer, the aqueous layer was extracted with 2000 mL of DCM. The organic layers were dried over sodium sulfate, filtered and evaporated in vacuo to yield 450 g (95%) of pale yellow solid containing 3β-amino-8-benzyl-8-aza-bicyclo[3.2.1]-octane-3-carbonitrile and 8-benzyl-8-aza-bicyclo-[3.2.1]octan-3-one, respectively, in a ratio of 90:10 as determined by 1H NMR.

Step 2: To 3 g (12.5 mmol) of 3β-amino-8-benzyl-8-aza-bicyclo[3.2.1]-octane-3-carbonitrile previously dissolved in 63 mL of DCM was added 3.2 mL (24.9 mmol, 2 eq.) of 1-isocyanato-4-methoxy-benzene. The reaction mixture was stirred overnight at room temperature. The white precipitate was filtered off and washed with DCM to yield 2.75 g (56%) of 8-benzyl-3-cyano-3β-(4-methoxy-phenyl)-8-aza-bicyclo[3.2.1]-octane urea as a white solid.

Step 3: To 2.75 g (7 mmol) of 8-benzyl-3-cyano-3β-(4-methoxy-phenyl)-8-aza-bicyclo[3.2.1]-octane urea was added 35 mL of HCl 6N. The reaction mixture was heated at 110° C. for 2 hours then cooled to room temperature. The mixture was quenched with NaOH 3N and extracted with ethyl acetate (2×150 mL). The combined organic layers were dried over sodium sulfate to yield after evaporation in vacuo 2.31 g (85%) of 8-benzyl-3-(4-methoxy-phenyl)-bicyclo[3.2.1]-1β,3,8-triaza-spiro[4.5]dodecan-2,4-dione as a white foam.

Step 4: To 2.31 g (5.9 mmol) of 8-benzyl-3-(4-methoxy-phenyl)-bicyclo[3.2.1]-1β,3,8-triaza-spiro[4.5]dodecan-2,4-dione dissolved in 30 mL of anhydrous DMF was added 708 mg (17.7 mmol, 3 eq.) of sodium hydride (60% dispersion in mineral oil). The reaction mixture was agitated for 30 minutes at room temperature before adding 2.35 mL (23.6 mmol, 4 eq.) of 2-iodopropane. The mixture was heated for 18 hours at 60° C. and cooled to room temperature. 150 mL of ethyl acetate were added and the organic layer was washed with water (3×100 mL), brine (100 mL) and dried over sodium sulfate. The crude material was purified by flash chromatography on silica gel (ethyl acetate: hexanes 0 to 100%) to give 1.5 g (59%) of 8-benzyl-1-isopropyl-3-(4-methoxy-phenyl)-bicyclo[3.2.1]-1β,3,8-triaza-spiro[4.5]dodecan-2,4-dione as a white solid.

Step 5: To 109 mg (1.72 mmol) of ammonium formate and 50 mg of palladium hydroxide placed in a 5 mL microwave tube was added 250 mg (0.57 mmol) of 8-benzyl-1-isopropyl-3-(4-methoxy-phenyl)-bicyclo[3.2.1]-1β,3,8-triaza-spiro[4.5]dodecan-2,4-dione previously dissolved in 4 mL of ethanol. The tube was sealed, subjected to microwaves for 3 minutes at 120° C. and cooled to room temperature. The reaction mixture was filtered through celite, rinsed with ethanol and concentrated in vacuo to yield 200 mg (100%) of 1-isopropyl-3-(4-methoxy-phenyl)-bicyclo[3.2.1]-1β,3,8-triaza-spiro[4.5]dodecan-2,4-dione as a colorless oil.

1H NMR (400 MHz, DMSO-d$_6$): δ [ppm] 7.18 (d, 2H), 6.95 (d, 2H), 4.33 (br s, 1H), 3.74 (s, 3H), 3.67 (sept., 1H), 3.43 (br s, 2H), 2.03 (q, 2H), 1.91-1.80 (m, 4H), 1.56 (m, 2H), 1.34 (d, 6H).

Preparation 10

1-Isopropyl-3-(3-methoxy-phenyl)-bicyclo[3.2.1]-1β,3,8-triaza-spiro[4.5]dodecan-2,4-dione

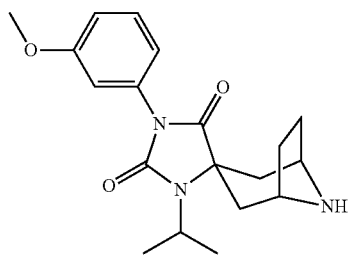

The compound was obtained using essentially the same procedure described in Preparation 9 Steps 2, 3, 4 and 5) except that 3-methoxyphenyl isocyanate was used in Step 2.

1H NMR (400 MHz, DMSO-d$_6$): δ [ppm] 7.32 (t, 1H), 6.93-6.84 (m, 3H), 4.32 (br s, 1H), 3.73 (s, 3H), 3.68 (sept., 1H), 3.49 (br s, 2H), 2.04 (q, 2H), 1.92-1.83 (m, 4H), 1.59 (m, 2H), 1.34 (d, 6H).

Preparation 11

1-Isopropyl-3-(2-methoxy-phenyl)-bicyclo[3.2.1]-1β,3,8-triaza-spiro[4.5]dodecan-2,4-dione

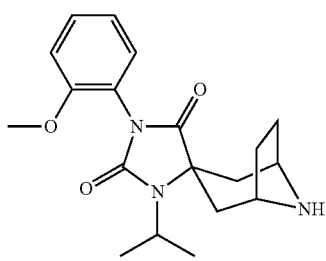

The compound was obtained using essentially the same procedure described in Preparation 9 Steps 2, 3, 4 and 5) except that 2-methoxyphenyl isocyanate was used in Step 2.

1H NMR (400 MHz, DMSO-d$_6$): δ [ppm] 7.38 (t×d, 1H), 7.15 (d×d, 1H), 7.10 (d×d, 1H), 6.97 (t×d, 1H), 4.32 (br s, 1H), 3.71 (s, 3H), 3.63 (sept., 1H), 3.50 (br s, 2H), 2.03-1.89 (m, 4H), 1.83 (d, 1H), 1.74 (d, 1H), 1.59 (m, 2H), 1.33 (d, 6H).

Preparation 12

1-Isopropyl-3-(tetrahydropyran-4-yl)-bicyclo[3.2.1]-1β,3,8-triaza-spiro[4.5]dodecan-2,4-dione

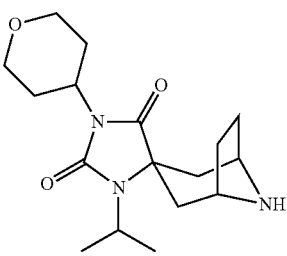

The compound was obtained using essentially the same procedure described in Preparation 9 (Steps 2, 3, 4 and 5) except that 4-isocyanato-tetrahydro-pyran was used in Step 2.

1H NMR (400 MHz, CDCl$_3$): δ [ppm] 4.02 (br s, 1H), 3.89 (m, 3H), 3.59 (br s, 2H), 3.53 (m, 1H), 3.27 (m, 2H), 2.35 (m, 2H), 2.23 (m, 2H), 1.94 (m, 2H), 1.69 (m 4H), 1.42 (m, 2H), 1.31 (d, 6H).

Scheme 6

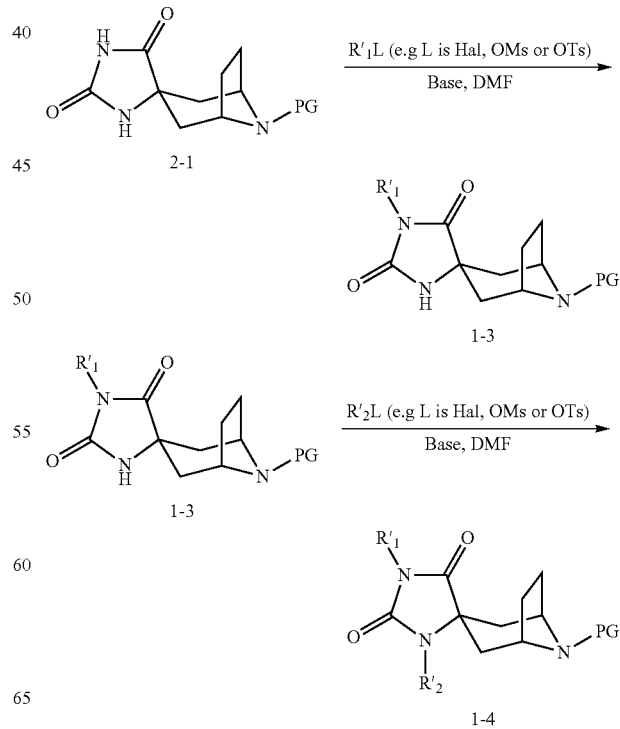

-continued

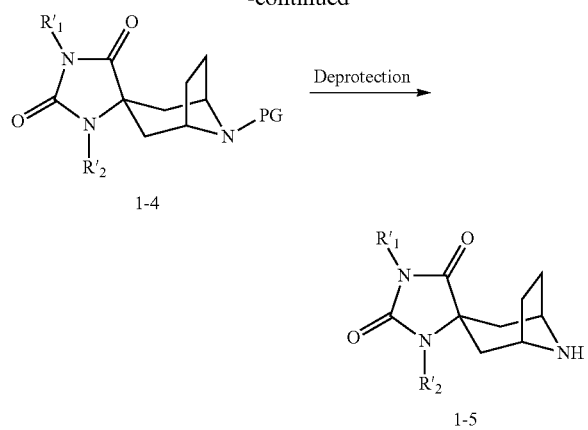

General procedure: The N8-PG-bicyclo[3.2.1]-1β,3,8-triaza-spiro[4.5]dodecan-2,4-dione 2-1 is treated with a base such as Na$_2$CO$_3$, K$_2$CO$_3$, Cs$_2$CO$_3$, LiH, NaH or KH and an electrophile R'$_1$L (L is an appropriate leaving group such as halogen (Hal), OMs or OTs) in polar solvent such as DMF at temperature between 20 to 100° C. to yield the hydantoin 1-3. Further N1-alkylation takes place by treating the hydantoin 1-3 with a strong base such as KH, NaH or LiH and an electrophile R'$_2$L (L is an appropriate leaving group such as halogen (Hal), OMs or OTs) in aprotic solvent such as DMF, NMP, DMAC or DMSO at temperature between 20 and 100° C. Then N1 and N3 bisalkylated hydantoin 1-4 is finally deprotected using standards procedures of hydrogenolysis or acidic treatment depending on the nature of the protecting group (PG).

Preparation 13

Methanesulfonic acid tetrahydropyran-4-ylmethyl ester

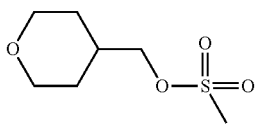

A solution of 90 g (774.8 mmol) of tetrahydropyran-4-methanol and 129.6 mL (929.76 mmol, 1.2 eq.) of triethylamine in 775 mL of anhydrous DCM was cooled to 0° C. in an ice bath. Methanesulfonyl chloride (66.2 mL, 852.28 mmol, 1.1 eq.) was then added dropwise over 60 minutes while maintaining the temperature around 0° C. The reaction mixture was stirred for 30 minutes at 0° C. and quenched with a saturated solution of sodium bicarbonate (800 mL). The aqueous layer was extracted with DCM (800 mL). The combined organic layers were washed with water (2×800 mL), brine (800 mL) and dried over sodium sulfate. After filtration and concentration in vacuo, a yellowish solid (146.1 g, 97%) was obtained corresponding to the methanesulfonic acid tetrahydropyran-4-ylmethyl ester.

1H NMR (400 MHz, DMSO-d$_6$): δ [ppm] 4.02 (d, 2H), 3.82 (m, 2H), 3.27 (txd, 2H), 3.14 (s, 3H), 1.89 (m, 1H), 1.55 (m, 2H), 1.21 (qxd, 2H).

Preparation 14

1-Isopropyl-3-(tetrahydropyran-4-ylmethyl)-bicyclo[3.2.1]-1β,3,8-triaza-spiro[4.5]dodecan-2,4-dione

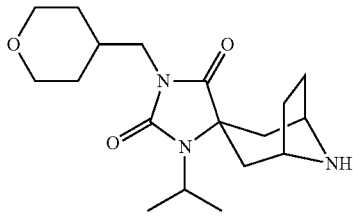

Step 1: To 19.8 g (82 mmol) of 3β-amino-8-benzyl-8-aza-bicyclo[3.2.1]octane-3-carbonitrile (see Preparation 16 step 1) previously dissolved in 68 mL of acetic acid (1.2M) was added dropwise a solution of 33.3 g (410 mmol, 5 eq.) of potassium cyanate in 34 mL of water (12M) over 30 minutes. The internal temperature rose to 75° C. Acetic acid was removed under reduced pressure. The resulting residue was neutralized with NaOH 1N-3N and extracted with DCM, dried over sodium sulfate, filtered and concentrated. The residue was triturated with acetone to remove traces of starting material to yield a mixture (15.8 g) of (8-benzyl-3-cyano-8-aza-bicyclo[3.2.1]oct-3β-yl)-urea and 8-benzyl-4-imino-bicyclo[3.2.1]-1β,3,8-triaza-spiro[4.5]dodecan-2-one.

Step 2: To 15.8 g (56 mmol) of the previous mixture was added 140 mL of HCl 6N. The reaction mixture was heated for 2 hours at 110° C. and the solvent was removed in vacuo. The residue was neutralized with saturated solution of sodium bicarbonate and extracted with ethyl acetate (3×), dried over sodium sulfate, filtered and evaporated in vacuo. The residue was triturated with cold ethyl acetate to yield 13 g (11.8 g (1$^{st}$ trituration)+1.2 g (2$^{nd}$ trituration)) of 8-benzyl-bicyclo[3.2.1]-1β,3,8-triaza-spiro[4.5]dodecan-2,4-dione as a white solid.

Step 3: To 2.2 g (7.72 mmol) of 8-benzyl-bicyclo[3.2.1]-1β,3,8-triaza-spiro[4.5]dodecan-2,4-dione previously dissolved in 19 mL of anhydrous DMF was added 1.5 g (7.72 mmol, 1 eq.) of methanesulfonic acid tetrahydropyran-4-ylmethyl ester and 2.77 g (8.5 mmol, 1.1 eq.) of cesium carbonate. The reaction mixture was stirred for 15 hours at 60° C. While stirring, 38 mL of water were slowly added to obtain a white precipitate. The white precipitate was filtered off, washed back with water (3×20 mL), hexanes (2×20 mL) and dried in vacuo to yield 2.66 g (89.8%) of 8-benzyl-3-(tetrahydropyran-4-ylmethyl)-bicyclo[3.2.1]-1β,3,8-triaza-spiro[4.5]dodecan-2,4-dione.

1H NMR (400 MHz, DMSO-d$_6$): δ [ppm] 8.09 (s, 1H), 7.36-7.27 (m, 4H), 7.20 (m, 1H), 3.77 (br dxd, 2H), 3.52 (s, 2H), 3.21-3.14 (m, 6H), 1.98-1.89 (m, 6H), 1.79 (m, 1H), 1.70 (dxd, 2H), 1.38 (m, 2H), 1.10 (qxd, 2H).

Step 4: To a solution of 10 g (0.026 mol) of 8-benzyl-3-(tetrahydropyran-4-ylmethyl)-bicyclo[3.2.1]-1β,3,8-triaza-spiro[4.5]dodecan-2,4-dione in 200 mL of anhydrous DMF was added 3.13 g (0.078 mol) of sodium hydride in 5 portions over 5-10 minutes at room temperature. After hydrogen evolution had slowed down or stopped, 10.4 mL (0.104 mol) of isopropyl iodide was added and the reaction mixture was stirred for 24 hours at room temperature. The reaction sequence was repeated with additional 1.04 g of sodium hydride and 3.5 mL of isopropyl iodide. After an overnight stirring at room temperature, 70 mL of water was slowly added until appearance of solid. The suspension was cooled down to 0° C. and stirred for an additional hour, filtered then washed with 200 mL of cold water and 200 mL of hexanes. The precipitate was dried in the vacuum oven to yield 8.29 g (75%) of 8-benzyl-1-isopropyl-3-(tetrahydropyran-4-ylmethyl)-bicyclo[3.2.1]-1β,3,8-triaza-spiro[4.5]dodecan-2,4-dione as a pale beige powder.

Step 5: A mixture of 200 mg (0.47 mmol) of 8-benzyl-1-isopropyl-3-(tetrahydropyran-4-ylmethyl)-bicyclo[3.2.1]-1β,3,8-triaza-spiro[4.5]dodecan-2,4-dione, 88 mg (1.4 mmol) of ammonium formate and 40 mg of palladium hydroxide in 3.1 mL of ethanol was charged in a 5 mL microwave tube. The tube was sealed, subjected to microwaves for 3 minutes at 120° C. and cooled to room temperature. The reaction mixture was filtered through celite, rinsed with ethanol and concentrated in vacuo to yield 177 mg (100%) of 1-isopropyl-3-(tetrahydropyran-4-ylmethyl)-bicyclo[3.2.1]-1β,3,8-triaza-spiro[4.5]dodecan-2,4-dione as a yellow oil.

1H NMR (400 MHz, DMSO-d$_6$): δ [ppm] 3.77 (br d×d, 2H), 3.59 (sept., 1H), 3.43 (m, 2H), 3.22-3.12 (m, 5H), 2.03 (q, 2H), 1.86-1.76 (m, 3H), 1.62 (d, 2H), 1.58 (m, 2H), 1.37 (br d, 2H), 1.29 (d, 6H), 1.10 (q×d, 2H).

Preparation 15

1-Isopropyl-3-(tetrahydrofuran-3-yl)-bicyclo[3.2.1]-1β,3,8-triaza-spiro[4.5]dodecan-2,4-dione

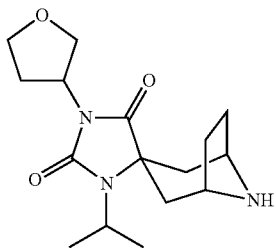

The compound was obtained using essentially the same procedure described in Preparation 14 (Steps 3, 4, and 5) except that methanesulfonic acid tetrahydro-furan-3-yl ester was used for Step 3.

1H NMR (400 MHz, CDCl$_3$): δ [ppm] 5.61 (br s, 1H), 4.59 (m, 1H), 4.08 (q, 1H), 3.90 (t, 1H), 3.83 (m, 1H), 3.76 (m, 4H), 2.39 (m, 2H), 2.06-2.25 (m, 4H), 1.77-1.90 (m, 4H), 1.37 (d, 6H).

Preparation 16

3-(1-Isopropyl-bicyclo[3.2.1]-1β,3,8-triaza-spiro[4.5]dodecan-2,4-dione)pyrrolidine-1-carboxylic acid tert-butyl ester

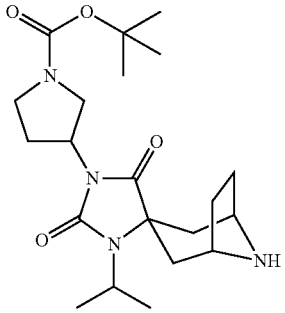

The compound was obtained using essentially the same procedure described in Preparation 14 (Steps 3, 4, and 5) except that 3-methanesulfonyloxy-pyrrolidine-1-carboxylic acid tert-butyl ester was used for Step 3.

1H NMR (400 MHz, DMSO-d$_6$): δ [ppm] 4.47 (quint., 1H), 4.06 (q, 2H), 3.57 (sept., 1H), 3.42 (m, 4H), 2.24 (m, 2H), 2.02 (1.56 (m, 9H), 1.36 (s, 9H), 1.30 (d×d, 6H).

Preparation 17

3-[1,3]Dioxan-5-yl-1-isopropyl-bicyclo[3.2.1]-1β,3,8-triaza-spiro[4.5]dodecan-2,4-dione

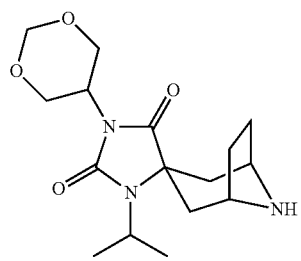

The compound was obtained using essentially the same procedure described in Preparation 14 (Steps 3, 4, and 5) except that methanesulfonic acid [1,3]dioxan-5-yl ester was used for Step 3.

1H NMR (400 MHz, CDCl$_3$): δ [ppm] 4.99 (d, 1H), 4.64 (d, 1H), 4.39-4.32 (m, 1H), 4.26 (m, 2H), 4.14-4.11 (m, 3H), 3.97 (d×d, 2H), 2.58-2.53 (m, 2H), 2.50-2.45 (br d, 2H), 2.21 (m, 2H), 1.96 (m, 2H), 1.42 (d, 6H).

Preparation 18

1-Isopropyl-3-(2-methoxyethyl)-bicyclo[3.2.1]-1β,3,8-triaza-spiro[4.5]dodecan-2,4-dione

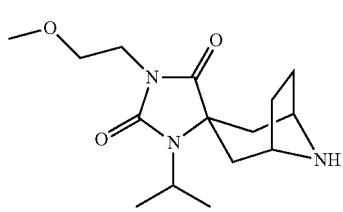

The compound was obtained using essentially the same procedure described in Preparation 14 (Steps 3, 4, and 5) except that 1-bromo-2-methoxy-ethane was used for Step 3.

1H NMR (400 MHz, DMSO-d$_6$): δ [ppm] 3.58 (sept., 1R), 3.47-3.38 (m, 6H), 3.18 (s, 3H), 2.04 (q, 2H), 1.80 (d×d, 2H), 1.61 (d, 2H), 1.57 (m, 2H), 1.29 (d, 6H).

Preparation 19

1-Isopropyl-3-(2-methoxy-2-methylpropyl)-bicyclo[3.2.1]-1β,3,8-triaza-spiro[4.5]dodecan-2,4-dione

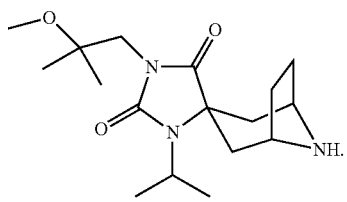

The compound was obtained using essentially the same procedure described in Preparation 14 (Steps 3, 4, and 5) except that 1-iodo-2-methoxy-2-methyl-propane was used for Step 3.

1H NMR (400 MHz, CDCl$_3$): δ [ppm] 3.66 (br s, 2H), 3.54 (quint., 1H), 3.47 (s, 2H), 3.27 (s, 3H), 2.36 (dxd, 2H), 2.05 (dxd, 2H), 1.84 (d, 2H), 1.76 (m, 2H), 1.45 (d, 6H), 1.17 (s, 6H).

Preparation 20

1-Isopropyl-3-(3-methoxypropyl)-bicyclo[3.2.1]-1β,3,8-triaza-spiro[4.5]dodecan-2,4-dione

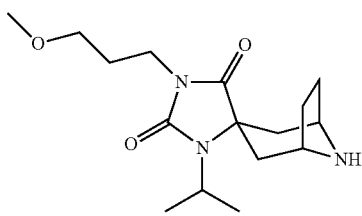

The compound was obtained using essentially the same procedure described in Preparation 14 (Steps 3, 4, and 5) except that 1-bromo-3-methoxy-propane was used for Step 3.

1H NMR (400 MHz, DMSO-d$_6$): δ [ppm] 3.58 (sept., 1H), 3.44 (br s, 2H), 3.31 (t, 2H), 3.24 (t, 2H), 3.13 (s, 3H), 2.04 (q, 2H), 1.80 (dxd, 2H), 1.68-1.56 (m, 6H), 1.29 (d, 6H).

Preparation 21

3-(2-Isopropoxyethyl)-1-isopropyl-bicyclo[3.2.1]-1β,3,8-triaza-spiro[4.5]dodecan-2,4-dione

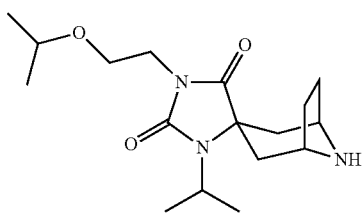

The compound was obtained using essentially the same procedure described in Preparation 14 (Steps 3, 4, and 5) except that methanesulfonic acid 2-isopropoxy-ethyl ester was used for Step 3.

1H NMR (400 MHz, CDCl$_3$): δ [ppm] 3.72 (br s, 2H), 3.68-3.54 (m, 6H), 2.40 (dxd, 2H), 2.09 (dxd, 2H), 1.84 (d, 2H), 1.82 (m, 2H), 1.44 (d, 6H), 1.11 (d, 6H).

Preparation 22

1-Isopropyl-3-(tetrahydrofuran-3-ylmethyl)-bicyclo[3.2.1]-1β,3,8-triaza-spiro[4.5]dodecan-2,4-dione

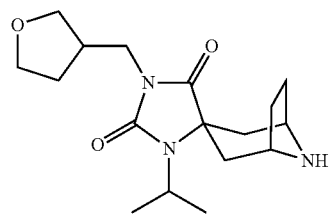

The compound was obtained using essentially the same procedure described in Preparation 14 (Steps 3, 4, and 5) except that methanesulfonic acid tetrahydro-furan-3-ylmethyl ester was used for Step 3.

1H NMR (400 MHz, DMSO-d$_6$): δ [ppm] 4.32 (br s, 1H), 3.70-3.52 (m, 3H), 3.44 (br s, 2H), 3.37-3.25 (m, 5H), 2.04 (q, 2H), 1.87-1.78 (m, 3H), 1.63 (d, 2H), 1.58 (m, 2H), 1.49 (m, 1H), 1.29 (d, 6H).

Preparation 23

1-Isopropyl-3-(tetrahydrofuran-2-ylmethyl)-bicyclo[3.2.1]-1β,3,8-triaza-spiro[4.5]dodecan-2,4-dione

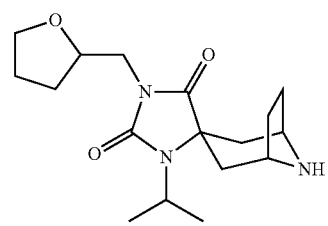

The compound was obtained using essentially the same procedure described in Preparation 14 (Steps 3, 4, and 5) except that methanesulfonic acid tetrahydro-furan-2-ylmethyl ester was used for Step 3.

1H NMR (400 MHz, CDCl$_3$): δ [ppm] 4.23-4.17 (m, 1H), 3.91-3.85 (m, 1H), 3.77-3.72 (m, 1H), 3.65 (br s, 2H), 3.56-3.49 (m, 1H), 3.55 (dxd, 1H), 3.38 (dxd, 1H), 2.36 (dxd, 2H), 2.03 (dxd, 2H), 2.03-1.80 (m, 5H), 1.77-1.73 (m, 2H), 1.65-1.57 (m, 1H), 1.44 (d, 6H).

Preparation 24

3-[1,3]Dioxolan-4-ylmethyl-1-isopropyl-bicyclo
[3.2.1]-1β,3,8-triaza-spiro[4.5]dodecan-2,4-dione

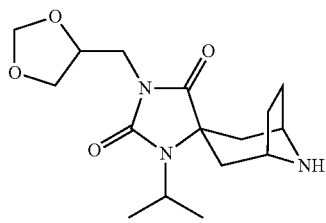

The compound was obtained using essentially the same procedure described in Preparation 14 (Steps 3, 4, and 5) except that methanesulfonic acid [1,3]dioxolan-4-ylmethyl ester was used for Step 3.

1H NMR (400 MHz, CDCl₃): δ [ppm] 5.03 (s, 1H), 4.86 (s, 1H), 4.35-4.32 (m, 1H), 3.90 (m, 1H), 3.79-3.65 (m, 5H), 3.51-3.46 (d×d, 1H), 2.42 (d, 2H), 2.20-2.15 (d×d, 2H), 1.95-1.85 (m, 4H), 1.44 (d, 6H).

Preparation 25

3-Furan-2-ylmethyl-1-isopropyl-bicyclo[3.2.1]-1β,3,8-triaza-spiro[4.5]dodecan-2,4-dione

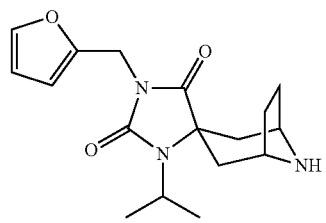

Step 1: N-Ethoxycarbonyltropinone (24.53 g, 124.3 mmol) was dissolved in 124 mL of methanol. Ammonium acetate (76.7 g, 8 eq.) was then added followed by sodium cyanide (7 g, 1.15 eq.). The reaction mixture was stirred overnight at room temperature. The solvent was then evaporated and 100 mL of water was added to the residue. The aqueous phase was extracted with DCM (3×200 mL). The resulting combined organic extracts were washed with 50 mL of water, dried over sodium sulfate and evaporated to yield 28.01 g of 3β-amino-3-cyano-8-aza-bicyclo[3.2.1]octane-8-carboxylic acid ethyl ester.

Step 2: To 4.99 g (22.39 mmol) of 3β-amino-3-cyano-8-aza-bicyclo[3.2.1]octane-8-carboxylic acid ethyl ester dissolved in 20 mL of acetic acid was added a solution of 9.08 g (111.9 mmol) of potassium cyanate in 10 mL of water. Then the reaction mixture was heated at 50° C. for 20 minutes. After cooling down, 50 mL of water was added and the mixture was extracted with DCM (5×50 mL). The combined organic layers were washed with brine, dried over sodium sulfate, filtered and evaporated to give 3.634 g (76%) of intermediate urea.

Step 3: 25 mL of 4M HCl was added to 3.634 g (16.65 mmol) of previous urea and the mixture was heated at 80° C. for 2 hours. The mixture was then cooled to room temperature and extracted with DCM (3×25 mL). The combined organic layers were washed with 25 mL of saturated NaHCO₃, dried over sodium sulfate, filtered and evaporated to give 3.463 g (95%) of bicyclo[3.2.1]-1β,3,8-triaza-spiro[4.5]dodecan-2,4-dione-8-carboxylic acid ethyl ester.

Step 4: To 2.27 g (8.49 mmol) of bicyclo[3.2.1]-1β,3,8-triaza-spiro[4.5]dodecan-2,4-dione-8-carboxylic acid ethyl ester in 20 mL of anhydrous DMF was added 986 mg (7.13 mmol, 1.4 eq.) of potassium carbonate and 1.64 g (10.19 mmol, 1.2 eq.) of 2-bromomethyl-furan. The reaction mixture was stirred for 18 hours at room temperature, diluted with water and extracted with diethyl ether (3×). The combined organic layers were washed back with water, brine and dried over sodium sulfate. The crude was purified by flash chromatography on silica gel (ethyl acetate:hexanes 0 to 100%) to yield 674 mg (23%) of 3-furan-2-ylmethyl-bicyclo[3.2.1]-1β,3,8-triaza-spiro[4.5]dodecan-2,4-dione-8-carboxylic acid ethyl ester.

Step 5: To 674 mg (1.94 mmol) of 3-furan-2-ylmethyl-bicyclo[3.2.1]-1β,3,8-triaza-spiro[4.5]dodecan-2,4-dione-8-carboxylic acid ethyl ester in 19 mL of anhydrous DMF was added 233 mg (5.82 mmol) of sodium hydride (60% dispersion in mineral oil). The reaction mixture was stirred at room temperature for 20 minutes and 780 μL (7.76 mmol) of 2-iodopropane was added in one portion. The mixture was then stirred for 18 hours at 60° C., 35 quenched with water and extracted with diethyl ether (2×). The combined organic layers were washed with water, brine and dried over sodium sulfate to yield 561 mg (74%) of 3-furan-2-ylmethyl-1-isopropyl-bicyclo[3.2.1]-1β,3,8-triaza-spiro[4.5]dodecan-2,4-dione-8-carboxylic acid ethyl ester.

Step 6: To a mixture of 243 mg (0.62 mmol) of 3-furan-2-ylmethyl-1-isopropyl-bicyclo[3.2.1]-1β,3,8-triaza-spiro[4.5]dodecan-2,4-dione-8-carboxylic acid ethyl ester in 10 mL of anhydrous toluene was added 510 μL (3.74 mmol) of iodotrimethylsilane. The reaction mixture was refluxed for 2.5 hours under nitrogen atmosphere and concentrated in vacuo. The residue was triturated with methanol and concentrated. Then the residue was dissolved in DCM and washed with NaOH 1N, water and dried over sodium sulfate to yield 184 mg (930) of 3-furan-2-ylmethyl-1-isopropyl-bicyclo[3.2.1]-1β,3,8-triaza-spiro[4.5]dodecan-2,4-dione.

1H NMR (400 MHz, CDCl₃): δ [ppm] 7.33 (d×d, 1H), 6.29-6.26 (m, 2H), 4.58 (s, 2H), 3.67 (br s, 2H), 3.58-3.55 (m, 1H), 2.39-2.33 (m, 2H), 2.04 (d×d, 2H), 1.81 (br d, 2H), 1.77-1.45 (m, 2H), 1.42 (d, 6H).

Preparation 26

1-Isopropyl-3-thiophen-2-ylmethyl-bicyclo[3.2.1]-1β,3,8-triaza-spiro[4.5]dodecan-2,4-dione

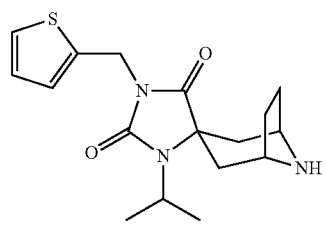

The compound was obtained using essentially the same procedure described in Preparation 25 (Steps 4, 5, and 6) except that 2-bromomethyl-thiophene was used for Step 4.

1H NMR (400 MHz, CDCl₃): δ [ppm] 7.20 (dxd, 1H), 7.05 (m, 1H), 6.93 (dxd, 1H), 4.75 (d, 2H), 3.63 (br s, 2H), 3.55-3.48 (m, 1H), 2.37-2.32 (m, 2H), 2.02-1.97 (dxd, 2H), 1.81-1.72 (m, 5H), 1.43 (d, 6H).

Preparation 27

1-Isopropyl-3-thiazol-2-ylmethyl-bicyclo[3.2.1]-1β,3,8-triaza-spiro[4.5]dodecan-2,4-dione

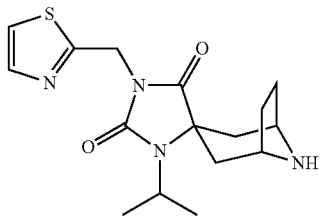

The compound was obtained using essentially the same procedure described in Preparation 25 (Steps 4, 5, and 6) except that methanesulfonic acid thiazol-2-ylmethyl ester was used for Step 4.

1H NMR (400 MHz, CDCl₃): δ [ppm] 7.59 (d, 1H), 7.14 (d, 1H), 4.82 (s, 2H), 3.59-3.56 (m, 2H), 3.52-3.47 (m, 1H), 2.26-2.21 (m, 2H), 1.97 (dxd, 2H), 1.78 (dxd, 2H), 1.67-1.62 (m, 2H), 1.33 (d, 6H).

Scheme 7

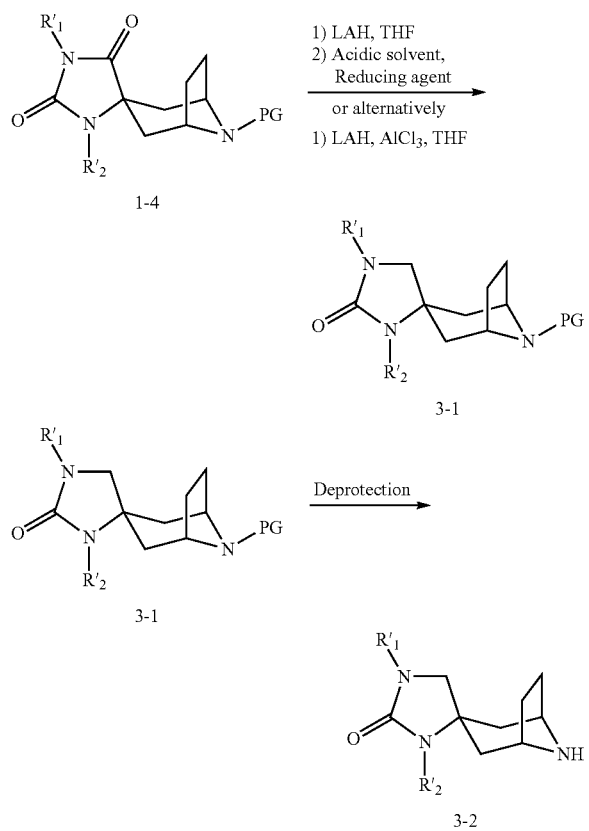

General procedure: N1 and N3 bisalkylated hydantoin 1-4 is sequentially reduced by treatment with LAH followed by a reducing agent such as sodium hydride or sodium triacetoxy-borohydride in acidic solvent such as formic acid or acetic acid, or alternatively in one step by treatment with LAH/ AlCl₃. Then the resulting N1 and N3 bisalkylated urea 3-1 is finally deprotected using standards procedures of hydrogenolysis or acidic treatment depending on the nature of the protecting group (PG).

Preparation 28

Methanesulfonic acid(R)-(tetrahydrofuran-3-yl)ester

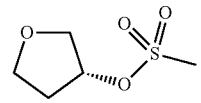

A solution of 4.86 g (55.18 mmol) of (R)-(−)-3-hydroxytetrahydrofuran in 55 mL of anhydrous DCM (1M) was cooled to 0° C. with an ice bath. Then 8.5 mL (60.7 mmol, 1.1 eq.) of triethylamine and 4.8 mL (60.7 mmol, 1.1 eq.) of methanesulfonyl chloride were added successively. The reaction mixture was stirred for 2 hours at 0° C. and quenched with a saturated solution of sodium bicarbonate (70 mL). The aqueous layer was extracted with DCM (50 mL). Then the organic layers were washed with water (2×50 mL), brine (50 mL) and dried over sodium sulfate. After filtration and concentration in vacuo, a yellowish oil (7.93 g, 86.4%) was obtained corresponding to the methanesulfonic acid(R)-(tetrahydrofuran-3-yl)ester.

1H NMR (400 MHz, DMSO-d₆): δ [ppm] 5.26 (m, 1H), 3.84-3.67 (m, 4H), 3.18 (s, 3H), 2.22-2.13 (m, 1H), 2.08-2.01 (m, 1H).

Preparation 29

(S)-1-isopropyl-3-(tetrahydrofuran-3-yl)-bicyclo[3.2.1]-1β,3,8-triaza-spiro[4.5]dodecan-2-one

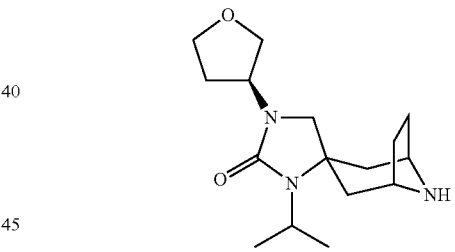

Step 1: To 4.75 g (16.67 mmol) of 8-benzyl-bicyclo[3.2.1]-1β,3,8-triaza-spiro[4.5]dodecan-2,4-dione dissolved in 40 mL of anhydrous DMF (0.4M) was added 153 mg (18.33 mmol, 1.1 eq.) of lithium hydride. The reaction mixture was stirred for 1 hour at room temperature before adding 3.32 g (20 mmol, 1.2 eq.) of methanesulfonic acid(R)-(tetrahydrofuran-3-yl)ester dissolved in 2 mL of anhydrous DMF. The reaction mixture was stirred for 2 hours at 100° C. and 80 mL of ice water was added slowly while stirring at room temperature. The white precipitate was filtered off, washed back with cold water (5×50 mL), hexanes (2×20 mL) and dried in vacuo to yield 4.74 g (80%) of (S)-8-benzyl-3-(tetrahydrofuran-3-yl)-bicyclo[3.2.1]-1β,3,8-triaza-spiro[4.5]dodecan-2,4-dione as a white solid.

1H NMR (400 MHz, DMSO-d₆): δ [ppm] 8.16 (s, 1H), 7.36 (m, 2H), 7.28 (m, 2H), 7.20 (m, 1H), 4.47 (m, 1H), 3.88 (q, 1H), 3.79 (t, 1H), 3.73 (txd, 1H), 3.60 (dxd, 1H), 3.52 (s, 2H), 3.12 (hr s, 2H), 2.12-1.89 (m, 8H), 1.72 (d, 2H).

Step 2: To 2.28 g (6.43 mmol) of (S)-8-benzyl-3-(tetrahydrofuran-3-yl)-bicyclo[3.2.1]-1β,3,8-triaza-spiro[4.5]dodecan-2,4-dione in 65 mL of anhydrous DMF was added 772 mg (19.3 mmol, 3 eq.) of sodium hydride (60% dispersion in oil). The reaction mixture was stirred for 20 minutes at room temperature and 2.57 mL (25.74 mmol, 4 eq.) of 2-iodopropane was added in one portion. The mixture was agitated for 16 hours at 60° C., quenched with water (75 mL) and extracted with diethyl ether (2×100 mL). The organic layers were dried over magnesium sulfate and the crude was purified by flash chromatography on silica gel (ethyl acetate:hexane 0 to 100%) to yield 1.82 g (71%) of (S)-8-benzyl-1-isopropyl-3-(tetrahydrofuran-3-yl)-bicyclo[3.2.1]-1β,3,8-triaza-spiro[4.5]dodecan-2,4-dione as a white solid.

1H NMR (400 MHz, DMSO-$d_6$): δ [ppm] 7.35-7.28 (m, 4H), 7.22-7.18 (m, 1H), 4.48 (m, 1H), 3.89 (q, 1H), 3.80 (t, 1H), 3.76-3.71 (m, 1H), 3.62-3.52 (m, 2H), 3.46 (s, 2H), 3.16 (br s, 2H), 2.11-1.89 (m, 8H), 1.75 (d, 2H), 1.35 (d, 6H).

Step 3: To a 0° C. mixture of (S)-8-benzyl-1-isopropyl-3-(tetrahydrofuran-3-yl)-bicyclo[3.2.1]-1β,3,8-triaza-spiro[4.5]dodecan-2,4-dione (1.80 g, 4.53 mmol) in 50 mL of anhydrous THF was added 4.58 mL (4.58 mmol) of lithium aluminium hydride (1M solution in THF). The mixture was stirred at 0° C. for 1.5 hour and then quenched with 13 mL of saturated Rochelle salt solution and 2 mL of water, stirred for 15 minutes at room temperature and extracted with DCM (3×100 mL). The combined organic layers were washed with brine, dried over sodium sulfate and concentrated in vacuo.

Step 4: The crude (1.65 g) was then taken in formic acid (15 mL) at 0° C. and 628 mg (16.61 mmol, 4 eq.) of sodium borohydride was added portion wise (caution: serious gas evolution). The mixture was stirred at room temperature for 1 hour, diluted with DCM and neutralized with NaOH 4N (95 mL). The organic layer was washed with brine and dried over sodium sulfate to yield 1.47 g (93% over 2 steps) of (S)-8-benzyl-1-isopropyl-3-(tetrahydrofuran-3-yl)-bicyclo[3.2.1]-1β,3,8-triaza-spiro[4.5]dodecan-2-one as a white foam.

1H NMR (400 MHz, DMSO-$d_6$): δ [ppm] 7.34-7.27 (m, 4H), 7.22-7.18 (m, 1H), 4.28 (m, 1H), 3.79 (m, 1H), 3.58-3.53 (m, 3H), 3.46 (s, 2H), 3.30 (q, 2H), 3.20 (sept., 1H), 3.13 (br s, 2H), 1.98-1.77 (m, 6H), 1.68 (d, 2H), 1.57 (d×d, 2H), 1.24 (d×d, 6H).

Step 5: To 1.43 g (3.75 mmol) of (S)-8-benzyl-1-isopropyl-3-(tetrahydrofuran-3-yl)-bicyclo[3.2.1]-1β,3,8-triaza-spiro[4.5]dodecan-2-one was added 53 mg of palladium hydroxide, 710 mg (11.25 mmol, 3 eq.) of ammonium formate and 30 ml of ethanol. The reaction mixture was stirred at 80° C. for 3.5 hours, cooled to room temperature and filtered through a pad of celite. After concentration in vacuo, 1.11 g (100%) of (S)-1-isopropyl-3-(tetrahydrofuran-3-yl)-bicyclo[3.2.1]-1β,3,8-triaza-spiro[4.5]dodecan-2-one was obtained as a white solid.

1H NMR (400 MHz, DMSO-$d_6$): δ [ppm] 4.27 (m, 15), 3.79 (m, 1H), 3.58-3.52 (m, 3H), 3.41 (br s, 2H), 3.32-3.23 (m, 3H), 2.97 (br s, 1H), 1.95 (m, 1H), 1.80-1.52 (m, 9H), 1.19 (d×d, 6H).

Preparation 30

1-Isopropyl-3-(tetrahydropyran-4-ylmethyl)-bicyclo[3.2.1]-1β,3,8-triaza-spiro[4.5]dodecan-2-one

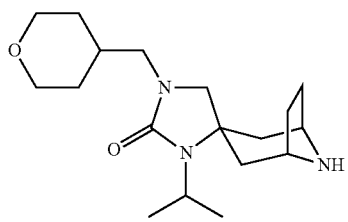

Step 1: AlCl$_3$ (237 mg, 1.777 mmol) was dissolved in 1.5 mL, of anhydrous THF and the solution was cooled in an ice bath before adding dropwise 1.34 mL of LAH (1M in THF) (caution: the reaction was very exothermic). The solution was then stirred for 90 minutes and 191.2 mg (0.445 mmol) of 8-benzyl-1-isopropyl-3-(tetrahydropyran-4-ylmethyl)-bicyclo[3.2.1]-1β,3,8-triaza-spiro[4.5]dodecan-2,4-dione (from Preparation 14) dissolved in 2 mL of anhydrous THF was then added dropwise. The resulting solution was stirred at 0° C. for an additional 60 minutes. The reaction mixture was then quenched with 2 mL of saturated Rochelle's salt and 5 mL of water. The resulting mixture was extracted with ethyl acetate (3×10 mL), the combined organic extracts were washed with brine, dried over Na$_2$SO$_4$, filtered and evaporated to give 133.7 mg (73%) of 8-benzyl-1-isopropyl-3-(tetrahydropyran-4-ylmethyl)-bicyclo[3.2.1]-1β,3,8-triaza-spiro[4.5]dodecan-2-one.

Step 2: 483 mg (1.173 mmol) of 8-benzyl-1-isopropyl-3-(tetrahydropyran-4-ylmethyl)-bicyclo[3.2.1]-1β,3,8-triaza-spiro[4.5]dodecan-2-one was dissolved in 7.5 mL of ethanol followed by palladium on charcoal (10% w/w dry basis, wet, 50 mg) and ammonium formate (222 mg, 3.52 mmol). The reaction mixture was then refluxed for two hours, cooled to room temperature, filtered over celite and evaporated to give 368 mg (98%) of 1-isopropyl-3-(tetrahydropyran-4-ylmethyl)-bicyclo[3.2.1]-1β,3,8-triaza-spiro[4.5]dodecan-2-one.

1H NMR (400 MHz, DMSO-$d_6$): δ [ppm] 4.32 (br s, 1H), 3.79 (br d×d, 2H), 3.40 (q, 4H), 3.24 (m, 3H), 2.79 (d, 2H), 1.77 (br d×d, 2H), 1.70 (m, 1H), 1.63 (br s, 4H), 1.52 (d, 2H), 1.43 (d×d, 2H), 1.19 (d, 6H), 1.12-1.02 (q×d, 2H), Preparation 31

(R)-1-isopropyl-3-(tetrahydrofuran-3-yl)-bicyclo[3.2.1]-1β,3,8-triaza-spiro[4.5]dodecan-2-one

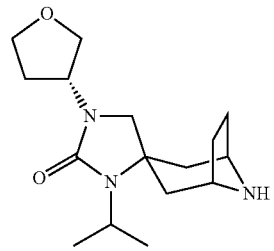

The compound was obtained using essentially the same procedure described in Preparation 29 (Steps 1 to 5) except that methanesulfonic acid(S)-(tetrahydrofuran-3-yl)ester was used for Step 1.

1H NMR (400 MHz, DMSO-$d_6$): δ [ppm] 4.27 (m, 1H), 3.79 (m, 1H), 3.58-3.52 (m, 3H), 3.41 (br s, 2H), 3.32-3.23 (m, 3H), 2.97 (br s, 1H), 1.95 (m, 1H), 1.80-1.52 (m, 9H), 1.19 (d×d, 6H).

Preparation 32

1-Isopropyl-3-(tetrahydrofuran-3-yl)-bicyclo[3.2.1]-
1β,3,8-triaza-spiro[4.5]dodecan-2-one

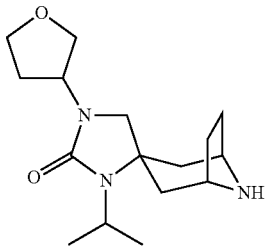

The compound was obtained using essentially the same procedure described in Preparation 29 (Steps 3 to 5) from Preparation 15.

1H NMR (400 MHz, DMSO-d$_6$): δ [ppm] 4.27 (m, 1H), 3.79 (m, 1H), 3.58-3.52 (m, 3H), 3.41 (br s, 2H), 3.32-3.23 (m, 3H), 2.97 (br s, 1H), 1.95 (m, 1H), 1.80-1.52 (m, 9H), 1.19 (d×d, 6H).

Preparation 33

1-Isopropyl-3-(tetrahydropyran-4-yl)-bicyclo[3.2.1]-
1β,3,8-triaza-spiro[4.5]dodecan-2-one

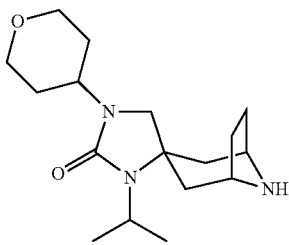

The compound was obtained using essentially the same procedure described in Preparation 29 (Steps 3 to 5) from Preparation 12.

1H NMR (400 MHz, CDCl$_3$): δ [ppm] 5.33 (br s, 1H), 3.92 (m, 2H), 3.84 (m, 1H), 3.77 (br s, 2H), 3.36 (m, 3H), 3.26 (s, 2S), 2.12 (m, 2H), 1.94 (m, 2H), 1.78 (m, 2H), 1.68 (m, 2H), 1.53 (m, 4H), 1.28 (d, 6H).

Preparation 34

1-Isopropyl-3-(tetrahydropyran-3-yl)-bicyclo[3.2.1]-
1β,3,8-triaza-spiro[4.5]dodecan-2-one

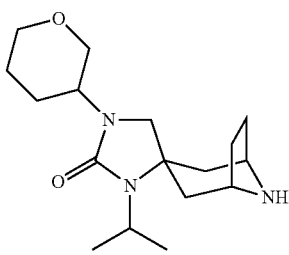

The compound was obtained using essentially the same procedure described in Preparation 29 (Steps 1 to 5) except that methanesulfonic acid tetrahydro-pyran-3-yl ester was used for Step 1.

Preparation 35

1-Isopropyl-3-(4-methoxy-cyclohexyl)-bicyclo
[3.2.1]-1β,3,8-triaza-spiro[4.5]dodecan-2-one

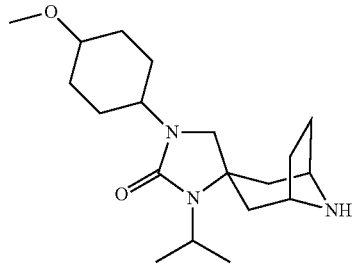

The compound was obtained using essentially the same procedure described in Preparation 29 (Steps 1 to 5) except that methanesulfonic acid 4-methoxy-cyclohexyl ester was used for Step 1.

1H NMR (400 MHz, CDCl$_3$): δ [ppm] 3.89 (br s, 2H), 3.69-3.66 (m, 1H), 3.39 (br s, 1H), 3.50 (m, 1H), 3.35 (d×d, 2H), 3.30 (s, 1.5H), 3.28 (s, 1.5H), 2.28 (d×t, 2H), 2.20-1.70 (m, 10H), 1.59-1.22 (m, 4H), 1.33 (d×d, 6H).

Preparation 36

1-Isopropyl-3-(tetrahydropyran-3-ylmethyl)-bicyclo
[3.2.1]-1β,3,8-triaza-spiro[4.5]dodecan-2-one

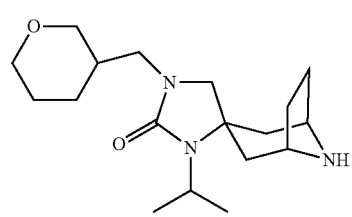

The compound was obtained using essentially the same procedure described in Preparation 29 (Steps 1 to 5) except that methanesulfonic acid tetrahydropyran-3-ylmethyl ester was used for Step 1.

1H NMR (400 MHz, DMSO-d$_6$): δ [ppm] 3.65 (m, 2H), 3.50 (br s, 2H), 3.33-3.22 (m, 6H), 3.00 (d×d, 1H), 2.79 (q×d, 2H), 1.85 (br d, 2H), 1.73-1.39 (m, 8H), 1.19 (d, 6H), 1.12 (m, 2H).

Preparation 37

1-Isopropyl-3-(tetrahydropyran-2-ylmethyl)-bicyclo[3.2.1]-1β,3,8-triaza-spiro[4.5]dodecan-2-one

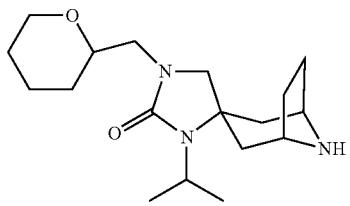

The compound was obtained using essentially the same procedure described in Preparation 29 (Steps 1 to 5) except that methanesulfonic acid tetrahydropyran-2-ylmethyl ester was used for Step 1.

1H NMR (400 MHz, CDCl$_3$): δ [ppm] 3.96 (d×m, 1H), 3.70 (br s, 2H), 3.63 (d, 1H), 3.47-3.37 (m, 3H), 3.42 (d, 1H), 3.35-3.29 (m, 2H), 2.90 (d×d, 1H), 2.03 (t×d, 2H), 1.88-1.80 (m, 5H), 1.74 (br t, 2H), 1.60-1.43 (m, 4H), 1.35 (t, 6H), 1.32-1.22 (m, 1H).

Preparation 38

1-Isopropyl-3-(5-methyl-[1,3]dioxan-5-ylmethyl)-bicyclo[3.2.1]-1β,3,8-triaza-spiro[4.5]dodecan-2-one

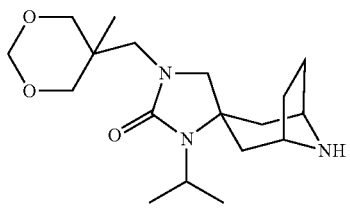

The compound was obtained using essentially the same procedure described in Preparation 29 (Steps 1 to 5) except that methanesulfonic acid 5-methyl-[1,3]dioxan-5-ylmethyl ester was used for Step 1.

1H NMR (400 MHz, CDCl$_3$): δ [ppm] 4.94 (d, 1H), 4.64 (d, 1H), 4.36 (br s, 2H), 3.72-3.66 (m, 3H), 3.50 (s, 2H), 3.39 (d, 2H), 3.19 (s, 2H), 2.59 (d×d, 2H), 2.31 (m, 2H), 1.98 (q, 2H), 1.87 (d, 2H), 1.35 (d, 6H), 0.80 (s, 3H).

Preparation 39

1-Isopropyl-3-(tetrahydrofuran-3-ylmethyl)-bicyclo[3.2.1]-1β,3,8-triaza-spiro[4.5]dodecan-2-one

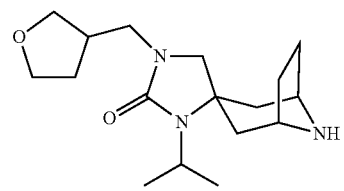

The compound was obtained using essentially the same procedure described in Preparation 29 (Steps 3 to 5) from Preparation 22.

1H NMR (400 MHz, DMSO-d$_6$): δ [ppm] 3.70-3.53 (m, 3H), 3.40 (br s, 2H), 3.34-3.25 (m, 4H), 2.92 (d×d, 2H), 2.38 (quint., 1H), 1.89-1.74 (m, 3H), 1.63 (m, 4H), 1.53-1.41 (m, 3H), 1.19 (d, 6H).

Preparation 40

1-Isopropyl-3-(tetrahydrofuran-2-ylmethyl)-bicyclo[3.2.1]-1β,3,8-triaza-spiro[4.5]dodecan-2-one

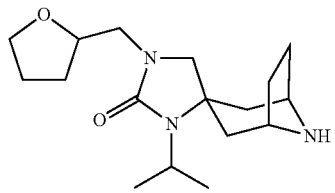

The compound was obtained using essentially the same procedure described in Preparation 29 (Steps 3 to 5) from Preparation 23.

1H NMR (400 MHz, DMSO-d$_6$): δ [ppm] 3.94 (m, 1H), 3.79 (m, 1H), 3.68 (m, 1H), 3.49 (m, 2H), 3.43 (m, 3H), 3.09 (q×d, 2H), 2.27 (br s, 1H), 1.96-1.81 (m, 5H), 1.70-1.50 (m, 7H), 1.29 (d×d, 6H).

Preparation 41

(R)-1-Isopropyl-3-(tetrahydrofuran-2-ylmethyl)-bicyclo[3.2.1]-1β,3,8-triaza-spiro[4.5]dodecan-2-one

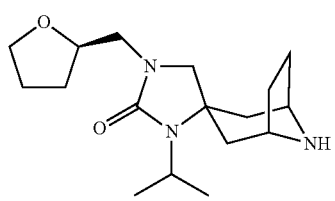

The compound was obtained using essentially the same procedure described in Preparation 29 (Steps 1 to 5) except that methanesulfonic acid (R)-tetrahydro-furan-2-ylmethyl ester was used for Step 1.

1H NMR (400 MHz, DMSO-d$_6$): δ [ppm] 3.94 (m, 1H), 3.79 (m, 1H), 3.68 (m, 1H), 3.49 (m, 2H), 3.43 (m, 3H), 3.09 (q×d, 2H), 2.27 (br s, 1H), 1.96-1.81 (m, 5H), 1.70-1.50 (m, 7H), 1.29 (d×d, 6H).

Preparation 42

(S)-1-Isopropyl-3-(tetrahydrofuran-2-ylmethyl)-bi-cyclo[3.2.1]-1β,3,8-triaza-spiro[4.5]dodecan-2-one

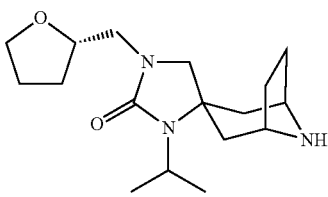

The compound was obtained using essentially the same procedure described in Preparation 29 (Steps 1 to 5) except that methanesulfonic acid(S)-tetrahydro-furan-2-ylmethyl ester was used for Step 1.

1H NMR (400 MHz, DMSO-$d_6$): δ [ppm] 3.94 (m, 1H), 3.79 (m, 1H), 3.68 (m, 1H), 3.49 (m, 2H), 3.43 (m, 3H), 3.09 (q×d, 2H), 2.27 (br s, 1H), 1.96-1.81 (m, 5H), 1.70-1.50 (m, 7H), 1.29 (d×d, 6H).

Preparation 43

1-Isopropyl-3-(3-methyl-oxetan-3-ylmethyl)-bicyclo[3.2.1]-1β,3,8-triaza-spiro[4.5]dodecan-2-one

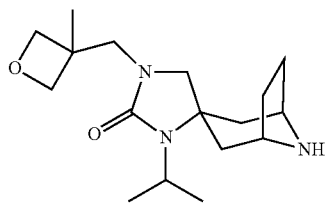

The compound was obtained using essentially the same procedure described in Preparation 29 (Steps 1 to 5) except that methanesulfonic acid 3-methyl-oxetan-3-ylmethyl ester was used for Step 1.

1H NMR (400 MHz, CDCl$_3$): δ [ppm] 4.51 (d, 2H), 4.34 (d, 2H), 3.78 (br s, 2H), 3.43-3.37 (m, 1H), 3.39 (s, 2H), 3.21 (s, 2H), 2.16 (d×d, 2H), 1.98-1.95 (m, 2H), 1.78-1.74 (m, 4H), 1.33 (d, 6H), 1.28 (s, 3H).

Preparation 44

1-Isopropyl-3-(2-methoxyethyl)-bicyclo[3.2.1]-1β,3,8-triaza-spiro[4.5]dodecan-2-one

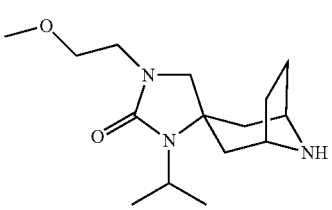

The compound was obtained using essentially the same procedure described in Preparation 29 (Steps 3 to 5) from Preparation 18.

1H NMR (400 MHz, DMSO-$d_5$): δ [ppm] 3.43 (br s, 2H), 3.35-3.27 (m, 6H), 3.21 (s, 3H), 3.09 (t, 2H), 1.78 (d×d, 2H), 1.63 (br s, 4H), 1.54 (br d, 2H), 1.19 (d, 6H).

Preparation 45

1-Isopropyl-3-(2-ethoxyethyl)-bicyclo[3.2.1]-1β,3,8-triaza-spiro[4.5]dodecan-2-one

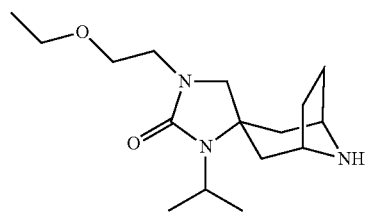

The compound was obtained using essentially the same procedure described in Preparation 29 (Steps 1 to 5) except that 2-bromoethyl ethylether was used for Step 1.

1H NMR (400 MHz, DMSO-$d_6$) δ [ppm] 4.30 (br s, 1H), 3.39-3.26 (m, 9H), 3.07 (t, 2H), 1.76 (d×d, 2H), 1.62 (d, 4H), 1.52 (d, 2H), 1.20 (d, 6H), 1.07 (t, 3H).

Preparation 46

1-Isopropyl-3-(2-methoxy-2-methylpropyl)-bicyclo[3.2.1]-1β,3,8-triaza-spiro[4.5]dodecan-2-one

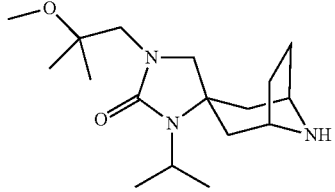

The compound was obtained using essentially the same procedure described in Preparation 29 (Steps 3 to 5) from Preparation 19.

1H NMR (400 MHz, CDCl$_3$): δ [ppm] 4.19 (br s, 2H), 3.72 (quint., 1H), 3.60 (s, 2H), 3.20 (s, 3H), 3.09 (s, 2H), 2.59 (d, 2H), 2.32 (m, 2H), 2.01 (d×d, 2H), 1.90 (d, 2H), 1.38 (d, 6H), 1.15 (s, 6H).

Preparation 47

1-Isopropyl-3-(3-methoxypropyl)-bicyclo[3.2.1]-1β,3,8-triaza-spiro[4.5]dodecan-2-one

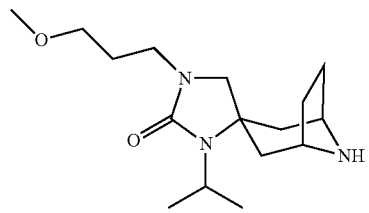

The compound was obtained using essentially the same procedure described in Preparation 29 (Steps 3 to 5) from Preparation 20.

1H NMR (400 MHz, DMSO-d$_6$): δ [ppm] 3.41 (br s, 2H), 3.26 (m, 5H), 3.17 (s, 3H), 2.96 (t, 2H), 1.77 (m, 2H), 1.66-1.51 (m, 8H), 1.19 (d, 6H).

Preparation 48

3-(2-Isopropoxyethyl)-1-isopropyl-bicyclo[3.2.1]-1β,3,8-triaza-spiro[4.5]dodecan-2-one

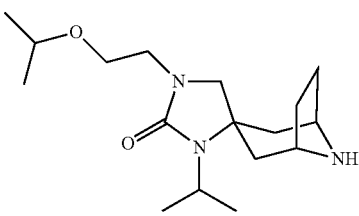

The compound was obtained using essentially the same procedure described in Preparation 29 (Steps 3 to 5) from Preparation 21.

1H NMR (400 MHz, CDCl$_3$): δ [ppm] 3.69 (br s, 2H), 3.58 (sept., 1H), 3.53 (m, 4H), 3.33 (sept., 1H), 3.27 (t, 2H), 2.98 (br s, 1H), 2.03 (d×d, 2H), 1.84 (m, 4H), 1.74 (m, 2H), 1.36 (d, 6H), 1.15 (d, 6H).

Preparation 49

3-Furan-2-ylmethyl-1-isopropyl-bicyclo[3.2.1]-1β,3,8-triaza-spiro[4.5]dodecan-2-one

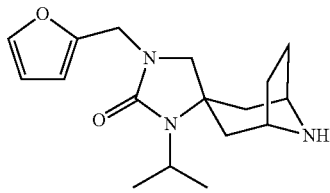

The compound was obtained using essentially the same procedure described in Preparation 29 (Steps 3 to 5) from Preparation 25.

1H NMR (400 MHz, CDCl$_3$): δ [ppm] 7.37 (d×d, 1H), 6.33 (d×d, 1H), 6.21 (d×d, 1H), 4.29 (br s, 2H), 3.63 (br s, 2H), 3.30 (d×d, 3H), 2.29 (m, 1H), 2.01 (d×d, 2H), 1.81-1.67 (m, 6H), 1.37 (d, 6H).

Preparation 50

1-Isopropyl-3-thiophen-2-ylmethyl-bicyclo[3.2.1]-1β,3,8-triaza-spiro[4.5]dodecan-2-one

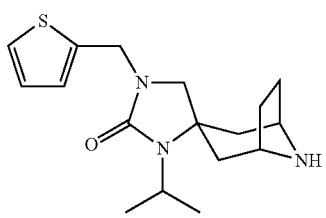

The compound was obtained using essentially the same procedure described in Preparation 29 (Steps 3 to 5) from Preparation 26.

1H NMR (400 MHz, CDCl$_3$): δ [ppm] 7.23 (d×d, 1H), 6.97-6.92 (m, 2H), 4.48 (d, 2H), 3.63 (br s, 2H), 3.35-3.30 (m, 1H), 3.28 (s, 2H), 2.29 (m, 1H), 2.02-1.97 (d×d, 2H), 1.75 (m, 6H), 1.39 (d, 6H).

Preparation 51

1-Isopropyl-3-thiazol-2-ylmethyl-bicyclo[3.2.1]-1β,3,8-triaza-spiro[4.5]dodecan-2-one

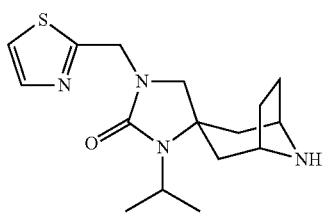

The compound was obtained using essentially the same procedure described in Preparation 29 (Steps 3 to 5) from Preparation 27.

1H NMR (400 MHz, CDCl$_3$): δ [ppm] 7.65 (d, 1H), 7.24 (d, 1H), 4.57 (s, 2H), 3.56 (br s, 2H), 3.33 (s, 2H), 3.26 (m, 1H), 1.93 (d×d, 2H), 1.74-1.63 (m, 7H), 1.32 (d, 6H).

Preparation 52

1-Isopropyl-3-(1-methyl-1H-imidazol-2-ylmethyl)-bicyclo[3.2.1]-1β,3,8-triaza-spiro[4.5]dodecan-2-one

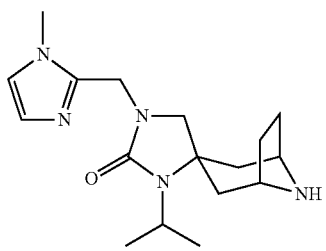

The compound was obtained using essentially the same procedure described in Preparation 29 (Steps 1 to 5) except that methanesulfonic acid 1-methyl-1H-imidazol-2-ylmethyl ester was used for Step 1.

1H NMR (400 MHz, CDCl$_3$): δ [ppm] 6.94 (d, 1H), 6.83 (d, 1H), 4.38 (s, 2H), 4.09 (br s, 2H), 3.76-3.71 (m, 1H), 3.69 (s, 3H), 3.47 (s, 2H), 2.53-2.49 (br dxd, 2H), 2.22-2.19 (m, 2H), 1.99 (m, 2H), 1.80 (br d, 2H), 1.31 (d, 6H).

Preparation 53

1-Isopropyl-3-(4-methoxy-phenyl)-bicyclo[3.2.1]-1β,3,8-triaza-spiro[4.5]dodecan-2-one

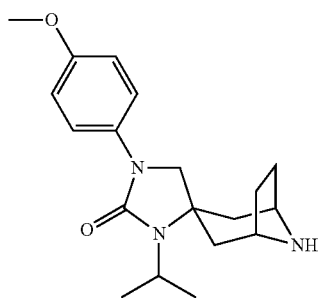

The compound was obtained using essentially the same procedure described in Preparation 29 (Steps 3 to 5) from Preparation 9.

1H NMR (400 MHz, DMSO-d$_6$): δ [ppm] 7.40 (dxd, 2H), 6.82 (dxd, 2H), 3.80 (s, 2H), 3.67 (s, 3H), 3.51 (br s, 2H), 3.44 (sept., 1H), 1.92 (br dxd, 2H), 1.83 (m, 2H), 1.68 (br d, 4H), 1.27 (d, 6H).

Preparation 54

1-Isopropyl-3-(3-methoxy-phenyl)-bicyclo[3.2.1]-1β,3,8-triaza-spiro[4.5]dodecan-2-one

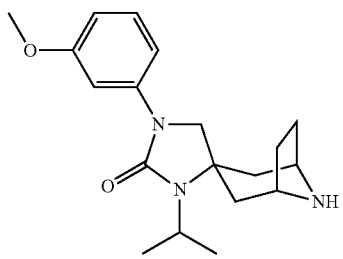

The compound was obtained using essentially the same procedure described in Preparation 29 (Steps 3 to 5) from Preparation 10.

1H NMR (400 MHz, DMSO-d$_6$): δ [ppm] 7.25 (d, 1H), 7.15 (t, 1H), 7.01 (dxd, 1H), 6.52 (dxd, 1H), 3.87 (s, 2H), 3.75 (br s, 2H), 3.69 (s, 3H), 3.54 (sept., 1H), 2.08-1.97 (m, 4H), 1.79 (m, 4H), 1.28 (d, 6H).

Preparation 55

1-Isopropyl-3-(2-methoxy-phenyl)-bicyclo[3.2.1]-1β,3,8-triaza-spiro[4.5]dodecan-2-one

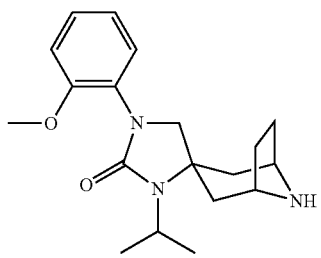

The compound was obtained using essentially the same procedure described in Preparation 29 (Steps 3 to 5) from Preparation 11.

1H NMR (400 MHz, DMSO-d$_6$): δ [ppm] 7.21 (dxd, 1H), 7.15 (txd, 1H), 7.01 (dxd, 1H), 6.87 (txd, 1H), 3.76 (s, 3H), 3.70 (s, 2H), 3.46 (br s, 2H), 3.39 (sept., 1H), 1.87 (dxd, 2H), 1.70 (br d, 2H), 1.63 (br s, 4), 1.26 (d, 6H).

Scheme 8

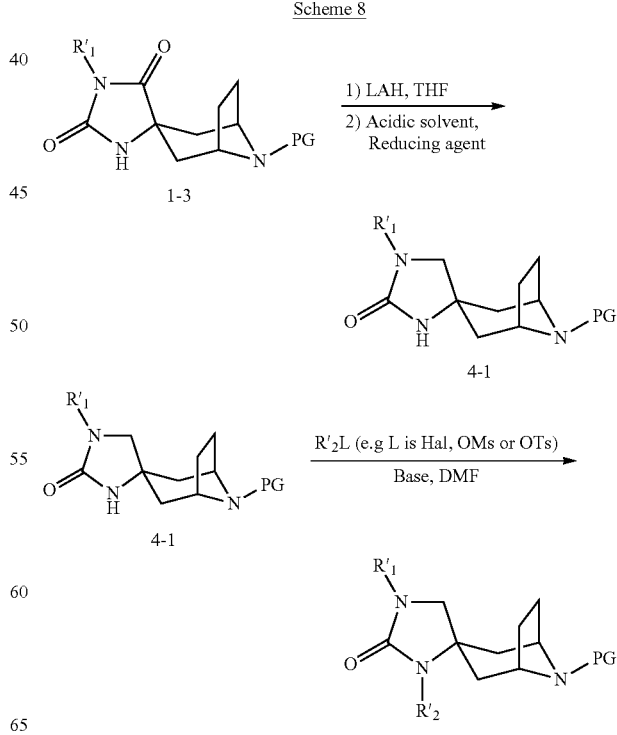

-continued

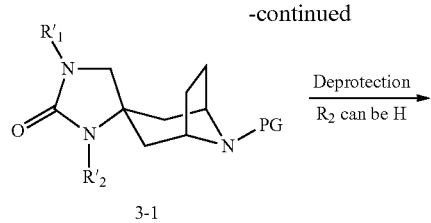

General procedure: N3 alkylated hydantoin 1-3 is sequentially reduced by treatment with LAH followed by a reducing agent such as sodium hydride or sodium triacetoxyborohydride in acidic solvent such as formic acid or acetic acid. Further N1-alkylation takes place by treating the urea 4-1 with a strong base such as KH, NaH or LiH and an electrophile R'$_s$L (L is an appropriate leaving group such as halogen (Hal), OMs or OTs) in aprotic solvent such as DMF, NMP, DMAC or DMSO at temperature between 20 and 100° C. Then the resulting N3 monoalkylated urea 4-1 and the N1 and N3 bisalkylated urea 3-1 are finally deprotected using standards procedures of hydrogenolysis or acidic treatment depending on the nature of the protecting group (PG).

Preparation 56

3-(Tetrahydropyran-4-ylmethyl)-bicyclo[3.2.1]-1β,3,8-triaza-spiro[4.5]dodecan-2-one

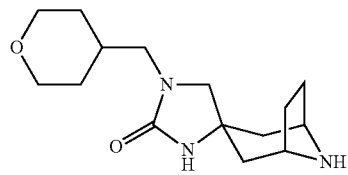

Step 1: To a solution of 8-benzyl-3-(tetrahydropyran-4-ylmethyl)-bicyclo[3.2.1]-1β,3,8-triaza-spiro[4.5]dodecan-2,4-dione (4.02 g, 10.48 mmol) in THF (50 mL) at 0° C. was added lithium aluminium hydride 1M/THF (14 mL, 14 mmol) dropwise. The mixture was warmed to room temperature and stirred overnight. The reaction mixture was quenched with water (0.5 mL) (very vigorous exotherm), aqueous NaOH (4M, 0.5 mL) and then water (1.5 mL). The mixture was filtered and the filter cake thoroughly rinsed with DCM. The mother liquor was evaporated to give 8-benzyl-4-hydroxy-3-(tetrahydropyran-4-ylmethyl)-bicyclo[3.2.1]-1β,3,8-triaza-spiro[4.5]dodecan-2-one as a white solid (3.4 g, 84%).

Step 2: To a solution of 8-benzyl-4-hydroxy-3-(tetrahydropyran-4-ylmethyl)-bicyclo[3.2.1]-1β,3,8-triaza-spiro[4.5]dodecan-2-one (3.4 g, 8.83 mmol) in formic acid (16 mL) at 0° C. was added sodium borohydride (1.33 g, 35.3 mmol) portionwise (vigorous reaction). The reaction was stirred at room temperature for 1.5 hours. The reaction mixture was neutralized with aqueous NaOH (4M, 100 mL) and extracted with DCM. The organic extracts were dried over sodium sulfate and evaporated to give 3-(tetrahydropyran-4-ylmethyl)-bicyclo[3.2.1]-1β,3,8-triaza-spiro[4.5]dodecan-2-one as a white solid (3.12 g, 96%).

1H NMR (400 MHz, CDCl$_3$): δ [ppm] 7.37-7.23 (m, 5H), 4.43 (s, 1H), 3.97-3.93 (m, 2H), 3.53 (s, 2H), 3.38 (s, 2H), 3.34 (dxt, 2H), 3.27 (s, 2H), 3.01 (d, 2H), 2.12-2.09 (m, 4H), 1.83-1.52 (m, 6H), 1.36-1.26 (dxq, 2H).

Step 3: Debenzylation was performed as described in Preparation 14, Step 5.

Preparation 57

1-Methyl-3-(tetrahydropyran-4-ylmethyl)-bicyclo[3.2.1]-1β,3,8-triaza-spiro[4.5]dodecan-2-one

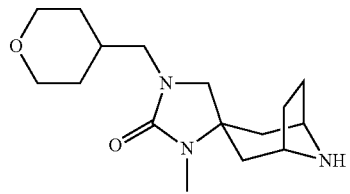

The compound was obtained from methylation (see Preparation 14, Step 4) and debenzylation (see Preparation 14, Step 5) of Preparation 56.

1H NMR (400 MHz, CDCl$_3$): δ [ppm] 3.91 (dxd, 2H), 3.70 (br s, 2H), 3.32 (dxt, 2H), 3.32 (s, 2H), 2.98 (d, 2H), 2.65 (s, 3H), 2.08 (dxd, 2H), 1.93-1.89 (m, 2H), 1.76 (q, 2H), 1.75-1.70 (m, 1H), 1.63 (d, 2H), 1.52 (dxd, 2H), 1.28 (dxq, 2H).

Preparation 58

1-Ethyl-3-(tetrahydropyran-4-ylmethyl)-bicyclo[3.2.1]-1β,3,8-triaza-spiro[4.5]dodecan-2-one

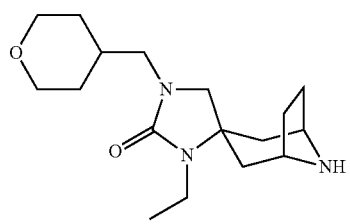

The compound was obtained from ethylation (see Preparation 14, Step 4) and debenzylation (see Preparation 14, Step 5) of Preparation 56.

1H NMR (400 MHz, CDCl$_3$): δ [ppm] 4.11 (br s, 2H), 3.95 (dxd, 2H), 3.36 (s, 2H), 3.32 (dxd, 2H), 3.25 (q, 2H), 3.00 (d, 2H), 2.47 (dxd, 2H), 2.43-2.29 (m, 2H), 1.93 (q, 2H), 1.85 (d, 2H), 1.76 (m, 1H), 1.53 (dxd, 2H), 1.36-1.26 (dxq, 2H), 1.13 (t, 3H).

Preparation 59

1-Isobutyl-3-(tetrahydropyran-4-ylmethyl)-bicyclo[3.2.1]-1β,3,8-triaza-spiro[4.5]dodecan-2-one

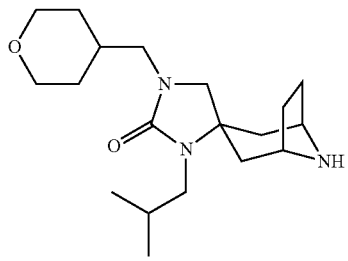

The compound was obtained from isobutylation (see Preparation 14, Step 4) and debenzylation (see Preparation 14, Step 5) of Preparation 56.

1H NMR (400 MHz, CDCl$_3$): δ [ppm] 3.92 (m, 2H), 3.68 (br s, 2H), 3.40 (m, 1H), 3.34 (d×t, 2H), 3.31 (s, 2H), 3.00 (d, 2H), 2.77 (d, 2H), 2.00 (d×d, 2H), 1.95-1.85 (m, 2H), 1.84-1.67 (m, 5H), 1.53 (m, 2H), 1.32 (d×q, 2H), 0.84 (d, 6H).

Compounds representative of the present invention are listed in Table 3:

TABLE 3

| Preparation # | Structure | Compound name |
|---|---|---|
| 9 | 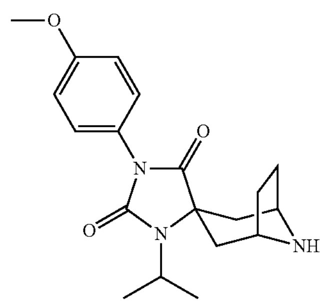 | 1-Isopropyl-3-(4-methoxyphenyl)-bicyclo[3.2.1]-1β,3,8-triaza-spiro[4.5]dodecan-2,4-dione |
| 10 | 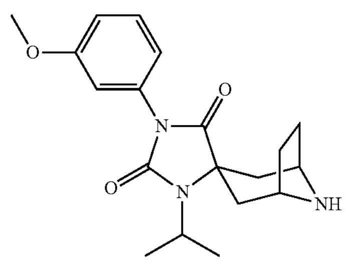 | 1-Isopropyl-3-(3-methoxyphenyl)-bicyclo[3.2.1]-1β,3,8-triaza-spiro[4.5]dodecan-2,4-dione |
| 11 | 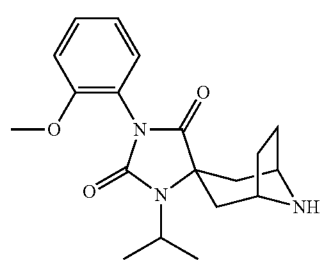 | 1-Isopropyl-3-(2-methoxyphenyl)-bicyclo[3.2.1]-1β,3,8-triaza-spiro[4.5]dodecan-2,4-dione |
| 12 | 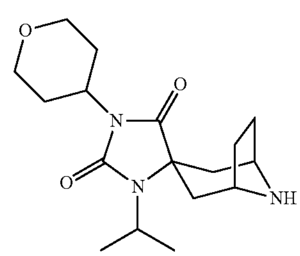 | 1-Isopropyl-3-(tetrahydropyran-4-yl)-bicyclo[3.2.1]-1β,3,8-triaza-spiro[4.5]dodecan-2,4-dione |

TABLE 3-continued

| Preparation # | Structure | Compound name |
|---|---|---|
| 14 | 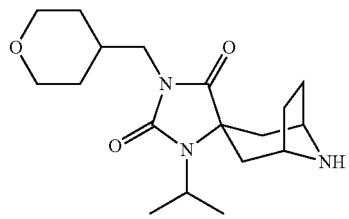 | 1-Isopropyl-3-(tetrahydropyran-4-ylmethyl)-bicyclo[3.2.1]-1β,3,8-triaza-spiro[4.5]dodecan-2,4-dione |
| 15 | 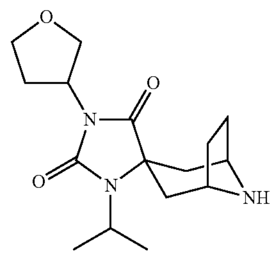 | 1-Isopropyl-3-(tetrahydrofuran-3-yl)-bicyclo[3.2.1]-1β,3,8-triaza-spiro[4.5]dodecan-2,4-dione |
| 16 | 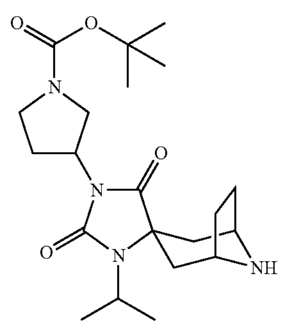 | 3-(1-Isopropyl-bicyclo[3.2.1]-1β,3,8-triaza-spiro[4.5]dodecan-2,4-dione)-pyrrolidine-1-carboxylic acid tert-butyl ester |
| 17 | 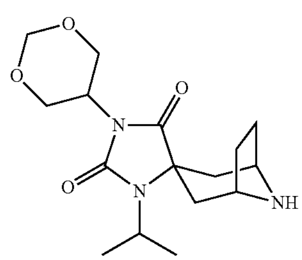 | 3-[1,3]Dioxan-5-yl-1-isopropyl-bicyclo[3,2.1]-1β,3,8-triaza-spiro[4.5]dodecan-2,4-dione |
| 18 | 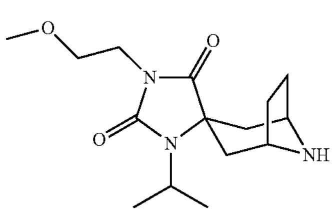 | 1-Isopropyl-3-(2-methoxyethyl)-bicyclo[3.2.1]-1β,3,8-triaza-spiro[4.5]dodecan-2,4-dione |
| 19 | 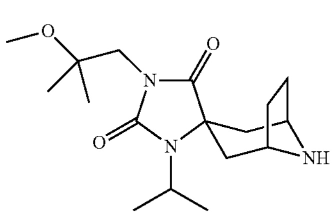 | 1-Isopropyl-3-(2-methoxy-2-methylpropyl)-bicyclo[3.2.1]-1β,3,8-triaza-spiro[4.5]dodecan-2,4-dione |

TABLE 3-continued

| Preparation # | Structure | Compound name |
|---|---|---|
| 20 | 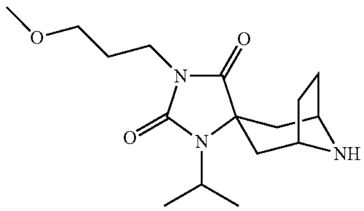 | 1-Isopropyl-3-(3-methoxypropyl)-bicyclo[3.2.1]-1β,3,8-triaza-spiro[4.5]dodecan-2,4-dione |
| 21 | 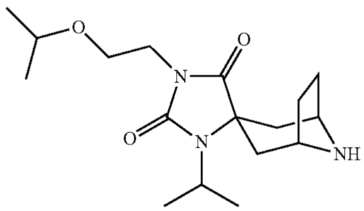 | 3-(2-Isopropoxyethyl)-1-isopropyl-bicyclo[3.2.1]-1β,3,8-triaza-spiro[4.5]dodecan-2,4-dione |
| 22 | 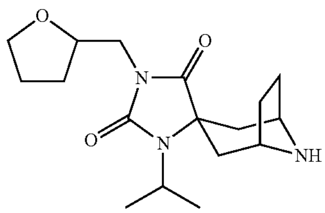 | 1-Isopropyl-3-(tetrahydrofuran-3-ylmethyl)-bicyclo[3.2.1]-1β,3,8-triaza-spiro[4.5]dodecan-2,4-dione |
| 23 | 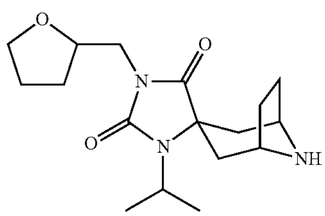 | 1-Isopropyl-3-(tetrahydrofuran-2-ylmethyl)-bicyclo[3.2.1]-1β,3,8-triaza-spiro[4,5]dodecan-2,4-dione |
| 24 | 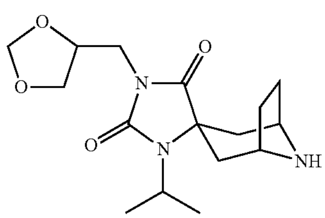 | 3-[1,3]Dioxolan-4-ylmethyl-1-isopropyl-bicyclo[3.2.1]-1β,3,8-triaza-spiro[4.5]dodecan-2,4-dione |
| 25 | 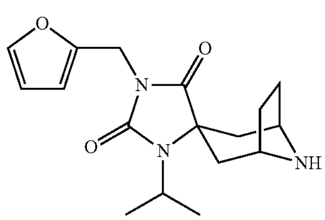 | 3-Furan-2-ylmethyl-1-isopropyl-bicyclo[3.2.1]-1β,3,8-triaza-spiro[4,5]dodecan-2,4-dione |
| 26 | 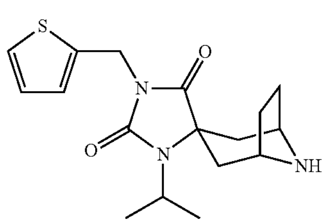 | 1-Isopropyl-3-thiophen-2-ylmethyl-bicyclo[3.2.1]-1β,3,8-triaza-spiro[4,5]dodecan-2-4-dione |

TABLE 3-continued

| Preparation # | Structure | Compound name |
| --- | --- | --- |
| 27 | 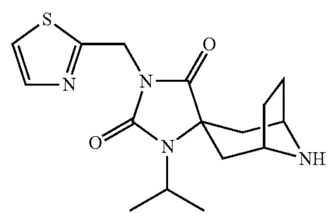 | 1-Isopropyl-3-thiazol-2-ylmethyl-bicyclo[3.2.1]-1β,3,8-triaza-spiro[4,5]dodecan-2-4-dione |
| 29 | 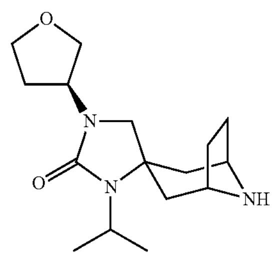 | (S)-1-isopropyl-3-(tetrahydrofuran-3-yl)-bicyclo[3.2.1]-1β,3,8-triaza-spiro[4.5]dodecan-2-one |
| 30 | 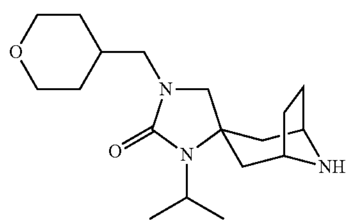 | 1-Isopropyl-3-(tetrahydropyran-4-ylmethyl)-bicyclo[3.2.1]-1β,3,8-triaza-spiro[4.5]dodecan-2-one |
| 31 | 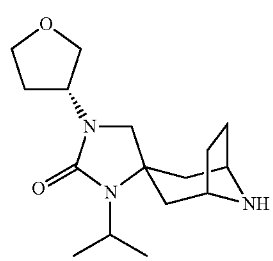 | (R)-1-isopropyl-3-(tetrahydrofuran-3-yl)-bicyclo[3.2.1]-1β,3,8-triaza-spiro[4.5]dodecan-2-one |
| 32 | 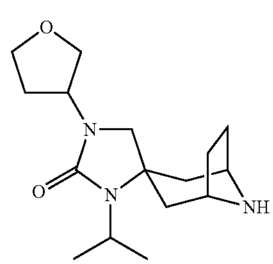 | 1-Isopropyl-3-(tetrahydrofuran-3-yl)-bicyclo[3.2.1]-1β,3,8-triaza-spiro[4,5]dodecan-2-one |
| 33 | 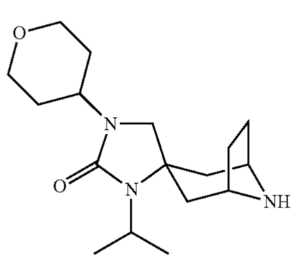 | 1-Isopropyl-3-(tetrahydropyran-4-yl)-bicyclo[3.2.1]-1β,3,8-triaza-spiro[4.5]dodecan-2-one |

TABLE 3-continued

| Preparation # | Structure | Compound name |
| --- | --- | --- |
| 34 | 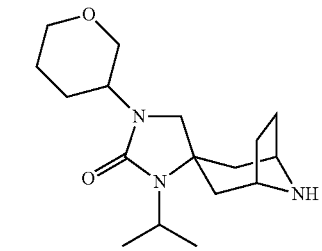 | 1-Isopropyl-3-(tetrahydropyran-3-yl)-bicyclo[3.2.1]-1β,3,8-triaza-spiro[4.5]dodecan-2-one |
| 35 | 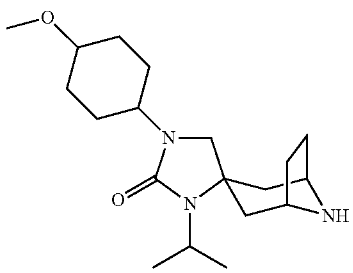 | 1-Isopropyl-3-(4-methoxy-cyclohexyl)-bicyclo[3.2.1]-1β,3,8-triaza-spiro[4.5]dodecan-2-one |
| 36 | 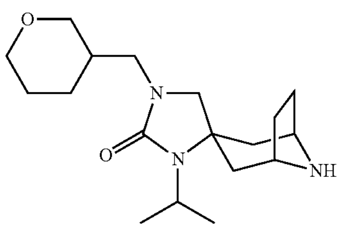 | 1-Isopropyl-3-(tetrahydropyran-3-ylmethyl)-bicyclo[3.2.1]-1β,3,8-triaza-spiro[4.5]dodecan-2-one |
| 37 | 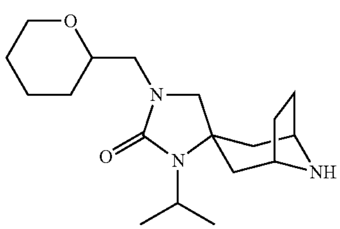 | 1-Isopropyl-3-(tetrahydropyran-2-ylmethyl)-bicyclo[3.2.1]-1β,3,8-triaza-spiro[4.5]dodecan-2-one |
| 38 | 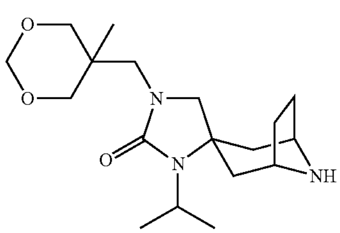 | 1-Isopropyl-3-(5-methyl-[1,3]dioxan-5-ylmethyl)-bicyclo[3.2.1]-1β,3,8-triaza-spiro[4.5]dodecan-2-one |
| 39 | 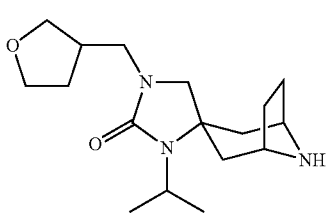 | 1-Isopropyl-3-(tetrahydrofuran-3-ylmethyl)-bicyclo[3.2.1]-1β,3,8-triaza-spiro[4.5]dodecan-2-one |

TABLE 3-continued

| Preparation # | Structure | Compound name |
|---|---|---|
| 40 | 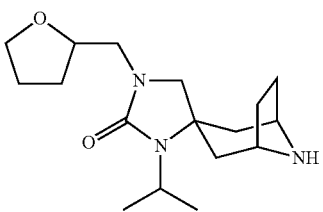 | 1-Isopropyl-3-(tetrahydrofuran-2-ylmethyl)-bicyclo[3.2.1]-1β,3,8-triaza-spiro[4.5]dodecan-2-one |
| 41 | 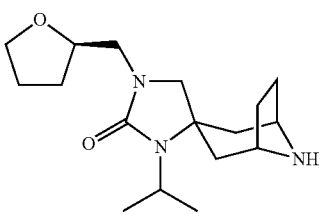 | (R)-1-Isopropyl-3-(tetrahydrofuran-2-ylmethyl)-bicyclo[3.2.1]-1β,3,8-triaza-spiro[4.5]dodecan-2-one |
| 42 | 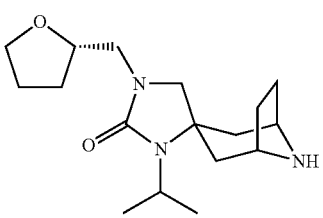 | (S)-1-Isopropyl-3-(tetrahydrofuran-2-ylmethyl)-bicyclo[3.2.1]-1β,3,8-triaza-spiro[4.5]dodecan-2-one |
| 43 | 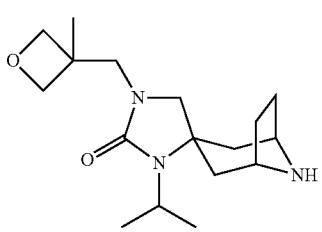 | 1-Isopropyl-3-(3-methyl-oxetan-3-ylmethyl)-bicyclo[3.2.1]-1β,3,8-triaza-spiro[4.5]dodecan-2-one |
| 44 | 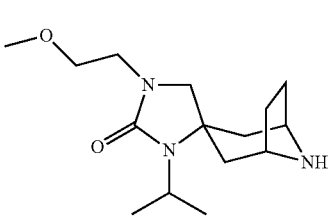 | 1-Isopropyl-3-(2-methoxyethyl)-bicyclo[3.2.1]-1β,3,8-triaza-spiro[4.5]dodecan-2-one |
| 45 | 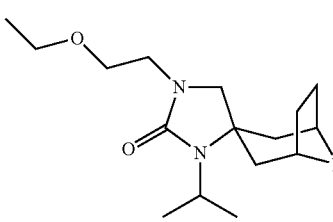 | 1-Isopropyl-3-(2-ethoxyethyl)-bicyclo[3.2.1]-1β,3,8-triaza-spiro[4.5]dodecan-2-one |
| 46 | 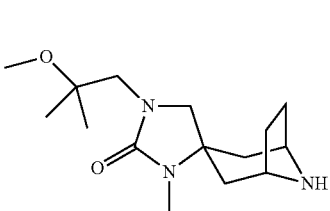 | 1-Isopropyl-3-(2-methoxy-2-methylpropyl)-bicyclo[3.2.1]-1β,3,8-triaza-spiro[4.5]dodecan-2-one |

TABLE 3-continued

| Preparation # | Structure | Compound name |
|---|---|---|
| 47 | 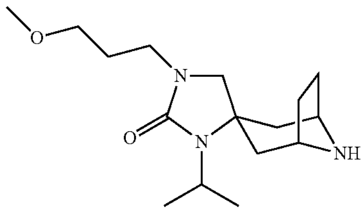 | 1-Isopropyl-3-(3-methoxypropyl)-bicyclo[3.2.1]-1β,3,8-triaza-spiro[4.5]dodecan-2-one |
| 48 | 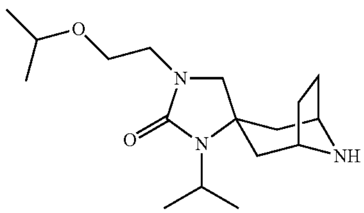 | 3-(2-Isopropoxyethyl)-1-isopropyl-bicyclo[3.2.1]-1β,3,8-triaza-spiro[4.5]dodecan-2-one |
| 49 | 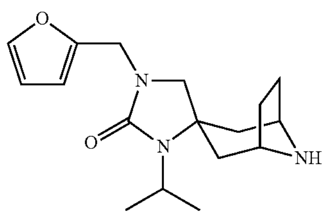 | 3-Furan-2-ylmethyl-1-isopropyl-bicyclo[3.2.1]-1β,3,8-triaza-spiro[4.5]dodecan-2-one |
| 50 | 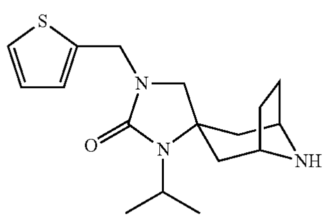 | 1-Isopropyl-3-thiophen-2-ylmethyl-bicyclo[3.2.1]-1β,3,8-triaza-spiro[4.5]dodecan-2-one |
| 51 | 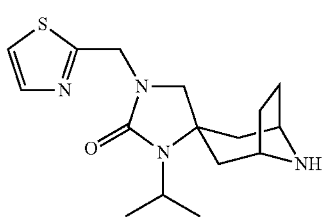 | 1-Isopropyl-3-thiazol-2-ylmethyl-bicyclo[3.2.1]-1β,3,8-triaza-spiro[4,5]dodecan-2-one |
| 52 | 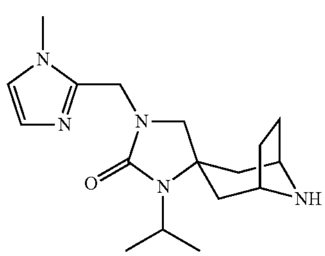 | 1-Isopropyl-3-(1-methyl-1H-imidazol-2-ylmethyl)-bicyclo[3.2.1]-1β,3,8-triaza-spiro[4.5]dodecan-2-one |

TABLE 3-continued

| Preparation # | Structure | Compound name |
|---|---|---|
| 53 | 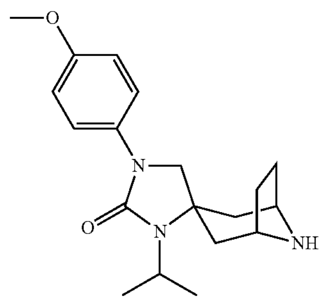 | 1-Isopropyl-3-(4-methoxy-phenyl)-bicyclo[3.2.1]-1β,3,8-triaza-spiro[4.5]dodecan-2-one |
| 54 | 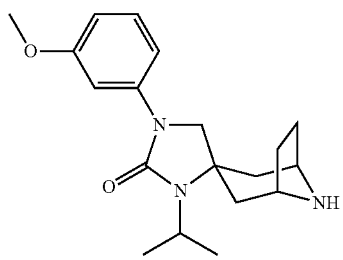 | 1-Isopropyl-3-(3-methoxy-phenyl)-bicyclo[3.2.1]-1β,3,8-triaza-spiro[4.5]dodecan-2-one |
| 55 | 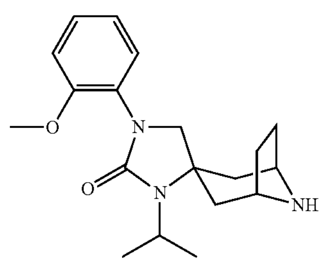 | 1-Isopropyl-3-(2-methoxy-phenyl)-bicyclo[3,2,1]-1β,3,8-triaza-spiro[4.5]dodecan-2-one |
| 56 | 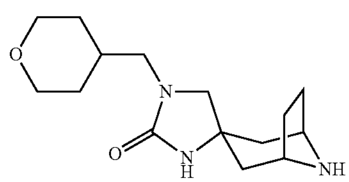 | 3-(Tetrahydropyran-4-ylmethyl)-bicyclo[3.2.1]-1β,3,8-triaza-spiro[4.5]dodecan-2-one |
| 57 | 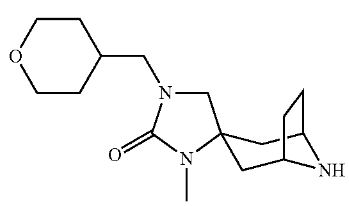 | 1-Methyl-3-(tetrahydropyran-4-ylmethyl)-bicyclo[3.2.1]-1β,3,8-triaza-spiro[4.5]dodecan-2-one |
| 58 | 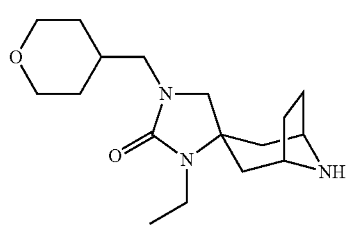 | 1-Ethyl-3-(tetrahydropyran-4-ylmethyl)-bicyclo[3.2.1]-1β,3, 8-triaza-spiro[4.5]dodecan-2-one |

TABLE 3-continued

| Preparation # | Structure | Compound name |
|---|---|---|
| 59 | 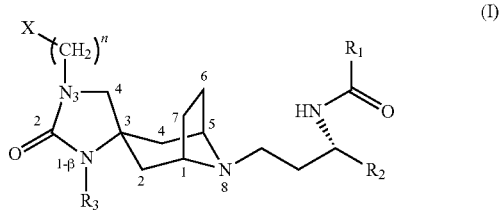 | 1-Isobutyl-3-(tetrahydropyran-4-ylmethyl)-bicyclo[3.2.1]-1β,3,8-triazaspiro[4.5]dodecan-2-one |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A compound represented by formula (I):

(I)

or a pharmaceutically acceptable salt, hydrate or solvate thereof,
wherein:
X is an optionally substituted 4 to 7 membered ring comprising 1 or 2 oxygen provided that when X is a 4 membered ring it comprises only one oxygen;
n is 0, 1 or 2;
$R_1$ is optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted $C_{3-10}$ cycloalkenyl, or optionally substituted 4 to 7 member heterocycle;
$R_2$ is optionally substituted $C_{6-12}$ aryl;
$R_3$ is optionally substituted $C_{1-10}$ alkyl, optionally substituted $C_{2-10}$ alkenyl, optionally substituted $C_{2-10}$ alkynyl; and
provided that when —$(CH_2)_n$—X is tetrahydrofuran, tetrahydropyran, oxetanyl($CH_2$)—, tetrahydrofuran($CH_2$)— or tetrahydropyran($CH_2$)—, $R_3$ is isopropyl, then $R_1$ is not 4,4 difluorocyclohexyl.

2. A compound according to claim 1, wherein when —$(CH_2)_n$—X is tetrahydrofuran, tetrahydropyran, oxetanyl ($CH_2$)—, tetrahydrofuran($CH_2$)— or tetrahydropyran ($CH_2$)—, and $R_3$ is unsubstituted $C_{2-4}$ alkyl, then $R_1$ is not halogenated cyclohexyl.

3. A compound according to claim 1, wherein when —$(CH_2)_n$—X is tetrahydrofuran, tetrahydropyran, oxetanyl ($CH_2$)—, tetrahydrofuran($CH_2$)— or tetrahydropyran ($CH_2$)—, and $R_3$ is unsubstituted $C_{1-4}$ alkyl, then $R_1$ is not halogenated cyclohexyl.

4. A compound according to claim 1, wherein
$R_2$ is unsubstituted phenyl or phenyl substituted with at least one substituent selected from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, $NR_{63}R_{64}$, $C(O)OR_{62}$, cyano, azido, amidino and guanido; and
$R_{62}$, $R_{63}$, $R_{64}$, $R_{65}$, and $R_{66}$ are each independently H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, or $C_{7-18}$ aralkyl,
or $R_{65}$ and $R_{66}$ are taken together with the oxygen atoms to form a 5 to 10 member heterocycle,
or $R_{63}$ and $R_{64}$ are taken together with the nitrogen atom to form a 3 to 10 member heterocycle.

5. A compound according to claim 1, wherein
$R_2$ is unsubstituted phenyl or phenyl substituted with at least one substituent selected from a halogen, $C_{1-6}$ alkyl, $C_{1-6}$ alkyloxy, $CF_3$, COOH, $COOC_{1-6}$ alkyl, cyano, $NH_2$, nitro, $NH(C_{1-6}$ alkyl), $N(C_{1-6}$ alkyl)$_2$ and a 3-8 member heterocycle.

6. A compound according to claim 1, wherein $R_1$ is $C_{1-6}$ alkyl optionally substituted.

7. A compound according to claim 1, wherein $R_1$ is $C_{3-7}$ cycloalkyl optionally substituted.

8. A compound according to claim 1, wherein $R_1$ is $C_{5-7}$ cycloalkenyl optionally substituted.

9. A compound according to claim 1, wherein
$R_1$ is methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl, which in each case is unsubstituted or substituted by one or more substituents selected from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, oxo, oxime, $NR_{63}R_{64}$, $C(O)OR_{62}$, cyano, azido, amidino, and guanido; and
$R_{62}$, $R_{63}$, $R_{64}$, $R_{65}$, and $R_{66}$ are each independently selected from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl, or $R_{65}$ and $R_{66}$ are taken together with the oxygen atoms to form a 5 to 10 member heterocycle, or $R_{63}$ and $R_{64}$ are taken together with the nitrogen atom to form a 3 to 10 member heterocycle.

10. A compound according to claim 1, wherein $R_1$ is cyclohexyl, cyclopentyl, cyclobutyl or cyclopropyl, which in each case is unsubstituted or substituted by one or more substituents independently selected from halogen, nitro, nitroso, $SO_3Rf$, $SO_2Rf$, $PO_3R_{65}R_{66}$, $CONRgRh$, $C_{1-6}$ alkyl, $C_{7-18}$ aralkyl, $C_{6-12}$ aryl, $C_{1-6}$ alkyloxy, $C_{6-12}$ aryloxy, $C(O)C_{1-6}$ alkyl, $C(O)C_{6-12}$ aryl, $C(O)C_{7-12}$ aralkyl, $C(O)NHRf$, 3-10 member heterocycle, 4-16 member heteroaralkyl, hydroxyl, oxo, oxime, $NRgRh$, $C(O)ORf$, cyano, azido, amidino and guanido; and Rf, $R_{65}$, $R_{66}$, Rg and Rh in each case are independently H, $C_{1-6}$ alkyl, $C_{2-6}$ alkenyl, $C_{2-6}$ alkynyl, $C_{6-12}$ aryl, 3-10 member heterocycle, 4-16 member heteroaralkyl, or $C_{7-18}$ aralkyl.

11. A compound according to claim 1, wherein $R_1$ is cyclopentenyl which is unsubstituted or substituted by one or more substituents selected from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, oxo, oxime, $NR_{63}R_{64}$, $C(O)OR_{62}$, cyano, azido, amidino, and guanido; and $R_{62}, R_{63}, R_{64}, R_{65}$, and $R_{66}$ are each independently selected from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl, or $R_{65}$ and $R_{66}$ are taken together with the oxygen atoms to form a 5 to 10 member heterocycle, or $R_{63}$ and $R_{64}$ are taken together with the nitrogen atom to form a 3 to 10 member heterocycle.

12. A compound according to claim 1, wherein $R_1$ is methyl, ethyl, vinyl, propyl, propenyl, isopropyl, butyl, isobutyl, pentyl, neopentyl, or tert-butyl.

13. A compound according to claim 1, wherein $X$—$(CH_2)_n$— is oxetanyl, tetrahydrofuranyl, tetrahydropyranyl, oxepanyl, dioxolanyl, dioxanyl, oxetanyl-$CH_2$—, tetrahydrofuranyl-$CH_2$—, tetrahydropyranyl-$CH_2$—, oxepanyl-$CH_2$—, dioxolanyl-$CH_2$—, or dioxanyl-$CH_2$—, which in each case is unsubstituted or substituted by one or more substituents selected from halogen, hydroxy, $C_{1-6}$ alkyl, $NR_{63}R_{64}$, nitro, $CONR_{63}R_{64}$, $C_{1-6}$ alkyloxy, $C(O)OR_{62}$, cyano, and azido; and $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen atom to form a 3 to 10 member heterocycle.

14. A compound according to claim 1, wherein $X$—$(CH_2)_n$— is oxetanyl, tetrahydrofuranyl, tetrahydropyranyl, oxepanyl, dioxolanyl, dioxanyl, oxetanyl-$CH_2$—, tetrahydrofuranyl-$CH_2$—, tetrahydropyranyl-$CH_2$—, oxepanyl-$CH_2$—, dioxolanyl-$CH_2$—, or dioxanyl-$CH_2$—, which in each case is unsubstituted or substituted by one or more substituents selected from halogen, $C_{1-6}$ alkyl, $NR_{63}R_{64}$, nitro, $CONR_{63}R_{64}$, $C_{1-6}$ alkyloxy, $C(O)OR_{62}$, cyano, and azido; and $R_{62}$, $R_{63}$ and $R_{64}$ are each independently H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen atom to form a 3 to 10 member heterocycle.

15. A compound according to claim 13, wherein $X$—$(CH_2)_n$— is oxetanyl, tetrahydrofuranyl, tetrahydropyranyl, oxepanyl, dioxolanyl, dioxanyl, oxetanyl-$CH_2$—, tetrahydrofuranyl-$CH_2$—, tetrahydropyranyl-$CH_2$—, oxepanyl-$CH_2$—, dioxolanyl-$CH_2$—, dioxanyl-$CH_2$—, which in each case is unsubstituted or substituted by one or more substituents selected from a halogen, $C_{1-6}$ alkyl, $C_{1-6}$ alkyloxy, $CF_3$, COOH, $COOC_{1-6}$ alkyl, cyano, $NH_2$, nitro, $NH(C_{1-6}$ alkyl), $N(C_{1-6}$ alkyl$)_2$ and a 3-8 member heterocycle.

16. A compound according to claim 13, wherein $X$—$(CH_2)_n$— is oxetanyl, tetrahydrofuranyl, tetrahydropyranyl, oxepanyl, dioxolanyl, dioxanyl, oxetanyl-$CH_2$—, tetrahydrofuranyl-$CH_2$—, tetrahydropyranyl-$CH_2$—, oxepanyl-$CH_2$—, dioxolanyl-$CH_2$—, dioxanyl-$CH_2$—, which in each case is unsubstituted or substituted by one or more substituents selected from halogen, $C_{1-6}$ alkyl, $NH_2$, nitro, $C(O)OC_{1-6}$ alkyl, COOH, $C_{1-6}$ alkyloxy, cyano, and azido.

17. A compound according to claim 1, wherein $X$—$(CH_2)_n$— is tetrahydrofuranyl-$CH_2$—, tetrahydropyranyl-$CH_2$—, oxepanyl-$CH_2$, -dioxolanyl-$CH_2$—, or dioxanyl-$CH_2$—, which in each case is unsubstituted or substituted by one or more substituents selected from halogen, hydroxy, $C_{1-6}$ alkyl, $NH_2$, nitro, $C(O)OC_{1-6}$ alkyl, COOH, $C_{1-6}$ alkyloxy, cyano, and azido.

18. The compound according to claim 13, wherein $X$—$(CH_2)_n$— is tetrahydropyranyl-$CH_2$—.

19. A compound according to claim 1, wherein n is 0.

20. The compound according to claim 1, wherein n is 1.

21. A compound according to claim 1, wherein $R_3$ is methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl, which in each case is unsubstituted or substituted by one or more substituents selected from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, oxo, oxime, $NR_{63}R_{64}$, $C(O)OR_{62}$, cyano, azido, amidino and guanido; and $R_{62} R_{63}, R_{64}, R_{65}$, and $R_{66}$ are each independently H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, or $C_{7-18}$ aralkyl, or $R_{65}$ and $R_{66}$ are taken together with the oxygen atoms to form a 5 to 10 member heterocycle, or $R_{63}$ and $R_{64}$ are taken together with the nitrogen atom to form a 3 to 10 member.

22. A compound according to claim 21, wherein $R_3$ is methyl, ethyl, vinyl, propyl, propenyl, isopropyl, butyl, isobutyl, pentyl, neopentyl, or tert-butyl.

23. A compound according to claim 21, wherein $R_3$ is methyl, ethyl, isopropyl or isobutyl.

24. A compound according to claim 21, wherein $R_3$ is isopropyl.

25. A compound according to claim 1, wherein said compound is of formula (I'):

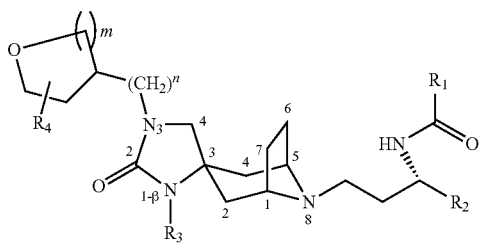
(I')

or a pharmaceutically acceptable salt, hydrate or solvate thereof,
wherein:
m is 1 or 2; and
$R_4$ is H, or optionally substituted $C_{1-10}$ alkyl; and
provided that when $R_3$ is isopropyl then $R_1$ is not 4,4 difluorocyclohexyl.

26. A compound according to claim 25, wherein when $R_3$ is unsubstituted $C_{2-4}$ alkyl, then $R_1$ is not halogenated cyclohexyl.

27. A compound according to claim 25, wherein when $R_3$ is unsubstituted $C_{1-4}$ alkyl, then $R_1$ is not halogenated cyclohexyl.

28. A compound according to claim 25, wherein
n is 0, 1 or 2;
m is 1 or 2;
$R_1$ is optionally substituted $C_{1-10}$ alkyl, optionally substituted $C_{2-10}$ alkenyl, or optionally substituted $C_{2-10}$ alkynyl;
$R_2$ is optionally substituted $C_{6-12}$ aryl;
$R_3$ is H, or optionally substituted $C_{1-10}$ alkyl;
$R_3$ is optionally substituted $C_{1-10}$ alkyl, optionally substituted $C_{2-10}$ alkenyl, or optionally substituted $C_{2-10}$ alkynyl; and
$R_4$ is H, or optionally substituted $C_{1-10}$ alkyl.

29. A compound selected from
4,4-Difluoro-1-methylcyclohexanecarboxylic acid {(S)-3-[1-isopropyl-3-(tetrahydropyran-4-ylmethyl)-bicyclo[3.2.1]-2-oxo-1β,3,8-triaza-spiro[4.5]dodec-8-yl]-1-phenyl-propyl}-amide;
Isopropylcarboxylic acid {(S)-3-[1-isopropyl-3-(tetrahydropyran-4-ylmethyl)-bicyclo[3.2.1]-2-oxo-1β,3,8-triaza-spiro[4.5]dodec-8-yl]-1-phenyl-propyl}-amide;
4,4-Difluoro-cyclohexanecarboxylic acid {(S)-3-[3-(tetrahydro-pyran-4-ylmethyl)-bicyclo[3.2.1]-2-oxo-1β,3,8-triaza-spiro[4.5]dodec-8-yl]-1-phenyl-propyl}-amide;
4,4-Difluoro-cyclohexanecarboxylic acid {(S)-3-[1-methyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;
4,4-Difluoro-cyclohexanecarboxylic acid {(S)-3-[1-ethyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;
4,4-Difluoro-cyclohexanecarboxylic acid {(S)-3-[1-isobutyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;
Cyclopropylcarboxylic acid {(S)-3-[1-isopropyl-3-(tetrahydropyran-4-ylmethyl)-bicyclo[3.2.1]-2-oxo-1β,3,8-triaza-spiro[4.5]dodec-8-yl]-1-phenyl-propyl}-amide;
Cyclopent-1-enecarboxylic acid {(S)-3-[1-isopropyl-3-(tetrahydropyran-4-ylmethyl)-bicyclo[3.2.1]-2-oxo-1β,3,8-triaza-spiro[4.5]dodec-8-yl]-1-phenyl-propyl}-amide;
1-Methyl-1H-imidazole-2-carboxylic acid {(S)-3-[1-isopropyl-3-(tetrahydropyran-4-ylmethyl)-bicyclo[3.2.1]-2-oxo-1β,3,8-triaza-spiro[4.5]dodec-8-yl]-1-phenyl-propyl}-amide;
Isopropylcarboxylic acid {(S)-3-[3-(tetrahydropyran-4-ylmethyl)-bicyclo[3.2.1]-2-oxo-1β,3,8-triaza-spiro[4.5]dodec-8-yl]-1-phenyl-propyl}-amide;
Isopropylcarboxylic acid {(S)-3-[1-methyl-3-(tetrahydropyran-4-ylmethyl)-bicyclo[3.2.1]-2-oxo-1β,3,8-triaza-spiro[4.5]dodec-8-yl]-1-phenyl-propyl}-amide;
Isopropylcarboxylic acid {(S)-3-[1-ethyl-3-(tetrahydropyran-4-ylmethyl)-bicyclo[3.2.1]-2-oxo-1β,3,8-triaza-spiro[4.5]dodec-8-yl]-1-phenyl-propyl}-amide; and
4,4-Difluoro-cyclohexanecarboxylic acid {(S)-1-isopropyl-3-(5-methyl-[1,3]dioxan-5-ylmethyl)-bicyclo[3.2.1]-2-oxo-1β,3,8-triaza-spiro[4.5]dodec-8-yl]-1-phenyl-propyl}-amide;
and pharmaceutically acceptable salts, hydrates or solvates thereof.

30. A compound according to claim 29, wherein said compound is in the form of a hydrochloride salt.

31. A compound selected from
4,4-Difluoro-cyclohexanecarboxylic acid {(S)-3-[1-isopropyl-3-(tetrahydropyran-3-yl)-bicyclo[3.2.1]-2-oxo-1β,3,8-triaza-spiro[4.5]dodec-8-yl]-1-phenyl-propyl}-amide;
4,4-Difluoro-cyclohexanecarboxylic acid {(S)-3-[1-isopropyl-3-(3-methyl-oxetan-3-ylmethyl)-bicyclo[3.2.1]-2-oxo-1β,3,8-triaza-spiro[4.5]dodec-8-yl]-1-phenyl-propyl}-amide;
4-Hydroxy-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;
Cyclohex-1-enecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;
N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-2-trifluoromethyl-acrylamide;
N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-2-methyl-acrylamide;
2-Ethyl-N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-butyramide:
N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-propionamide;
4,4-Difluoro-cyclohexanecarboxylic acid {(S)-3-[3-(5-methyl-[1,3]dioxan-5-ylmethyl)-bicyclo[3.2.1]-2-oxo-1β,3,8-triaza-spiro[4.5]dodec-8-yl]-1-phenyl-propyl}-amide;
4,4-Difluoro-cyclohexanecarboxylic acid {(S)-3-[1-methyl-3-(5-methyl-[1,3]dioxan-5-ylmethyl)-bicyclo[3.2.1]-2-oxo-1β,3,8-triaza-spiro[4.5]dodec-8-yl]-1-phenyl-propyl}-amide;
4,4-Difluoro-cyclohexanecarboxylic acid {(S)-3-[1-ethyl-3-(5-methyl-[1,3]dioxan-5-ylmethyl)-bicyclo[3.2.1]-2-oxo-1β,3,8-triaza-spiro[4.5]dodec-8-yl]-1-phenyl-propyl}-amide;

N-{(S)-3-[1-methyl-3-(5-methyl-[1,3]dioxan-5-ylmethyl)-bicyclo[3.2.1]-2-oxo-1β,3,-triaza-spiro[4.5]dodec-8-yl]-1-phenyl-propyl}-isobutyramide;

N-{(S)-3-[1-ethyl-3-(5-methyl-[1,3]dioxan-5-ylmethyl)-bicyclo[3.2.1]-2-oxo-1β,3,-triaza-spiro[4.5]dodec-8-yl]-1-phenyl-propyl}-isobutyramide;

N-{(S)-3-[1-isopropyl-3-(5-methyl-[1,3]dioxan-5-ylmethyl)-bicyclo[3.2.1]-2-oxo-1β,3,-triaza-spiro[4.5]dodec-8-yl]-1-phenyl-propyl}-isobutyramide;

4,4-Difluoro-cyclohexanecarboxylic acid {(S)-3-[1-isopropyl-3-(5-ethyl-[1,3]dioxan-5-ylmethyl)-bicyclo[3.2.1]-2-oxo-1β,3,8-triaza-spiro[4.5]dodec-8-yl]-1-phenyl-propyl}-amide;

4,4-Difluoro-cyclohexanecarboxylic acid {(S)-3-[3-([1,3]dioxolan-2-ylmethyl)-1-isopropyl-bicyclo[3.2.1]-2-oxo-1β,3,8-triaza-spiro[4.5]dodec-8-yl]-1-phenyl-propyl}-amide;

4,4-Difluoro-cyclohexanecarboxylic acid {(S)-3-[3-(5-ethyl-[1,3]dioxan-5-ylmethyl)-bicyclo[3.2.1]-2-oxo-1β,3,8-triaza-spiro[4.5]dodec-8-yl]-1-phenyl-propyl}-amide;

4,4-Difluoro-cyclohexanecarboxylic acid {(S)-3-[1-ethyl-3-(5-ethyl-[1,3]dioxan-5-ylmethyl)-bicyclo[3.2.1]-2-oxo-1β,3,8-triaza-spiro[4.5]dodec-8-yl]-1-phenyl-propyl}-amide;

N-{(S)-3-[1-ethyl-3-(5-ethyl-[1,3]dioxan-5-ylmethyl)-bicyclo[3.2.1]-2-oxo-1β,3,8-triaza-spiro[4.5]dodec-8-yl]-1-phenyl-propyl}-isobutyramide;

{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-carbamic acid methyl ester;

{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-carbamic acid ethyl ester;

{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-carbamic acid isopropyl ester;

Cis-4-hydroxy-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

4-Methoxy-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-acetamide;

2,2,2-Trifluoro-N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-acetamide;

4,4-Difluoro-cyclohexanecarboxylic acid {(S)-3-[3-([1,3]dioxan-5-ylmethyl)-bicyclo[3.2.1]-2-oxo-1β,3,8-triaza-spiro[4.5]dodec-8-yl]-1-phenyl-propyl}-amide;

4,4-Difluoro-cyclohexanecarboxylic acid {(S)-3-[1-ethyl-3-([1,3]dioxan-5-ylmethyl)-bicyclo[3.2.1]-2-oxo-1β,3,8-triaza-spiro[4.5]dodec-8-yl]-1-phenyl-propyl}-amide;

4,4-Difluoro-cyclohexanecarboxylic acid {(S)-3-[1-isopropyl-3-([1,3]dioxan-5-ylmethyl)-bicyclo[3.2.1]-2-oxo-1β,3,8-triaza-spiro[4.5]dodec-8-yl]-1-phenyl-propyl}-amide;

4,4-Difluoro-cyclohexanecarboxylic acid {(S)-3-[1-methyl-3-([1,3]dioxan-5-ylmethyl)-bicyclo[3.2.1]-2-oxo-1β,3,8-triaza-spiro[4.5]dodec-8-yl]-1-phenyl-propyl}-amide;

2,2-Difluoro-cyclopropanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

3,3,3-Trifluoro-N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-propionamide;

Trans-4-hydroxy-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

3,3-Difluoro-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

3,3-Difluoro-cyclobutanecarboxylic acid {(S)-3-[1-isopropyl-3-([1,3]dioxan-5-ylmethyl)-bicyclo[3.2.1]-2-oxo-1β,3,8-triaza-spiro[4.5]dodec-8-yl]-1-phenyl-propyl}-amide;

Trans-4-trifluoromethyl-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

1-Acetyl-piperidine-4-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

Tetrahydro-thiopyran-4-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

2H-Thiopyran-4-carboxamide tetrahydro-N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-1-oxide;

2H-Thiopyran-4-carboxamide tetrahydro-N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-1,1-dioxide;

4-Fluoro-N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-benzamide;

Trans-4-methoxy-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

Cis-4-methoxy-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

6-Oxo-piperidine-3-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

Trans-4-ethoxy-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

2-Oxo-piperidine-4-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

Trans-4-trifluoromethoxy-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

Trans-4-fluoro-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

4-Hydroxy-4-methyl-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

4-Hydroxy-4-trifluoromethyl-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

Trans-4-[1,2,3]triazol-1-yl-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

Isopropyl-carbamic acid 4-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propylcarbamoyl}-cyclohexyl ester;

1-Hydroxy-piperidine-4-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

4-Hydroxyimino-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

4-Methoxyimino-cyclohexanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

5-Oxo-pyrrolidine-3-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

1-Methyl-5-oxo-pyrrolidine-3-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

2-Oxo-imidazolidine-4-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

3-Hydroxy-cyclopentanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

2-Hydroxy-N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-2-methyl-propionamide;

N-{(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-2-methoxy-2-methyl-propionamide;

4-Hydroxy-but-2-ynoic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

4-Hydroxy-4-methyl-pent-2-ynoic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

3-Hydroxy-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

3-Methoxy-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

3-Hydroxy-3-methyl-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

3-Hydroxy-3-trifluoromethyl-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide (S)-4-Oxo-azetidine-2-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

3-Hydroxyimino-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

3-Methoxyimino-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

1-Acetyl-azetidine-3-carboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

Trans-3-acetylamino-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide;

Cis-3-acetylamino-cyclobutanecarboxylic acid {(S)-3-[1-isopropyl-3-(tetrahydro-pyran-4-ylmethyl)-bicyclo[3.2.1]-2-oxo-1β,3,8-triaza-spiro[4.5]dodec-8-yl]-1-phenyl-propyl}-amide; and pharmaceutically acceptable salts, hydrates or solvates thereof.

32. A compound according to claim 31, wherein said compound is in the form of a hydrochloride salt.

33. A method of modulating chemokine receptor activity in a subject comprising administering to the subject an effective amount of a compound according to claim 1.

34. A method for blocking cellular entry of HIV in a subject comprising administering to the subject in need thereof an effective amount of a compound according to claim 1 to block HIV from cellular entry in said subject.

35. A pharmaceutical formulation comprising a compound according to claim 1 in combination with a pharmaceutically acceptable carrier or excipient.

36. A combination useful for the prevention or treatment of diseases associated with the modulation of chemokine receptor activity which comprises a therapeutically effective amount of a compound as defined in claim 1 and therapeutically effective amount of at least one further therapeutic agent.

37. The pharmaceutical combination of claim 36 wherein said combination comprises at least one other antiviral agent selected from lamivudine, zidovudine, emtricitabine, 2',3'-dideoxy-2',3'-didehydro-thymidine, tenofovir, 2',3'-dideoxyinosine, 2',3'-dideoxycytidine, zidovudine/lamivudine combination, zidovudine/lamivudine/abacavir combination, abacavir, SPD-754, Beta-L-Fd4C, Alovudine, amdoxovir, Racivir, 9-[(2-hydroxymethyl)-1,3-dioxolan-4-yl]guanine, 2-amino-9-[(2-hydroxymethyl)-1,3-dioxolan-4-yl]adenine, Nevirapine, delavirdine, efavirenz, (+)-Calanolide A, Capravirine, DPC083, MIV-150, TMC120, TMC125, TMC-278, delavirdine, calanolides, L-697,661, nelfinavir, amprenavir, indinavir, saquinavir, ritonavir, lopinavir, Atazanavir, mozenavir, fosamprenavir, RO033-4649, Tipranavir, TMC114, SPI-256, VX-385, enfuvirtide, T-1249, TRI-999, TRI-1144, SCH-C, Schering D (SCH-D), FP21399, PRO-140, PRO 542, PRO 452, TNX-355, GW873140 (AK602), TAK-220, TAK-652, UK-427,857, BMS-806, BMS-488043, AMD3100, AMD070, AMD887, INCB9471, KRH-2731, KRH-3140, KRH-3955, S-1360, L-870,810, L-870,812, JTK-303, GS9137, MK-0518, C-2507, interleukin-2, granulocyte macrophage colony stimulating factor, erythropoietin, Multikine, Ampligen, thymomodulin, thymopentin, foscarnet, HE2000, Reticulose, Murabutide, Resveratrol, HRG214, EP HIV-1090, 2',3'-dideoxyadenosine, 3'-deoxythymidine, 2',3'-dideoxy-2',3'-didehydrocytidine, ribavirin, acyclovir, ganciclovir, alpha-, beta- or gamma-interferon, or probenecid.

38. A kit comprising: a first containment means for storing a compound according to claim 1 in the form of a pharmaceutical formulation further comprising a pharmaceutically acceptable carrier; and a second containment means for storing at least one further therapeutic agent in the form of a pharmaceutical formulation further comprising a pharmaceutically acceptable carrier.

* * * * *